US012637430B2

(12) United States Patent
Li et al.

(10) Patent No.: US 12,637,430 B2
(45) **Date of Patent: *May 26, 2026**

(54) INTERLEUKIN-17 (IL-17) INHIBITORS

(71) Applicant: HitGen Inc., Chengdu (CN)

(72) Inventors: Jin Li, Chengdu (CN); Dengyou Zhang, Chengdu (CN); Xiaoguang Bai, Chengdu (CN); Xiansi Zhou, Chengdu (CN); Xinfu Hong, Chengdu (CN); Kai Xu, Chengdu (CN); Qingran Li, Chengdu (CN); Xin Chen, Chengdu (CN); Yan Lan, Chengdu (CN)

(73) Assignee: HitGen Inc., Chengdu (CN)

( * ) Notice: Subject to any disclaimer, the term of this patent is extended or adjusted under 35 U.S.C. 154(b) by 561 days.

This patent is subject to a terminal disclaimer.

(21) Appl. No.: 18/148,941

(22) Filed: Dec. 30, 2022

(65) Prior Publication Data

US 2023/0159465 A1 May 25, 2023

Related U.S. Application Data

(63) Continuation of application No. PCT/CN2021/087548, filed on Apr. 15, 2021.

(30) Foreign Application Priority Data

Jul. 4, 2020 (CN) ........................ 202010611350.7
Jul. 14, 2020 (CN) ........................ 202010658232.1

(51) Int. Cl.
*C07D 231/12* (2006.01)
*A61P 17/06* (2006.01)
(Continued)

(52) U.S. Cl.
CPC ............ *C07D 231/12* (2013.01); *A61P 17/06* (2018.01); *A61P 29/00* (2018.01); *C07D 401/12* (2013.01);
(Continued)

(58) Field of Classification Search
CPC .. C07D 231/12; C07D 401/12; C07D 401/14; C07D 403/12; C07D 403/14;
(Continued)

(56) References Cited

U.S. PATENT DOCUMENTS

2016/0244437 A1* 8/2016 Röhn et al.

FOREIGN PATENT DOCUMENTS

CN 102985402 A 3/2013
CN 112341446 A 2/2021
(Continued)

OTHER PUBLICATIONS

Rossella Fioravanti et al., "Tranylcypromine-based LSD1 Inhibitors: Structure-Activity Relationship, Antiproliferative Effect in Leukemias and Gene Target Modulation", ChemMedChem, vol. 7, No. 15, Feb. 14, 2020, pp. 643-658, in particular table 1 compound 2h.
(Continued)

*Primary Examiner* — Sarah Pihonak
*Assistant Examiner* — Jackson J Hernandez

(57) ABSTRACT

Disclosed herein is a compound of formula (I). An application of the compound of formula (I) or a stereoisomer thereof in the preparation of a drug for inhibiting interleukin-17A (IL-17A) is further provided.
(Continued)

(I)

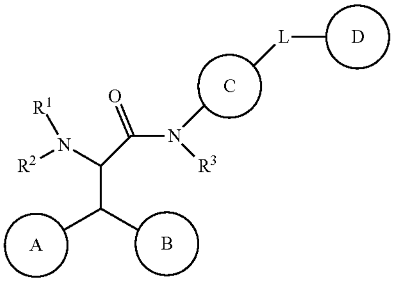

9 Claims, 11 Drawing Sheets

(51) Int. Cl.

| | |
|---|---|
| ***A61P 29/00*** | (2006.01) |
| ***C07D 401/12*** | (2006.01) |
| ***C07D 401/14*** | (2006.01) |
| ***C07D 403/12*** | (2006.01) |
| ***C07D 403/14*** | (2006.01) |
| ***C07D 405/12*** | (2006.01) |
| ***C07D 405/14*** | (2006.01) |
| ***C07D 413/14*** | (2006.01) |

(52) U.S. Cl.

CPC ......... *C07D 401/14* (2013.01); *C07D 403/12* (2013.01); *C07D 403/14* (2013.01); *C07D 405/12* (2013.01); *C07D 405/14* (2013.01); *C07D 413/14* (2013.01)

(58) Field of Classification Search

CPC .. C07D 405/12; C07D 405/14; C07D 413/14; A61P 17/06; A61P 29/00

See application file for complete search history.

(56) References Cited

FOREIGN PATENT DOCUMENTS

| | | | | |
|---|---|---|---|---|
| WO | 9812176 | A1 | | 3/1998 |
| WO | WO20000029399 | A1 | * | 5/2000 |
| WO | WO2018229079 | A1 | * | 12/2018 |
| WO | 2020127685 | A1 | | 6/2020 |
| WO | 2020182666 | A1 | | 9/2020 |
| WO | 2020190742 | A1 | | 9/2020 |

OTHER PUBLICATIONS

Claudia Binda et al., "Biochemical, Structural, and Biological Evaluation of Tranylcypromine Derivatives as Inhibitors of Histone Demethylases LSD1 and LSD2", Journal of the American Chemical Society, VOl. 132, No. 19, Apr. 28, 2010, pp. 6827-6833, in particular table 1 and supporting information scheme 2.

Jill F. Wright et al."The Human IL-17F/IL-17A Heterodimeric Cytokine Signals through the IL-17RA/IL-17RC Receptor Complex", The Journal of immunology, 2008, 181, pp. 2799-2805.

Al-Ramli et al."TH17-associated cytokines (IL-17A and IL-17F) in severe asthma", J Allergy Clin Immunol, 2009, vol. 123, No. 5, pp. 1185-1187.

Sarah L Gaffen et al."Biology of recently discovered cytokines: Interleukin-17—a unique inflammatory cytokine with roles in bone biology and arthritis" Arthritis Research & Therapy, 2004, vol. 6, No. 6, pp. 240-247.

Yutaka Komiyama et al.,"IL-17 Plays an Important Role in the Development of Experimental Autoimmune Encephalomyelitis", The Journal of immunology, 2006, 177, pp. 566-573.

* cited by examiner

INTERLEUKIN-17 (IL-17) INHIBITORS

CROSS-REFERENCE TO RELATED APPLICATIONS

This application is a continuation of International Patent Application No. PCT/CN2021/087548, filed on Apr. 15, 2021, which claims the benefit of priority from Chinese Patent Application No. 202010611350.7, filed on Jul. 4, 2020 and Chinese Patent Application No. 202010658232.1, filed on Jul. 14, 2020. The content of the aforementioned application, including any intervening amendments thereto, is incorporated herein by reference in its entirety.

TECHNICAL FIELD

This application relates to immunomodulatory compounds, and more particularly to an interleukin-17 (IL-17) inhibitor, and an application thereof in the preparation of drugs.

BACKGROUND

As a proinflammatory cytokine, Interleukin-17 (IL-17) plays an important role in the induction of other inflammatory cytokines, chemokines and adherence factor. The IL-17 family consists of cytokines that are involved in acute and chronic inflammatory responses, including IL-17A (CTLA-8), IL-17B, IL-17C, IL-17D, IL-17E (IL-25), and IL-17F. IL-17A is expressed in TH17 cells and is involved in the pathogenesis of inflammatory and autoimmune diseases. Human IL-17A is a glycoprotein, whose molecular weight is approximately 17,000 Daltons. IL-17A transmits signals into cells through the IL-17 receptor complex (IL-17RA and IL-17RC) (Wright, et al. Journal of immunology, 2008, 181:2799-2805). The main function of IL-17A is to coordinate local tissue inflammation through pro-inflammatory and the up-regulation of migrating cytokines and chemokines (including IL-6, G-CSF, TNF-α, IL-1, CXCL1, CCL2, CXCL2) of the neutrophils. Moreover, the matrix metalloproteinase allows the activated T cells to penetrate the extracellular matrix. Researches have shown that IL-17A plays an important role in the treatments for severe asthma and chronic obstructive pulmonary disease (COPD). Patients, who have suffered from such diseases, are often unresponsive or poorly responsive to the currently-available drugs (Al-Ramli et al. *J Allergy Clin Immunol,* 2009, 123: 1185-1187). The up-regulation of IL-17A levels is implicated in many diseases, such as rheumatoid arthritis (RA), bone erosion, intraperitoneal abscess, inflammatory bowel disease, allogeneic graft rejection, psoriasis, atherosclerosis, asthma, and multiple sclerosis (Gaffen, S L et al. *Arthritis Research & Therapy,* 2004, 6:240-247).

The combination of targeting IL-17A and IL-17RA is an effective strategy for the treatment of IL-17A-mediated autoimmune inflammatory diseases. In addition, treatment of animals with IL-17A neutralizing antibodies reduces disease incidence and severity in autoimmune encephalomyelitis (Komiyama Y et al. J. Immunol., 2006, 177:566-573). In clinical trials, IL-17A antibodies have shown promising results in the treatment of IL-7A mediated inflammatory diseases (including asthma, psoriasis, rheumatoid arthritis, ankylosing spondylitis and multiple sclerosis). The IL-17A antibody (Cosentyx/secukinumab by Novartis company) was approved for the treatment of psoriasis by Food and Drug Administration (FDA) in January 2015.

In spite of the existence of multiple IL-17A antibodies, less attention has been paid on small-molecular-specific inhibitors of IL-17 with oral bioavailability. In view of the consideration of antibody production cost and the limitation of administration route, IL-17A small-molecular inhibitor drugs have promising prospects on research and development.

SUMMARY

In a first aspect, this application provides a compound of formula (I) or a deuterated compound, a stereoisomer, or a pharmaceutically acceptable salt thereof:

(I)

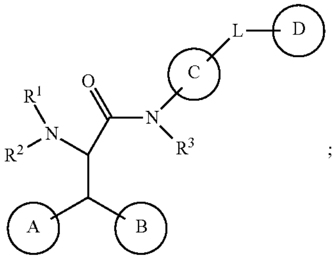

;

wherein $R^1$ is selected from the group consisting of —$C_{0-2}$ alkylene-(3- to 10-membered cycloalkyl), —$C_{0-2}$ alkylene-(3- to 6-membered heterocycloalkyl), —$C_{0-2}$ alkylene-(5- to 10-membered aromatic ring), —$C_{0-2}$ alkylene-(5- to 10-membered heteroaromatic ring), —$C_{0-2}$ alkylene-C(O)$R^{11}$, —$C_{0-2}$ alkylene-C(O)$NR^{11}R^{12}$, —$C_{0-2}$ alkylene-C(O)$OR^{11}$, —$C_{0-2}$ alkylene-S(O)$R^{11}$, —$C_{0-2}$ alkylene-S(O)$NR^{11}R^{12}$, —$C_{0-2}$ alkylene-S(O)$OR^{11}$, —$C_{0-2}$ alkylene-$S(O)_2R^{11}$, —$C_{0-2}$ alkylene-$S(O)_2NR^{11}R^{12}$, —$C_{0-2}$ alkylene-$S(O)_2OR^{11}$, —$C_{0-2}$ alkylene-P(O)$R^{11}R^{12}$, —$C_{0-2}$ alkylene-P(O)($OR^{11}$)$R^{12}$ and —$C_{0-2}$ alkylene-P(O)($OR^{11}$)($OR^{12}$); wherein alkylene, cycloalkyl, heterocycloalkyl, aromatic ring and heteroaromatic ring are independently unsubstituted or substituted with 1, 2, or 3 $R^{1a}$ groups;

$R^{11}$ and $R^{12}$ are independently selected from the group consisting of hydrogen, $C_{1-6}$ alkyl, halogen-substituted $C_{1-6}$ alkyl, —$C_{0-2}$ alkylene-(3- to 10-membered cycloalkyl), —$C_{0-2}$ alkylene-(3- to 10-membered heterocycloalkyl), —$C_{0-2}$ alkylene-(5- to 10-membered aromatic ring) and —$C_{0-2}$ alkylene-(5- to 10-membered heteroaromatic ring); wherein alkyl, alkylene, cycloalkyl, heterocycloalkyl and aromatic ring, heteroaromatic ring are independently unsubstituted or substituted with 1, 2, or 3 $R^{1a}$ groups;

the $R^{1a}$ groups are each independently selected from the group consisting of hydrogen, halogen, cyano, =O, nitro, —$C_{1-6}$ alkyl, halogen-substituted-$C_{1-6}$ alkyl, —$C_{0-2}$ alkylene-$OR^{1b}$, —$C_{0-2}$ alkylene-C(O)$R^{1b}$, —$C_{0-2}$ alkylene-C(O)$NR^{1b}R^{1c}$, —$C_{0-2}$ alkylene-$NR^{1b}R^{1c}$, —$C_{0-2}$ alkylene-$NR^{1b}$C(O)$R^{1c}$, —Co-4 alkylene-$S(O)_2R^{1b}R^{1c}$, —$C_{0-2}$ alkylene-(3- to 10-membered cycloalkyl), —$C_{0-2}$ alkylene-(3- to 10-membered heterocycloalkyl), —$C_{0-2}$ alkylene-(5- to 10-membered aromatic ring) and —$C_{0-2}$ alkylene-(5- to 10-membered heteroaromatic ring); wherein alkyl, alkylene, cycloalkyl, heterocycloalkyl, aromatic ring and heteroaromatic ring are independently unsubstituted or substituted with 1, 2, or 3 $R^{1b}$ groups;

$R^{1b}$ and $R^{1c}$ are independently selected from the group consisting of hydrogen, $C_{1-6}$ alkyl, halogen-substituted $C_{1-6}$ alkyl, halogen, cyano, =O, nitro, —OH, —O($C_{1-6}$ alkyl), —$NH_2$, —NH($C_{1-6}$ alkyl) and —N($C_{1-6}$ alkyl) ($C_{1-6}$ alkyl);

$R^2$ and $R^3$ are independently selected from the group consisting of hydrogen, —$C_{1-6}$ alkyl and —$C_{0-2}$ alkylene-(3- to 10-membered cycloalkyl);

A ring is selected from the group consisting of 3- to 10-membered cycloalkyl, 3- to 10-membered heterocycloalkyl, 5- to 10-membered aromatic ring, 5- to 10-membered heteroaromatic ring, 5- to 12-membered spiro ring, 5- to 12-membered spiro heterocycle, 5- to 12-membered bridged ring and 5- to 12-membered bridged heterocycle; wherein cycloalkyl, heterocycloalkyl, aromatic ring, heteroaromatic ring, spiro ring, spiro heterocycle, bridged ring and bridged heterocycle are independently unsubstituted or substituted with 1, 2, or 3 $R^{A1}$ groups;

the $R^{A1}$ groups are each independently selected from the group consisting of hydrogen, $C_{1-6}$ alkyl, halogen-substituted $C_{1-6}$ alkyl, halogen, cyano, =O, nitro, —OH, —O($C_{1-6}$ alkyl), —$NH_2$, —NH($C_{1-6}$ alkyl), —N($C_{1-6}$ alkyl) ($C_{1-6}$ alkyl), —$C_{0-2}$ alkylene-(3- to 10-membered cycloalkyl), —$C_{0-2}$ alkylene-(3- to 10-membered heterocycloalkyl), —$C_{0-2}$ alkylene-(5- to 10-membered aromatic ring) and —$C_{0-2}$ alkylene-(5- to 10-membered heteroaromatic ring);

B ring is selected from the group consisting of 3- to 10-membered cycloalkyl, 3- to 10-membered heterocycloalkyl, 5- to 10-membered aromatic ring, 5- to 10-membered heteroaromatic ring, 5- to 12-membered spiro ring, 5- to 12-membered spiro heterocycle, 5- to 12-membered bridged ring and 5- to 12-membered bridged heterocycle; wherein cycloalkyl, heterocycloalkyl, aromatic ring, heteroaromatic ring, spiro ring, spiro heterocycle, bridged ring and bridged heterocycle are independently unsubstituted or substituted with 1, 2, or 3 $R^{B1}$ groups;

the $R^{B1}$ groups are independently selected from the group consisting of hydrogen, $C_{1-6}$ alkyl, halogen-substituted $C_{1-6}$ alkyl, halogen, cyano, =O, nitro, —OH, —O($C_{1-6}$ alkyl), —$NH_2$, —NH($C_{1-6}$ alkyl), —N($C_{1-6}$ alkyl) ($C_{1-6}$ alkyl), —$C_{0-2}$ alkylene-(3- to 10-membered cycloalkyl), —$C_{0-2}$ alkylene-(3- to 10-membered heterocycloalkyl), —$C_{0-2}$ alkylene-(5- to 10-membered aromatic ring) and —$C_{0-2}$ alkylene-(5- to 10-membered heteroaromatic ring);

C ring is selected from the group consisting of 3- to 10-membered cycloalkyl, 3- to 10-membered heterocycloalkyl, 5- to 10-membered aromatic ring, 5- to 10-membered heteroaromatic ring, 5- to 12-membered spiro ring, 5- to 12-membered spiro heterocycle, 5- to 12-membered bridged ring and 5- to 12-membered bridged heterocycle; wherein cycloalkyl, heterocycloalkyl, aromatic ring, heteroaromatic ring, spiro ring, spiro heterocycle, bridged ring and bridged heterocycle are independently unsubstituted or substituted with 1, 2, 3 or 4 $R^{C1}$ groups;

the $R^{C1}$ groups are each independently selected from the group consisting of hydrogen, halogen, cyano, =O, nitro, —$C_{1-6}$ alkyl, halogen-substituted-$C_{1-6}$ alkyl, —$C_{0-2}$ alkylene-$OR^{C2}$, —$C_{0-2}$ alkylene-C(O)$R^{C2}$, —$C_{0-4}$ alkylene-C(O)$NR^{C2}R^{C3}$, —$C_{0-2}$ alkylene-$NR^{C2}R^{C3}$, —$C_{0-2}$ alkylene-$NR^{C2}$C(O)$R^{C3}{}_2$, 3- to 10-membered cycloalkyl and 3- to 10-membered heterocycloalkyl; wherein alkyl and alkylene are independently unsubstituted or substituted with 1, 2 or 3 $R^{C4}$ groups;

$R^{C2}$ and $R^{C3}$ are independently selected from the group consisting of hydrogen, —$C_{1-6}$ alkyl, —$C_{0-2}$ alkylene-$OR^{C4}$, —$C_{0-2}$ alkylene-(3- to 10-membered cycloalkyl) and —$C_{0-2}$ alkylene-(3- to 10-membered heterocycloalkyl); wherein alkyl, alkylene, cycloalkyl are independently unsubstituted or substituted with 1, 2 or 3 $R^{C4}$ groups;

the $R^{C4}$ groups are each independently selected from the group consisting of hydrogen, $C_{1-6}$ alkyl, halogen-substituted $C_{1-6}$ alkyl, halogen, cyano, =O, nitro, —OH, —O($C_{1-6}$ alkyl), —$NH_2$, —NH($C_{1-6}$ alkyl) and —N($C_{1-6}$ alkyl) ($C_{1-6}$ alkyl);

or when two $R^{C1}$ groups are linked to the same atom, the two $R^{C1}$ groups are combined to form 3- to 10-membered cycloalkyl or 3- to 10-membered heterocycloalkyl;

L is O, S, $CR^{D1}R^{D1}$, $NR^L$, $NR^L$C(O), $NR^L$S(O), $NR^L$S$(O)_2$, C(O)$NR^L$, C(O), S(O)$NR^L$, or $S(O)_2NR^L$, or absent;

$R^L$ is selected from the group consisting of hydrogen, —$C_{1-6}$ alkyl and —$C_{0-2}$ alkylene-(3- to 10-membered cycloalkyl);

D ring is 3- to 10-membered cycloalkyl, 3- to 10-membered heterocycloalkyl, 5- to 10-membered aromatic ring, 5- to 10-membered heteroaromatic ring, 5- to 12-membered spiro ring, 5- to 12-membered spiro heterocycle, 5- to 12-membered bridged ring or 5- to 12-membered bridged heterocycle, or absent; wherein cycloalkyl, heterocycloalkyl, aromatic ring, heteroaromatic ring, spiro ring, spiro heterocycle, bridged ring, bridged heterocycle are independently unsubstituted or substituted with 1, 2, or 3 $R^{D1}$ groups;

when the L is absent and the D ring is not absent, the C ring is directly linked to the D ring;

the $R^{D1}$ groups are each independently selected from the group consisting of hydrogen, halogen, cyano, =O, nitro, —$C_{1-6}$ alkyl, halogen-substituted-$C_{1-6}$ alkyl, —$C_{0-2}$ alkylene-$OR^{D2}$, —$C_{0-2}$ alkylene-C(O)$R^{D2}$, —$C_{0-2}$ alkylene-C(O)$NR^{D2}R^{D3}$, —$C_{0-2}$ alkylene-$NR^{D2}R^{D3}$, —$C_{0-2}$ alkylene-$NR^{D2}$C(O)$R^{D3}$, —$C_{0-4}$ alkylene-OP(O)$(OH)_2$, —$C_{0-2}$ alkylene-(3- to 10-membered cycloalkyl), —$C_{0-2}$ alkylene-(3- to 10-membered heterocycloalkyl), —$C_{0-2}$ alkylene-(5- to 10-membered aromatic ring) and —$C_{0-2}$ alkylene-(5- to 10-membered heteroaromatic ring); wherein alkyl, alkylene, cycloalkyl, heterocycloalkyl, aromatic ring and heteroaromatic ring are independently unsubstituted or substituted with 1, 2 or 3 $R^{D4}$ groups;

$R^{D2}$ and $R^{D3}$ are independently selected from the group consisting of hydrogen, $C_{1-6}$ alkyl, —$C_{0-2}$ alkylene-$OR^{D4}$, —$C_{0-2}$ alkylene-(3- to 10-membered cycloalkyl), —$C_{0-2}$ alkylene-(3- to 10-membered heterocycloalkyl), —$C_{0-2}$ alkylene-(5- to 10-membered aromatic ring) and —$C_{0-2}$ alkylene-(5- to 10-membered heteroaromatic ring); wherein alkyl, alkylene, cycloalkyl, heterocycloalkyl, aromatic ring and heteroaromatic ring are independently unsubstituted or substituted with 1, 2, or 3 $R^{D4}$ groups;

the $R^{D4}$ groups are each independently selected from the group consisting of hydrogen, $C_{1-6}$ alkyl, halogen-substituted $C_{1-6}$ alkyl, halogen, cyano, =O, nitro, —OH, —O($C_{1-6}$ alkyl), —$NH_2$, —NH($C_{1-6}$ alkyl), —N($C_{1-6}$ alkyl) ($C_{1-6}$ alkyl), —$C_{0-2}$ alkylene-(3- to 10-membered cycloalkyl), —$C_{0-2}$ alkylene-(3- to 10-membered heterocycloalkyl), —$C_{0-2}$ alkylene-(5- to 10-membered aromatic ring) and —$C_{0-2}$ alkylene-(5- to 10-membered heteroaromatic ring); and when the C ring is benzene ring, and L is absent, the D ring is not 5- to 6-membered heteroaromatic ring.

In an embodiment, $R^1$ is —C(O)$R^{11}$; $R^{11}$ is substituted or unsubstituted 5- to 6-membered heteroaromatic ring; wherein the substituted 5- to 6-membered heteroaromatic ring comprises 1-3 $R^{1a}$ substituents independently selected from the group consisting of hydrogen, halogen, cyano, =O, =S, —$C_{1-6}$ alkyl, halogen-substituted $C_{1-6}$ alkyl, —$C_{0-2}$ alkylene-O$R^{1b}$, 3- to 6-membered cycloalkyl and 3- to 6-membered heterocycloalkyl; wherein $R^{1b}$ is selected from the group of hydrogen, $C_{1-6}$ alkyl and halogen-substituted $C_{1-6}$ alkyl.

In an embodiment, $R^1$ is —C(O)$R^{11}$; wherein $R^{11}$ is selected from the group consisting of

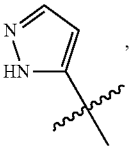 , 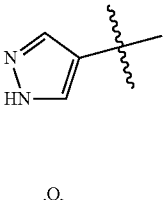 , 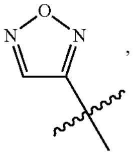 ,

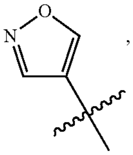 , 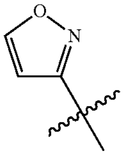 and 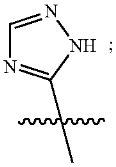 ;

wherein

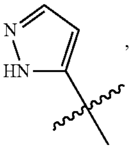 , 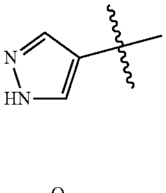 , 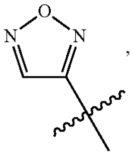 ,

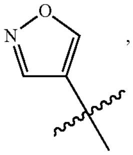 , 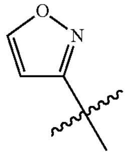 and 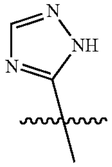

are independently unsubstituted or substituted with 1, 2 or 3 $R^{1a}$ groups; $R^{1a}$ groups are independently selected from the group consisting of hydrogen, halogen, cyano, —$C_{1-6}$ alkyl, halogen-substituted-$C_{1-6}$ alkyl, 3- to 6-membered cycloalkyl and —$C_{0-2}$ alkylene-O$R^{1b}$, wherein $R^{1b}$ is selected from the group consisting of hydrogen, $C_{1-6}$ alkyl and halogen-substituted $C_{1-6}$ alkyl.

In some embodiments, $R^1$ is —C(O)$R^{11}$; $R^{11}$ is selected from the group consisting of

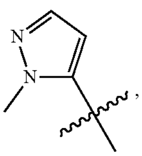 , 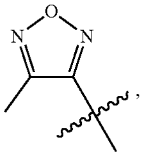 , 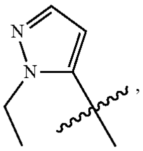 ,

-continued

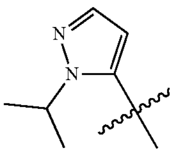 , 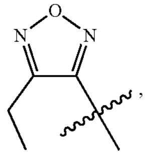 , 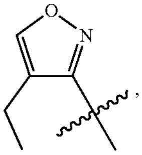 ,

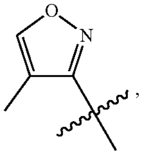 , 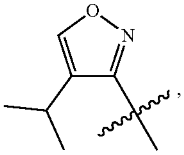 , 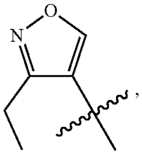 ,

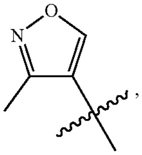 , 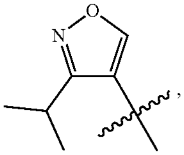 , 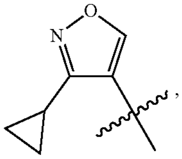 ,

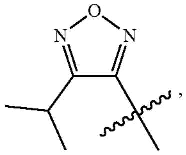 , 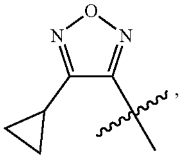 , 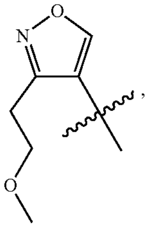 ,

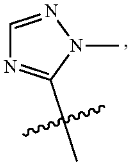 , 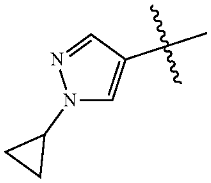 and

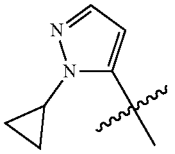 .

In an embodiment, the $R^1$ is selected from the group consisting of

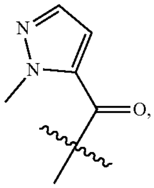 , 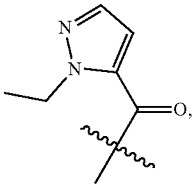 ,

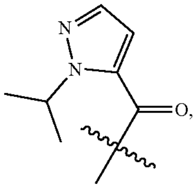 , 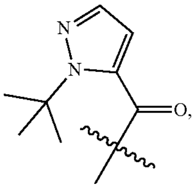 ,

-continued
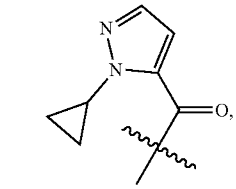,
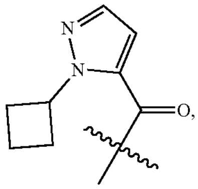,
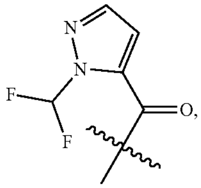,
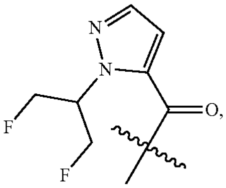,
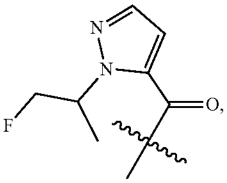,
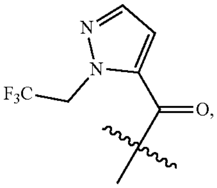,
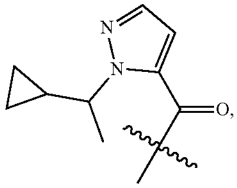,
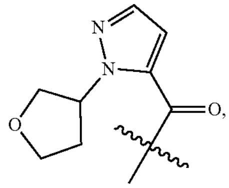,
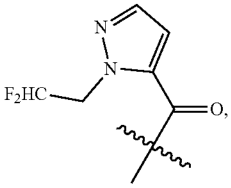,
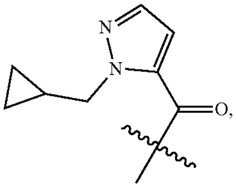,
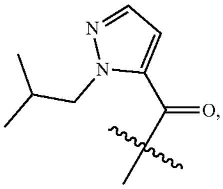,
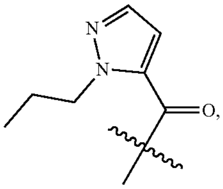,
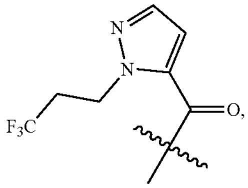,
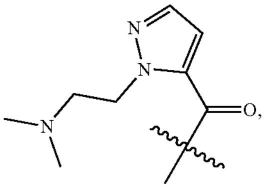,
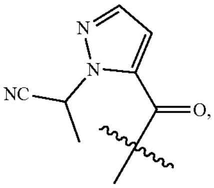,
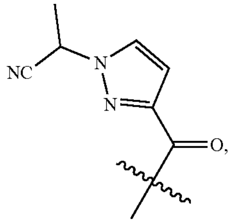,
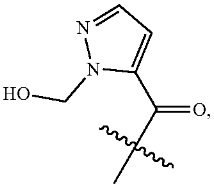,
-continued
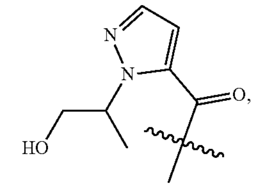,
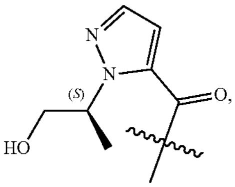,
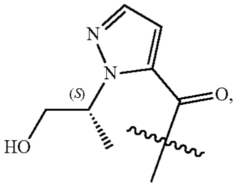,
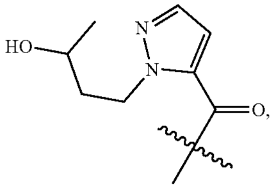,
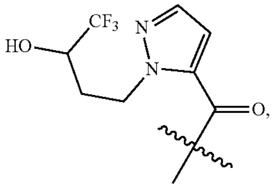,
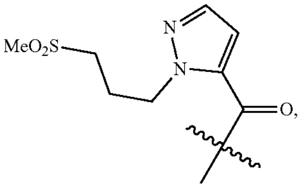,
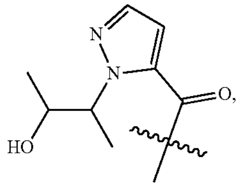,
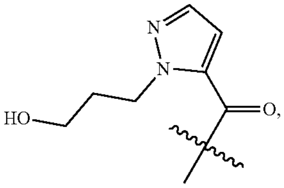,
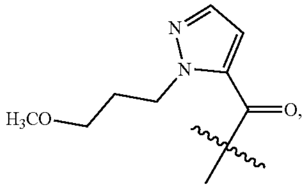,
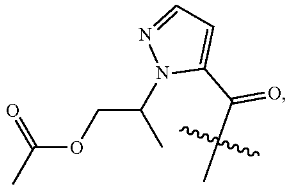,
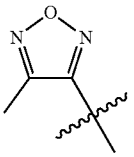,
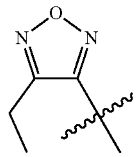,
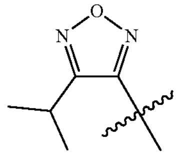,
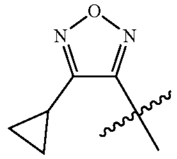,
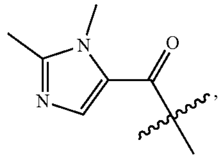,
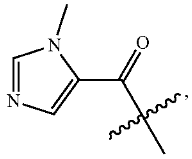,
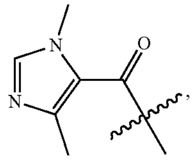, -continued
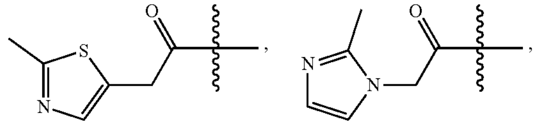
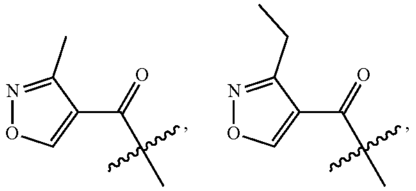
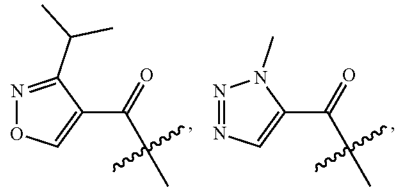
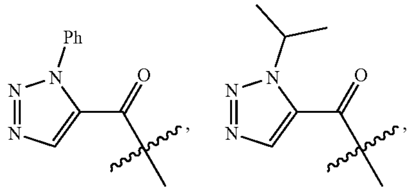
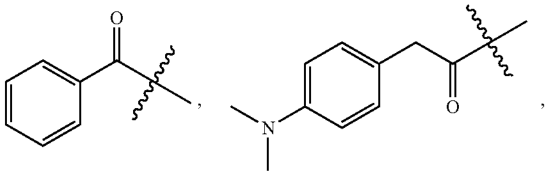
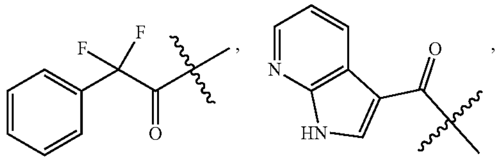
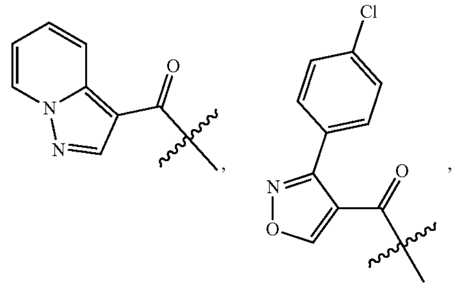
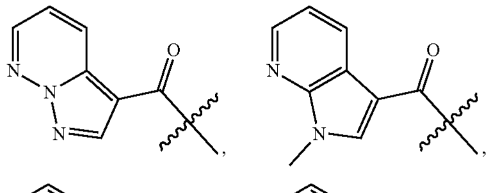
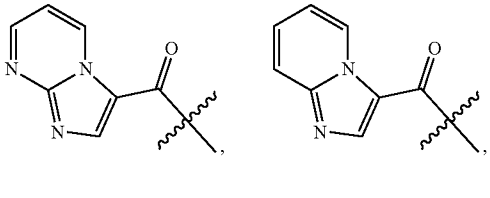
-continued
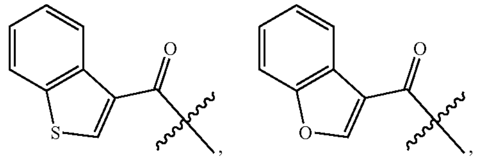
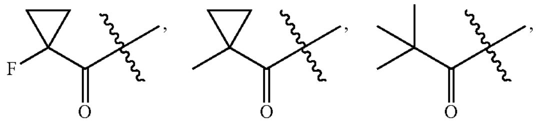
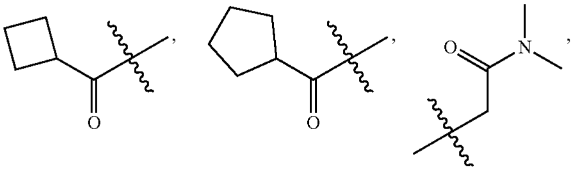
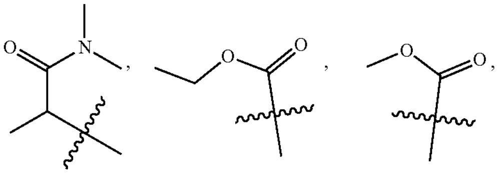
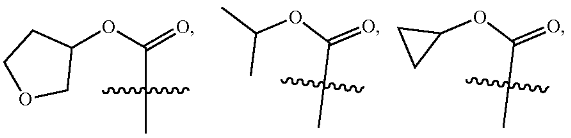
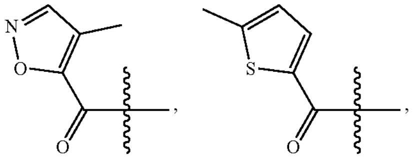
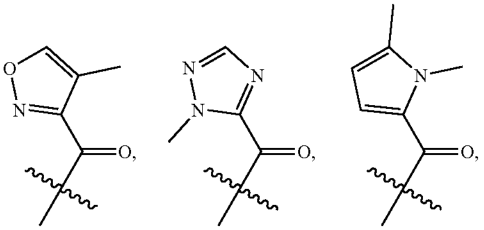
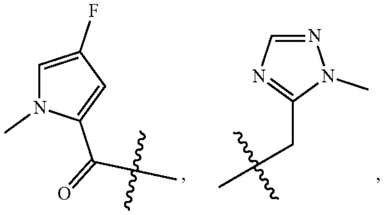
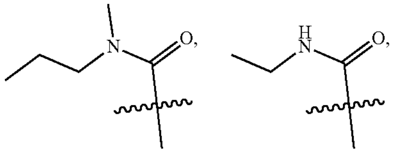
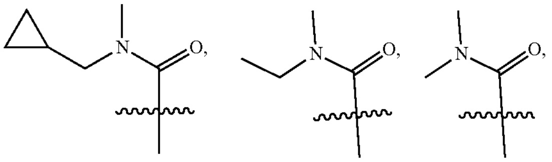

-continued

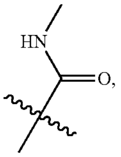
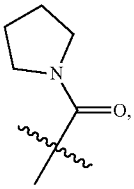
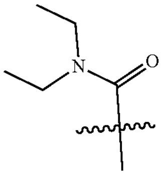
,
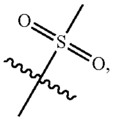
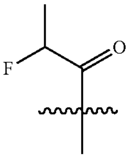
,
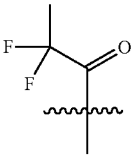
,
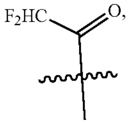
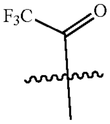
and
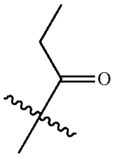
.

In an embodiment, the A ring is selected from the group consisting of 3-membered cycloalkyl, 4-membered cycloalkyl, 5-membered cycloalkyl, 6-membered cycloalkyl, 7-membered cycloalkyl, 8-membered cycloalkyl, 5-membered heteroaromatic ring, 5- to 12-membered spiro ring, 5- to 12-membered bridged ring,

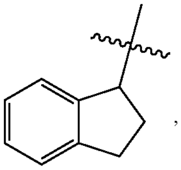
,
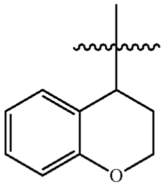
and
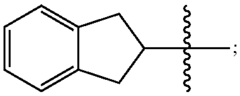
;

wherein cycloalkyl, heteroaromatic ring, spiro ring, bridged ring,

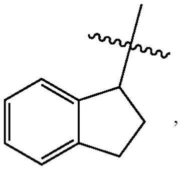
,
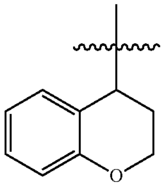
and
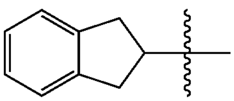

are independently unsubstituted or substituted with 1, 2 or 3 $R^{A1}$ groups.

In some embodiments, the A ring is selected from the group consisting of

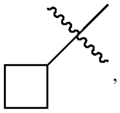
,
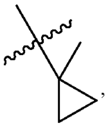
,
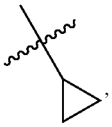
,
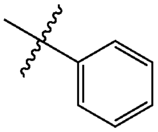
and
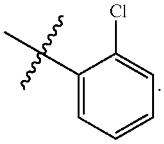
.

In an embodiment, the B ring is selected from the group consisting of 3-membered cycloalkyl, 4-membered cycloalkyl, 5-membered cycloalkyl, 6-membered cycloalkyl, 7-membered cycloalkyl, 8-membered cycloalkyl, 5-membered heteroaromatic ring, 5- to 12-membered spiro ring, 5- to 12-membered bridged ring,

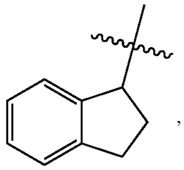
,
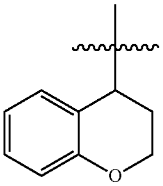
and
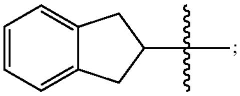
;

wherein cycloalkyl, heteroaromatic ring, spiro ring, bridged ring,

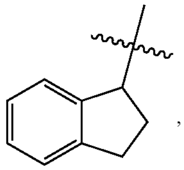
,
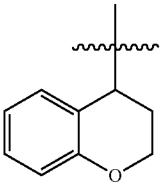
and
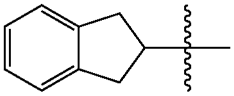

are independently unsubstituted or substituted with 1, 2 or 3 $R^{B1}$ groups.

In some embodiments, the B ring is selected from the group consisting of

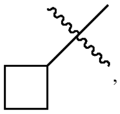
,
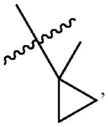 [SMILES: *C1(C)CC1]
,
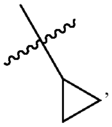 [SMILES: *C1CC1]
,
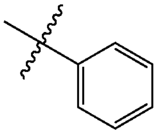
and
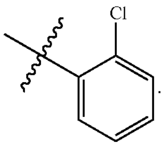
.

In some embodiments, the A ring is

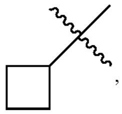
, and the B ring is

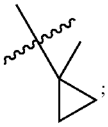
;

or A ring is

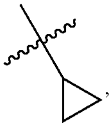
, and the B ring is

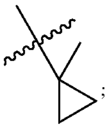 [SMILES: *C1(C)CC1]
;

or A ring is

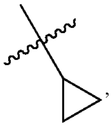 [SMILES: *C1CC1]
, and the B ring is

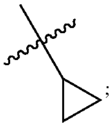 [SMILES: *C1CC1]
;

or A ring is

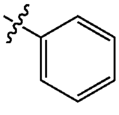
, and the B ring is

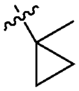
;

or A ring is

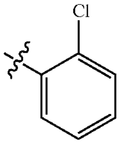

and the B ring is

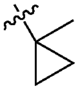
.

In an embodiment, the C ring is substituted or unsubstituted 5- to 6-membered heteroaromatic ring; wherein the substituted 5- to 6-membered heteroaromatic ring comprises 1-3 $R^{C1}$ substituents independently selected from the group consisting of hydrogen, halogen, cyano, =O, nitro, —$C_{1-6}$ alkyl, halogen-substituted-$C_{1-6}$ alkyl, —$OR^{C2}$, —$C(O)R^{C2}$, —$C(O)NR^{C2}R^{C3}$, —$NR^{C2}R^{C3}$, —$NR^{C2}C(O)R^{C3}{}_2$, 3- to 6-membered cycloalkyl and 3- to 6-membered heterocycloalkyl.

In some embodiments, the C ring is selected from the group consisting of

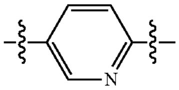
,
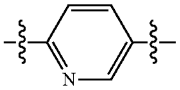
,
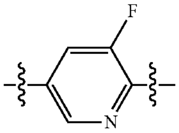
,
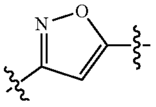
and
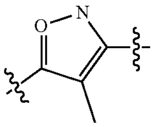
.

In an embodiment, the C ring is selected from the group consisting of

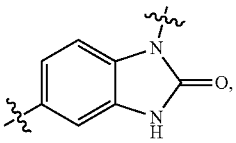
,
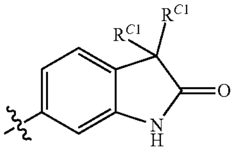

-continued and

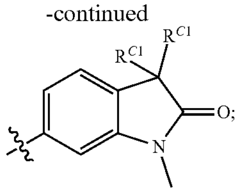

wherein two $R^{C1}$ groups are independent or linked to form 3- to 10-membered cycloalkyl or 3- to 10-membered heterocycloalkyl.

In some embodiments, the C ring is selected from the group consisting of

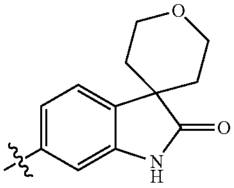

and

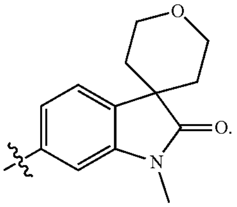

In some embodiments, the C ring is selected from the group consisting of

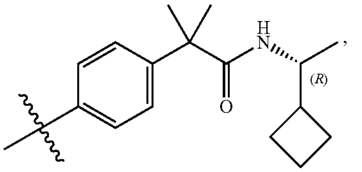

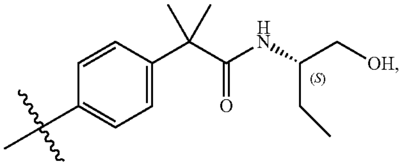

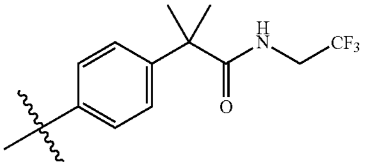

and

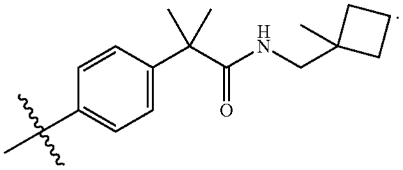

In an embodiment, the D ring is 5- to 6-membered cycloalkyl, 5- to 6-membered heterocycloalkyl, benzene ring or 5- to 6-membered heteroaromatic ring, or absent; wherein cycloalkyl, heterocycloalkyl, benzene ring, heteroaromatic ring are independently unsubstituted or substituted with 1, 2 or 3 $R^{D1}$ groups.

In some embodiments, the D ring is selected from the group consisting of

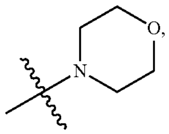
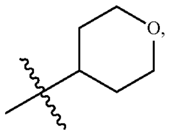
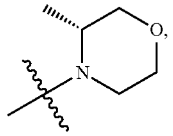
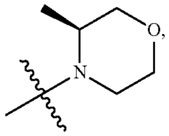
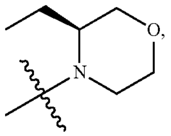
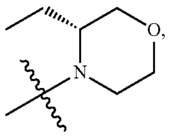
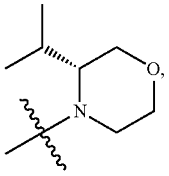
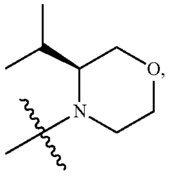
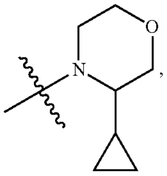
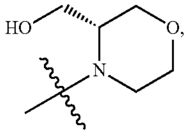
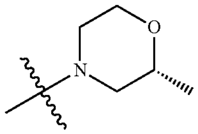
,
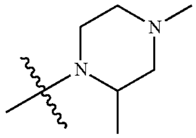
,
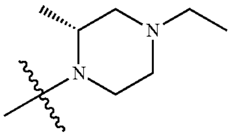
,
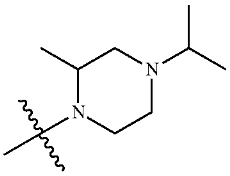
,
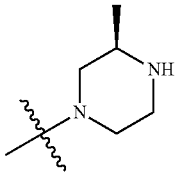
and
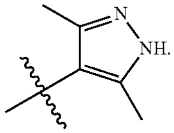

In some embodiments, the D ring is selected from the group consisting of

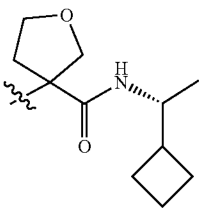
,
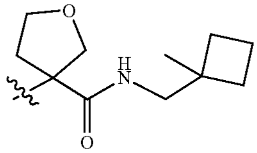
,

-continued

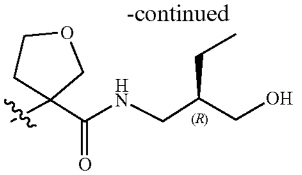

and

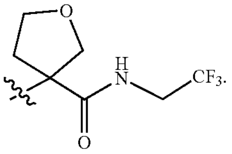

In an embodiment, the C ring is substituted or unsubstituted benzene ring; wherein the substituted benzene ring comprises 1-3 $R^{C1}$ substituents independently selected from the group consisting of hydrogen, $C_{1-6}$ alkyl, halogen-substituted $C_{1-6}$ alkyl, halogen and cyano;

the L is absent; and the D ring is 3- to 10-membered cycloalkyl, 3- to 10-membered heterocycloalkyl, 5- to 10-membered aromatic ring, 7- to 10-membered heteroaromatic ring, 5- to 12-membered spiro ring, 5- to 12-membered spiro heterocycle, 5- to 12-membered bridged ring or 5- to 12-membered bridged heterocycle, or absent; wherein cycloalkyl, heterocycloalkyl, aromatic ring, heteroaromatic ring, spiro ring, spiro heterocycle, bridged ring and bridged heterocycle are independently unsubstituted or substituted with 1, 2, or 3 $R^{D1}$ groups.

In an embodiment, the compound is shown in formula (II):

(II)

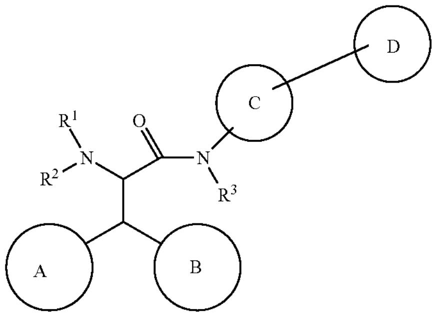

;

wherein $R^1$ is selected from the group consisting of —C(O)$R^{11}$, —C(O)$NR^{11}R^{12}$, —C(O)$OR^{11}$, —S(O)$R^{11}$, —S(O)$NR^{11}R^{12}$, —S(O)$OR^{11}$, —$S(O)_2R^{11}$, —$S(O)_2NR^{11}R^{12}$, —$S(O)_2OR^{11}$, —P(O)$R^{11}R^{12}$, —P(O)($OR^{11}$) $R^{12}$ and —P(O)($OR^{11}$)($OR^{12}$);

$R^{11}$ and $R^{12}$ are independently selected from the group consisting of hydrogen, $C_{1-6}$ alkyl, halogen-substituted $C_{1-6}$ alkyl, —$C_{0-2}$ alkylene-(3- to 10-membered cycloalkyl), —$C_{0-2}$ alkylene-(3- to 10-membered heterocycloalkyl), —$C_{0-2}$ alkylene-(5- to 10-membered aromatic ring), —$C_{0-2}$ alkylene-(5- to 10-membered heteroaromatic ring); wherein alkyl, alkylene, cycloalkyl, heterocycloalkyl, aromatic ring and heteroaromatic ring are independently unsubstituted or substituted with 1, 2 or 3 $R^{1a}$ groups;

the $R^{1a}$ groups are each independently selected from the group consisting of hydrogen, halogen, cyano, =O, nitro, —$C_{1-6}$ alkyl, halogen-substituted-$C_{1-6}$ alkyl, —$C_{0-2}$ alkylene-$OR^{1b}$, —$C_{0-2}$ alkylene-C(O)$R^{1b}$, —$C_{0-2}$ alkylene-C(O)$NR^{1b}R^{1c}$, —$C_{0-2}$ alkylene-$NR^{1b}R^{1c}$, —$C_{0-2}$ alkylene-$NR^{1b}$C(O)$R^{1c}$, —$C_{0-4}$ alkylene-$S(O)_2R^{1b}R^{1c}$, —$C_{0-2}$ alkylene-(3- to 10-membered cycloalkyl), —$C_{0-2}$ alkylene-(3- to 10-membered heterocycloalkyl), —$C_{0-2}$ alkylene-(5- to 10-membered aromatic ring), —$C_{0-2}$ alkylene-(5- to 10-membered heteroaromatic ring); wherein alkyl, alkylene, cycloalkyl, heterocycloalkyl, aromatic ring and heteroaromatic ring are independently unsubstituted or substituted with 1, 2 or 3 $R^{1b}$ groups;

$R^{1b}$ and $R^{1c}$ are independently selected from the group consisting of hydrogen, $C_{1-6}$ alkyl, halogen-substituted $C_{1-6}$ alkyl, halogen, cyano, =O, nitro, —OH, —O($C_{1-6}$ alkyl), —$NH_2$, —NH($C_{1-6}$ alkyl) and —N($C_{1-6}$ alkyl) ($C_{1-6}$ alkyl);

$R^2$ and $R^3$ are independently selected from the group consisting of hydrogen, —$C_{1-6}$ alkyl and —$C_{0-2}$ alkylene-(3- to 10-membered cycloalkyl);

the A ring is selected from the group consisting of 3- to 10-membered cycloalkyl, 3- to 10-membered heterocycloalkyl, 5- to 10-membered aromatic ring, 5- to 10-membered heteroaromatic ring, 5- to 12-membered spiro ring, 5- to 12-membered spiro heterocycle, 5- to 12-membered bridged ring, 5- to 12-membered bridged heterocycle; wherein cycloalkyl, heterocycloalkyl, aromatic ring, heteroaromatic ring, spiro ring, spiro heterocycle, bridged ring and bridged heterocycle are independently unsubstituted or substituted with 1, 2 or 3 $R^{A1}$ groups;

the $R^{A1}$ groups are each independently selected from the group consisting of hydrogen, $C_{1-6}$ alkyl, halogen-substituted $C_{1-6}$ alkyl, halogen, cyano, =O, nitro, —OH, —O($C_{1-6}$ alkyl), —$NH_2$, —NH($C_{1-6}$ alkyl), —N($C_{1-6}$ alkyl) ($C_{1-6}$ alkyl), —$C_{0-2}$ alkylene-(3- to 10-membered cycloalkyl), —$C_{0-2}$ alkylene-(3- to 10-membered heterocycloalkyl), —$C_{0-2}$ alkylene-(5- to 10-membered aromatic ring) and —$C_{0-2}$ alkylene-(5- to 10-membered heteroaromatic ring);

the B ring is selected from the group consisting of 3- to 10-membered cycloalkyl, 3- to 10-membered heterocycloalkyl, 5- to 10-membered aromatic ring, 5- to 10-membered heteroaromatic ring, 5- to 12-membered spiro ring, 5- to 12-membered spiro heterocycle, 5- to 12-membered bridged ring, 5- to 12-membered bridged heterocycle; wherein cycloalkyl, heterocycloalkyl, aromatic ring, heteroaromatic ring, spiro ring, spiro heterocycle, bridged ring and bridged heterocycle are independently unsubstituted or substituted with 1, 2 or 3 $R^{B1}$ groups;

the $R^{B1}$ groups are each independently selected from the group consisting of hydrogen, $C_{1-6}$ alkyl, halogen-substituted $C_{1-6}$ alkyl, halogen, cyano, =O, nitro, —OH, —O($C_{1-6}$ alkyl), —$NH_2$, —NH($C_{1-6}$ alkyl), —N($C_{1-6}$ alkyl) ($C_{1-6}$ alkyl), —$C_{0-2}$ alkylene-(3- to 10-membered cycloalkyl), —$C_{0-2}$ alkylene-(3- to 10-membered heterocycloalkyl), —$C_{0-2}$ alkylene-(5- to 10-membered aromatic ring) and —$C_{0-2}$ alkylene-(5- to 10-membered heteroaromatic ring);

the C ring is substituted or unsubstituted 5- to 6-membered heteroaromatic ring; wherein the substituted 5- to 6-membered heteroaromatic ring comprises 1-4 $R^{C1}$ substituents independently selected from the group consisting of hydrogen, halogen, cyano, =O, nitro, —$C_{1-6}$ alkyl, halogen-substituted-$C_{1-6}$ alkyl, —$C_{0-2}$ alkylene-$OR^{C2}$, —$C_{0-2}$ alkylene-C(O)$R^{C2}$, —$C_{0-2}$ alkylene-C(O)$NR^{C2}R^{C3}$, —$C_{0-2}$ alkylene-$NR^{C2}R^{C3}$, —$C_{0-2}$ alkylene-$NR^{C2}$C(O)$R^{C3}{}_2$, 3- to 10-membered cycloalkyl and 3- to 10-membered heterocycloalkyl; wherein alkyl and alkylene are independently unsubstituted or substituted with 1, 2 or 3 $R^{C4}$ groups;

the $R^{C2}$ and $R^{C3}$ are independently selected from the group consisting of hydrogen, —$C_{1-6}$ alkyl, —$C_{0-2}$ alkylene-$OR^{C4}$, —$C_{0-2}$ alkylene-(3- to 10-membered cycloalkyl), —$C_{0-2}$ alkylene-(3- to 10-membered heterocycloalkyl); wherein alkyl, alkylene and cycloalkyl are independently unsubstituted or substituted with 1, 2 or 3 $R^{C4}$ groups;

the $R^{C4}$ groups are each independently selected from the group consisting of hydrogen, $C_{1-6}$ alkyl, halogen-substituted $C_{1-6}$ alkyl, halogen, cyano, =O, nitro, —OH, —O($C_{1-6}$ alkyl), —$NH_2$, —NH($C_{1-6}$ alkyl) and —N($C_{1-6}$ alkyl) ($C_{1-6}$ alkyl);

the D ring is selected from the group consisting of 3- to 10-membered cycloalkyl, 3- to 10-membered heterocycloalkyl, 5- to 10-membered aromatic ring, 5- to 10-membered heteroaromatic ring, 5- to 12-membered spiro ring, 5- to 12-membered spiro heterocycle, 5- to 12-membered bridged ring and 5- to 12-membered bridged heterocycle; wherein cycloalkyl, heterocycloalkyl, aromatic ring, heteroaromatic ring, spiro ring, spiro heterocycle, bridged ring and bridged heterocycle are independently unsubstituted or substituted with 1, 2 or 3 $R^{D1}$ groups;

the $R^{D1}$ groups are each independently selected from the group consisting of hydrogen, halogen, cyano, =O, nitro, —$C_{1-6}$ alkyl, halogen-substituted-$C_{1-6}$ alkyl, —$C_{0-2}$ alkylene-$OR^{D2}$, —$C_{0-2}$ alkylene-C(O)$R^{D2}$, —$C_{0-2}$ alkylene-C(O)$NR^{D2}R^{D3}$, —$C_{0-2}$ alkylene-$NR^{D2}R^{D3}$, —$C_{0-2}$ alkylene-$NR^{D2}$C(O)$R^{D3}$, —$C_{0-4}$ alkylene-OP(O)$(OH)_2$, —$C_{0-2}$ alkylene-(3- to 10-membered cycloalkyl), —$C_{0-2}$ alkylene-(3- to 10-membered heterocycloalkyl), —$C_{0-2}$ alkylene-(5- to 10-membered aromatic ring) and —$C_{0-2}$ alkylene-(5- to 10-membered heteroaromatic ring); wherein alkyl, alkylene, cycloalkyl, heterocycloalkyl, aromatic ring and heteroaromatic ring are independently unsubstituted or substituted with 1, 2 or 3 $R^{D4}$ groups;

$R^{D2}$ and $R^{D3}$ are independently selected from the group consisting of hydrogen, $C_{1-6}$ alkyl, —$C_{0-2}$ alkylene-$OR^{D4}$, —$C_{0-2}$ alkylene-(3- to 10-membered cycloalkyl), —$C_{0-2}$ alkylene-(3- to 10-membered heterocycloalkyl), —$C_{0-2}$ alkylene-(5- to 10-membered aromatic ring) and —$C_{0-2}$ alkylene-(5- to 10-membered heteroaromatic ring); wherein alkyl, alkylene, cycloalkyl, heterocycloalkyl, aromatic ring, heteroaromatic ring are independently unsubstituted or substituted with 1, 2 or 3 $R^{D4}$ groups; and The $R^{D4}$ groups are each independently selected from the group consisting of hydrogen, $C_{1-6}$ alkyl, halogen-substituted $C_{1-6}$ alkyl, halogen, cyano, =O, nitro, —OH, —O($C_{1-6}$ alkyl), —$NH_2$, —NH($C_{1-6}$ alkyl), —N($C_{1-6}$ alkyl) ($C_{1-6}$ alkyl), —$C_{0-2}$ alkylene-(3- to 10-membered cycloalkyl), —$C_{0-2}$ alkylene-(3- to 10-membered heterocycloalkyl), —$C_{0-2}$ alkylene-(5- to 10-membered aromatic ring) and —$C_{0-2}$ alkylene-(5- to 10-membered heteroaromatic ring).

In an embodiment, $R^1$ is —C(O)$R^{11}$; $R^{11}$ is selected from the group consisting of

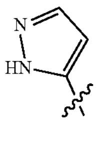 , 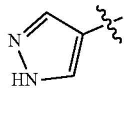 , 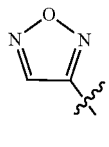 ,

-continued

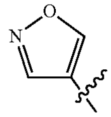 , 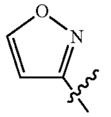 and 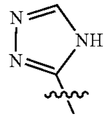 ;

wherein

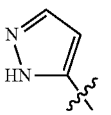 , 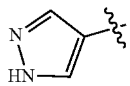 , 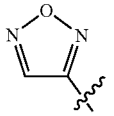 ,

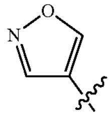 , 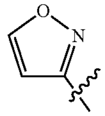 and 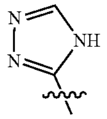

are independently unsubstituted or substituted with 1, 2 or 3 $R^{1a}$ groups; the $R^{1a}$ groups are each independently selected from the group consisting of hydrogen, halogen, cyano, —$C_{1-6}$ alkyl, halogen-substituted-$C_{1-6}$ alkyl, 3- to 6-membered cycloalkyl and —$C_{0-2}$ alkylene-$OR^{1b}$, wherein $R^{1b}$ is selected from the group consisting of hydrogen, $C_{1-6}$ alkyl and halogen-substituted $C_{1-6}$ alkyl;

$R^2$ and $R^3$ are independently selected from the group consisting of hydrogen and —$C_{1-6}$ alkyl;

the A ring is selected from the group consisting of:

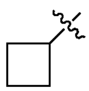 , 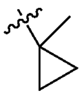 , 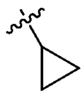 ,

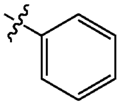 and 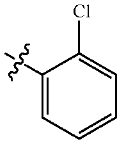 ;

the B ring is selected from the group consisting of:

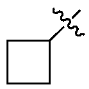 , 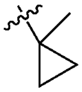 , 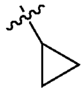 ,

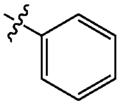 and 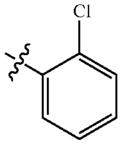 ;

the C ring is selected from the group consisting of:

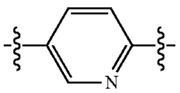 , 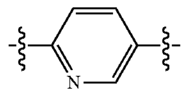 ,

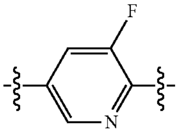 , 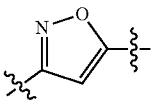 and

-continued

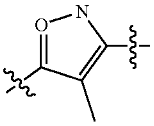

;

and the D ring is selected from the group consisting of:

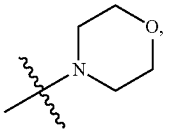
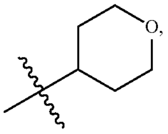
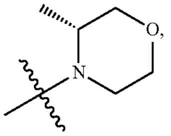
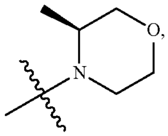
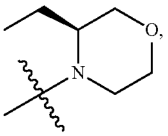
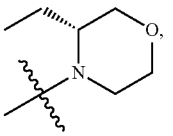
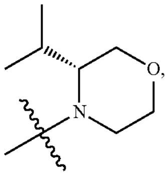
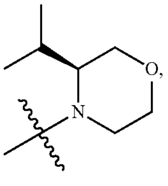
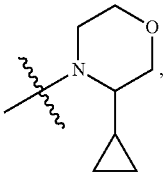

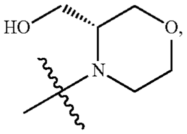
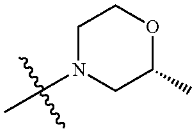
,

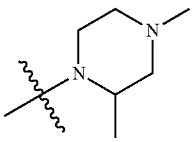
,
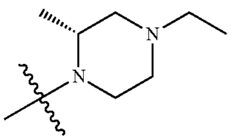
,

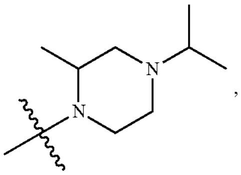
,
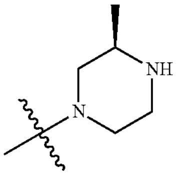
and

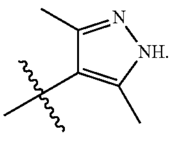

In an embodiment, the compound is shown in formula (III):

(III)

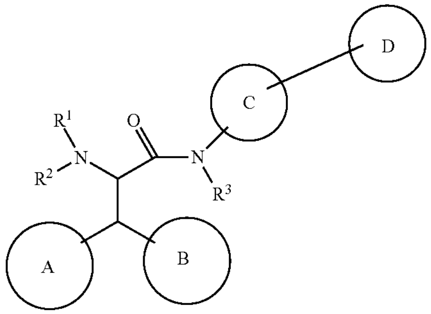

;

wherein $R^1$ is selected from the group consisting of —C(O)$R^{11}$, —C(O)N$R^{11}R^{12}$, —C(O)O$R^{11}$, —S(O)$R^{11}$, —S(O)N$R^{11}R^{12}$, —S(O)O$R^{11}$, —S(O)$_2R^{11}$, —S(O)$_2$N$R^{11}R^{12}$, —S(O)$_2$O$R^{11}$, —P(O)$R^{11}R^{12}$, —P(O)(O$R^{11}$) $R^{12}$ and —P(O)(O$R^{11}$)(O$R^{12}$);

$R^{11}$ and $R^{12}$ are independently selected from the group consisting of hydrogen, $C_{1-6}$ alkyl, halogen-substituted $C_{1-6}$ alkyl, —$C_{0-2}$ alkylene-(3- to 10-membered cycloalkyl), —$C_{0-2}$ alkylene-(3- to 10-membered heterocycloalkyl), —$C_{0-2}$ alkylene-(5- to 10-membered aromatic ring) and —$C_{0-2}$ alkylene-(5- to 10-membered heteroaromatic ring); wherein alkyl, alkylene, cycloalkyl, heterocycloalkyl and aromatic ring, heteroaromatic ring are independently unsubstituted or substituted with 1, 2 or 3 $R^{1a}$ groups;

the $R^{1a}$ groups are each independently selected from the group consisting of hydrogen, halogen, cyano, ═O, nitro, —$C_{1-6}$ alkyl, halogen-substituted-$C_{1-6}$ alkyl, —$C_{0-2}$ alkylene-O$R^{1b}$, —$C_{0-2}$ alkylene-C(O)$R^{1b}$, —$C_{0-2}$ alkylene-C(O)N$R^{1b}R^{1c}$, —$C_{0-2}$ alkylene-N$R^{1b}R^{1c}$, —$C_{0-2}$ alkylene-N$R^{1b}$C(O)$R^{1c}$, —$C_{0-4}$ alkylene-S(O)$_2R^{1b}R^{1c}$, —$C_{0-2}$ alkylene-(3- to 10-membered cycloalkyl), —$C_{0-2}$ alkylene-(3- to 10-membered heterocycloalkyl), —$C_{0-2}$ alkylene-(5- to 10-membered aromatic ring) and —$C_{0-2}$ alkylene-(5- to 10-membered heteroaromatic ring); wherein alkyl, alkylene, cycloalkyl, heterocycloalkyl, aromatic ring and heteroaromatic ring are independently unsubstituted or substituted with 1, 2 or 3 $R^{1b}$ groups;

$R^{1b}$ and $R^{1c}$ are independently selected from the group consisting of hydrogen, $C_{1-6}$ alkyl, halogen-substituted $C_{1-6}$ alkyl, halogen, cyano, ═O, nitro, —OH, —O($C_{1-6}$ alkyl), —$NH_2$, —NH($C_{1-6}$ alkyl) and —N($C_{1-6}$ alkyl)($C_{1-6}$ alkyl);

$R^2$ and $R^3$ are independently selected from the group consisting of hydrogen, —$C_{1-6}$ alkyl and —$C_{0-2}$ alkylene-(3- to 10-membered cycloalkyl);

the A ring is selected from the group consisting of 3- to 10-membered cycloalkyl, 3- to 10-membered heterocycloalkyl, 5- to 10-membered aromatic ring, 5- to 10-membered heteroaromatic ring, 5- to 12-membered spiro ring, 5- to 12-membered spiro heterocycle, 5- to 12-membered bridged ring and 5- to 12-membered bridged heterocycle; wherein cycloalkyl, heterocycloalkyl, aromatic ring, heteroaromatic ring, spiro ring, spiro heterocycle, bridged ring and bridged heterocycle are independently unsubstituted or substituted with 1, 2 or 3 $R^{A1}$ groups;

the $R^{A1}$ groups are independently selected from the group consisting of hydrogen, $C_{1-6}$ alkyl, halogen-substituted $C_{1-6}$ alkyl, halogen, cyano, =O, nitro, —OH, —O($C_{1-6}$ alkyl), —$NH_2$, —NH($C_{1-6}$ alkyl), —N($C_{1-6}$ alkyl) ($C_{1-6}$ alkyl), —$C_{0-2}$ alkylene-(3- to 10-membered cycloalkyl), —$C_{0-2}$ alkylene-(3- to 10-membered heterocycloalkyl), —$C_{0-2}$ alkylene-(5- to 10-membered aromatic ring) and —$C_{0-2}$ alkylene-(5- to 10-membered heteroaromatic ring);

the B ring is selected from the group consisting of 3- to 10-membered cycloalkyl, 3- to 10-membered heterocycloalkyl, 5- to 10-membered aromatic ring, 5- to 10-membered heteroaromatic ring, 5- to 12-membered spiro ring, 5- to 12-membered spiro heterocycle, 5- to 12-membered bridged ring and 5- to 12-membered bridged heterocycle; wherein cycloalkyl, heterocycloalkyl, aromatic ring, heteroaromatic ring, spiro ring, spiro heterocycle, bridged ring and bridged heterocycle are independently unsubstituted or substituted with 1, 2 or 3 $R^{B1}$ groups;

the $R^{B1}$ groups are independently selected from the group consisting of hydrogen, $C_{1-6}$ alkyl, halogen-substituted $C_{1-6}$ alkyl, halogen, cyano, =O, nitro, —OH, —O($C_{1-6}$ alkyl), —$NH_2$, —NH($C_{1-6}$ alkyl), —N($C_{1-6}$ alkyl) ($C_{1-6}$ alkyl), —$C_{0-2}$ alkylene-(3- to 10-membered cycloalkyl), —$C_{0-2}$ alkylene-(3- to 10-membered heterocycloalkyl), —$C_{0-2}$ alkylene-(5- to 10-membered aromatic ring) and —$C_{0-2}$ alkylene-(5- to 10-membered heteroaromatic ring);

the C ring is selected from the group consisting of 6-membered aromatic ring and 5- to 6-membered heteroaromatic ring; wherein the aromatic ring and heteroaromatic ring are independently unsubstituted or substituted with 1, 2, 3 or 4 $R^{C1}$ groups;

the $R^{C1}$ groups are independently selected from the group consisting of hydrogen, halogen, cyano, =O, nitro, —$C_{1-6}$ alkyl, halogen-substituted-$C_{1-6}$ alkyl, —$C_{0-2}$ alkylene-$OR^{C2}$, —$C_{0-2}$ alkylene-C(O)$R^{C2}$, —$C_{0-2}$ alkylene-C(O)$NR^{C2}R^{C3}$, —$C_{0-2}$ alkylene-$NR^{C2}R^{C3}$, —$C_{0-2}$ alkylene-$NR^{C2}$C(O)$R^{C3}{}_2$, 3- to 10-membered cycloalkyl and 3- to 10-membered heterocycloalkyl; wherein alkyl and alkylene are independently unsubstituted or substituted with 1, 2 or 3 $R^{C4}$ groups.

$R^{C2}$ and $R^{C3}$ are independently selected from the group consisting of hydrogen, —$C_{1-6}$ alkyl, —$C_{0-2}$ alkylene-$OR^{C4}$, —$C_{0-2}$ alkylene-(3- to 10-membered cycloalkyl) and —$C_{0-2}$ alkylene-(3- to 10-membered heterocycloalkyl); wherein alkyl, alkylene and cycloalkyl are independently unsubstituted or substituted with 1, 2 or 3 $R^{C4}$ groups;

the $R^{C4}$ groups are independently selected from the group consisting of hydrogen, $C_{1-6}$ alkyl, halogen-substituted $C_{1-6}$ alkyl, halogen, cyano, =O, nitro, —OH, —O($C_{1-6}$ alkyl), —$NH_2$, —NH($C_{1-6}$ alkyl) and —N($C_{1-6}$ alkyl) ($C_{1-6}$ alkyl); and the D ring is selected from the group consisting of 3- to 10-membered cycloalkyl, 3- to 10-membered heterocycloalkyl, 5- to 10-membered aromatic ring, 5- to 12-membered spiro ring, 5- to 12-membered spiro heterocycle, 5- to 12-membered bridged ring and 5- to 12-membered bridged heterocycle; wherein cycloalkyl, heterocycloalkyl, aromatic ring, heteroaromatic ring, spiro ring, spiro heterocycle, bridged ring, bridged heterocycle are independently unsubstituted or substituted with 1, 2 or 3 $R^{D1}$ groups;

the $R^{D1}$ groups are independently selected from the group consisting of hydrogen, halogen, cyano, =O, nitro, —$C_{1-6}$ alkyl, halogen-substituted-$C_{1-6}$ alkyl, —$C_{0-2}$ alkylene-$OR^{D2}$, —$C_{0-2}$ alkylene-C(O)$R^{D2}$, —$C_{0-2}$ alkylene-C(O)$NR^{D2}R^{D3}$, —$C_{0-2}$ alkylene-$NR^{D2}R^{D3}$, —$C_{0-2}$ alkylene-$NR^{D2}$C(O)$R^{D3}$, —$C_{0-4}$ alkylene-OP (O)(OH) 2, —$C_{0-2}$ alkylene-(3- to 10-membered cycloalkyl), —$C_{0-2}$ alkylene-(3- to 10-membered heterocycloalkyl), —$C_{0-2}$ alkylene-(5- to 10-membered aromatic ring) and —$C_{0-2}$ alkylene-(5- to 10-membered heteroaromatic ring); wherein alkyl, alkylene, cycloalkyl, heterocycloalkyl, aromatic ring and heteroaromatic ring are independently unsubstituted or substituted with 1, 2 or 3 $R^{D4}$ groups;

$R^{D2}$ and $R^{D3}$ are independently selected from the group consisting of hydrogen, $C_{1-6}$ alkyl, —$C_{0-2}$ alkylene-$OR^{D4}$, —$C_{0-2}$ alkylene-(3- to 10-membered cycloalkyl), —$C_{0-2}$ alkylene-(3- to 10-membered heterocycloalkyl), —$C_{0-2}$ alkylene-(5- to 10-membered aromatic ring) and —$C_{0-2}$ alkylene-(5- to 10-membered heteroaromatic ring); wherein alkyl, alkylene, cycloalkyl, heterocycloalkyl, aromatic ring and heteroaromatic ring are independently unsubstituted or substituted with 1, 2 or 3 $R^{D4}$ groups; and the $R^{D4}$ groups are each independently selected from the group consisting of hydrogen, $C_{1-6}$ alkyl, halogen-substituted $C_{1-6}$ alkyl, halogen, cyano, =O, nitro, —OH, —O($C_{1-6}$ alkyl), —$NH_2$, —NH($C_{1-6}$ alkyl), —N($C_{1-6}$ alkyl) ($C_{1-6}$ alkyl), —$C_{0-2}$ alkylene-(3- to 10-membered cycloalkyl), —$C_{0-2}$ alkylene-(3- to 10-membered heterocycloalkyl), —$C_{0-2}$ alkylene-(5- to 10-membered aromatic ring) and —$C_{0-2}$ alkylene-(5- to 10-membered heteroaromatic ring).

In an embodiment, $R^1$ is —C(O)$R^{11}$; $R^{11}$ is selected from the group consisting of:

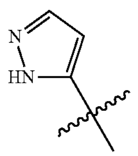, 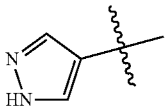, 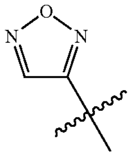, 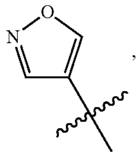, 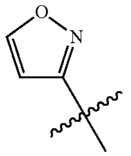 and 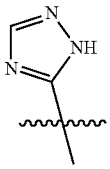;

wherein

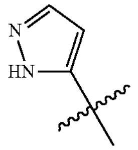, 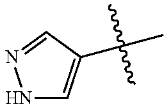, 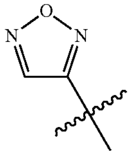, 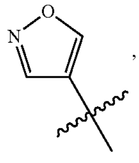, 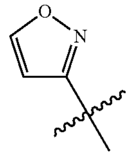 and 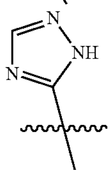

are independently unsubstituted or substituted with 1, 2 or 3 $R^{1a}$ groups; the $R^{1a}$ groups are each independently selected from the group consisting of hydrogen, halogen, cyano, —$C_{1-6}$ alkyl, halogen-substituted-$C_{1-6}$ alkyl, 3- to 6-membered cycloalkyl and —$C_{0-2}$ alkylene-$OR^{1b}$; wherein $R^{1b}$ is selected from the group consisting of hydrogen, $C_{1-6}$ alkyl and halogen-substituted $C_{1-6}$ alkyl;

$R^2$ and $R^3$ are independently selected from the group consisting of hydrogen and —$C_{1-6}$ alkyl;

the A ring is selected from the group consisting of

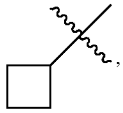, 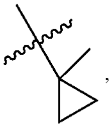, 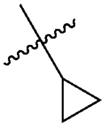, 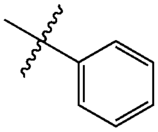 and 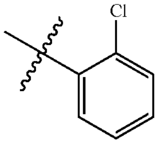;

the B ring is selected from the group consisting of

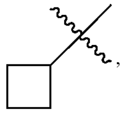, 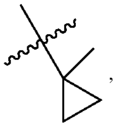, 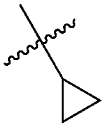, 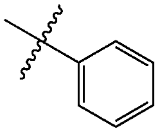 and 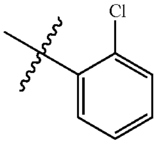;

the C ring is selected from the group consisting of

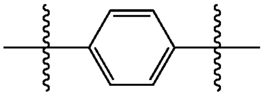, 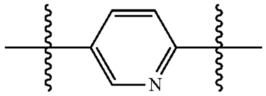, 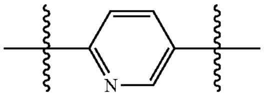, 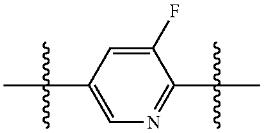, 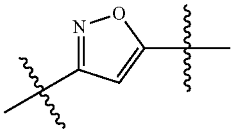 and 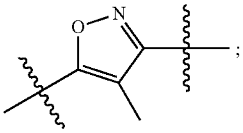;

and the D ring is selected from the group consisting of

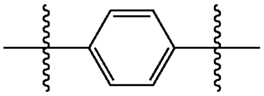, 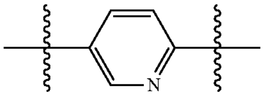, 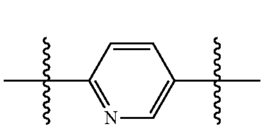, 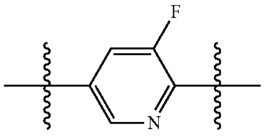,

-continued

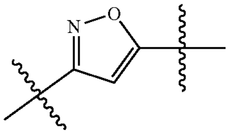 and 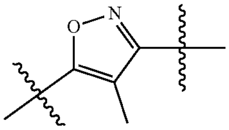.

In an embodiment, the compound is shown in formula (IV):

(IV)

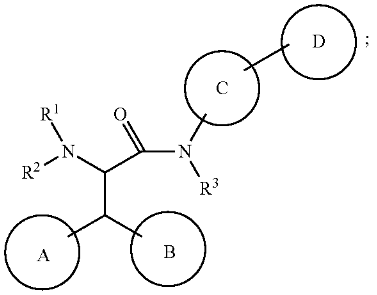;

wherein $R^1$ is —$C(O)R^{11}$; $R^{11}$ is selected from the group consisting of

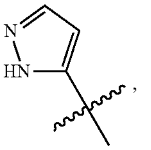, 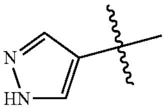, 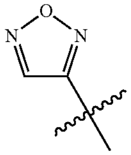, 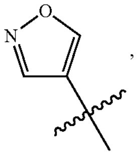, 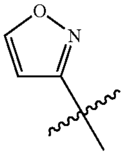 and 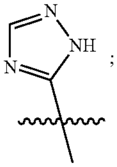;

wherein

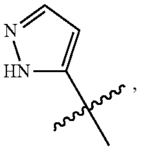, 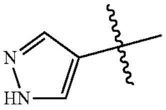, 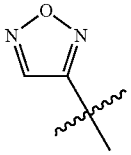, 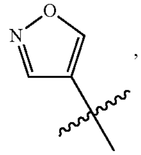, 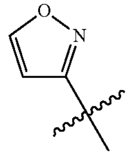 and 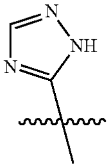

are independently unsubstituted or substituted with 1, 2 or 3 $R^{1a}$ groups; the $R^{1a}$ groups are each independently selected from the group consisting of hydrogen, halogen, cyano, —$C_{1-6}$ alkyl, halogen-substituted —$C_{1-6}$ alkyl, 3- to 6-membered cycloalkyl and —$C_{0-2}$ alkylene-$OR^{1b}$; wherein $R^{1b}$ is selected from the group consisting of hydrogen, $C_{1-6}$ alkyl and halogen-substituted $C_{1-6}$ alkyl;

$R^2$ and $R^3$ are independently selected from the group consisting of hydrogen and —$C_{1-6}$ alkyl;

the A ring is selected from the group consisting of

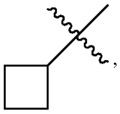, 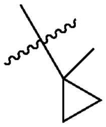, 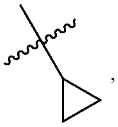, 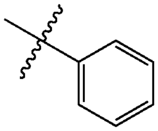 and 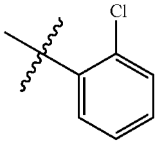;

the B ring is selected from the group consisting of

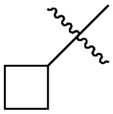, 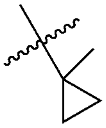, 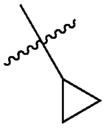, 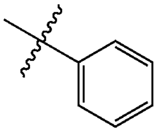 and 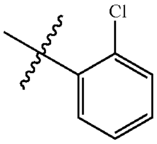;

the C ring is selected from the group consisting of

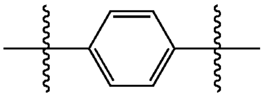, 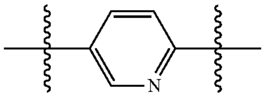, 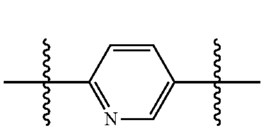, 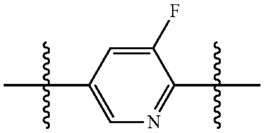, 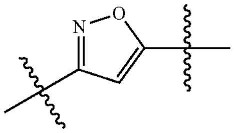 and 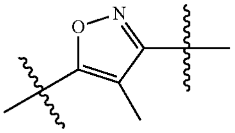;

and the D ring is

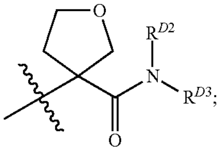;

$R^{D2}$ and $R^{D3}$ are independently selected from the group consisting of hydrogen, $C_{1-6}$ alkyl, —$C_{0-2}$ alkylene-$OR^{D4}$, —$C_{0-2}$ alkylene-(3- to 10-membered cycloalkyl), —$C_{0-2}$ alkylene-(3- to 10-membered heterocycloalkyl), —$C_{0-2}$ alkylene-(5- to 10-membered aromatic ring) and —$C_{0-2}$ alkylene-(5- to 10-membered heteroaromatic ring); wherein alkyl, alkylene, cycloalkyl, heterocycloalkyl, aromatic ring and heteroaromatic ring are independently unsubstituted or substituted with 1, 2 or 3 $R^{D4}$ groups;

the $R^{D4}$ groups are each independently selected from the group consisting of hydrogen, $C_{1-6}$ alkyl, halogen-substituted $C_{1-6}$ alkyl, halogen, cyano, ═O, nitro, —OH, —O($C_{1-6}$ alkyl), —$NH_2$, —NH($C_{1-6}$ alkyl), —N($C_{1-6}$ alkyl) ($C_{1-6}$ alkyl), —$C_{0-2}$ alkylene-(3- to 10-membered cycloalkyl), —$C_{0-2}$ alkylene-(3- to 10-membered heterocycloalkyl), —$C_{0-2}$ alkylene-(5- to 10-membered aromatic ring) and —$C_{0-2}$ alkylene-(5- to 10-membered heteroaromatic ring).

In an embodiment, the D ring selected from the group consisting of

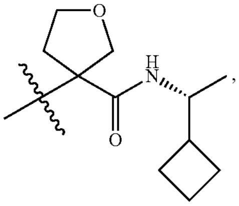, 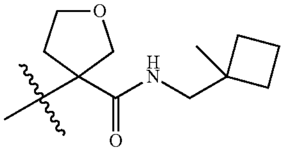, 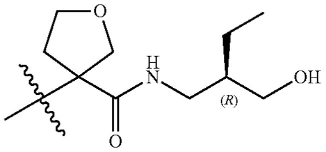 and 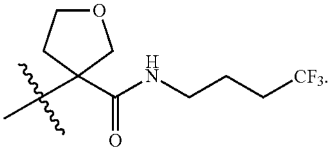.

In an embodiment, the compound is shown in formula (V):

(V)

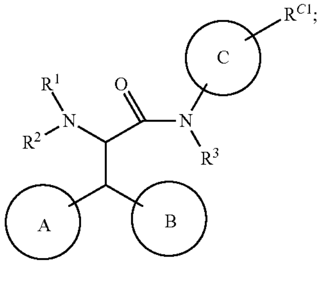

wherein $R^1$ is —C(O)$R^{11}$; $R^{11}$ is selected from the group consisting of

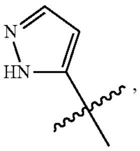, 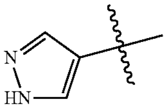, 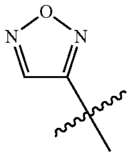, 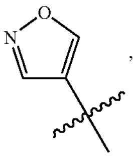, 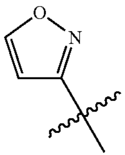 and 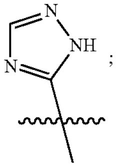;

wherein

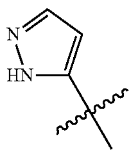,
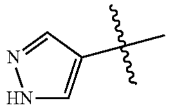,
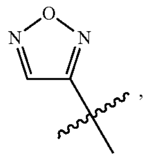,
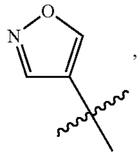,
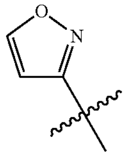
and
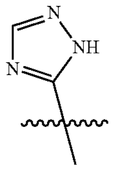

are independently unsubstituted or substituted with 1, 2 or 3 $R^{1a}$ groups; the $R^{1a}$ groups are each independently selected from the group consisting of hydrogen, halogen, cyano, —$C_{1-6}$ alkyl, halogen-substituted —$C_{1-6}$ alkyl, 3- to 6-membered cycloalkyl and —$C_{0-2}$ alkylene-$OR^{1b}$; wherein $R^{1b}$ is selected from the group consisting of hydrogen, $C_{1-6}$ alkyl and halogen-substituted $C_{1-6}$ alkyl;

$R^2$ and $R^3$ are independently selected from the group consisting of hydrogen and —$C_{1-6}$ alkyl;

the A ring is selected from the group consisting of

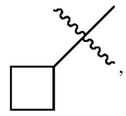,
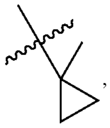,
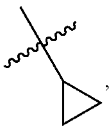,
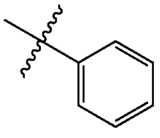
and
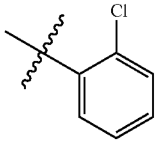;

the B ring is selected from the group consisting of

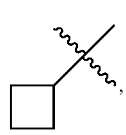,
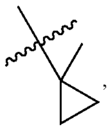,
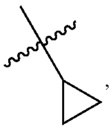,
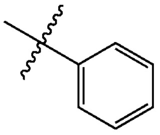
and
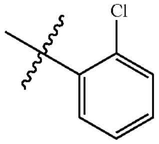;

and the C ring is selected from the group consisting of

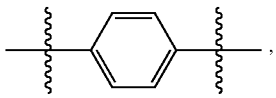,
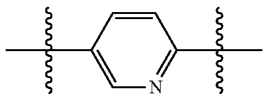,

-continued

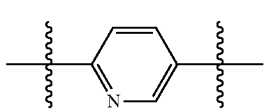,
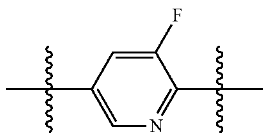,
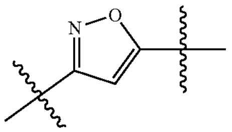
and
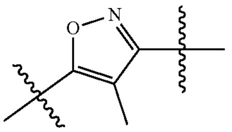;

$R^{C1}$ is —$C_{0-4}$ alkylene-C(O)$NR^{C2}R^{C3}$;

$R^{C2}$ and $R^{C3}$ are independently selected from the group consisting of hydrogen, —$C_{1-6}$ alkyl, —$C_{0-2}$ alkylene-$OR^{C4}$, —$C_{0-2}$ alkylene-(3- to 10-membered cycloalkyl) and —$C_{0-2}$ alkylene-(3- to 10-membered heterocycloalkyl); wherein alkyl, alkylene and cycloalkyl are independently unsubstituted or substituted with 1, 2 or 3 $R^{C4}$ groups; and the $R^{C4}$ groups are each independently selected from the group consisting of hydrogen, $C_{1-6}$ alkyl, halogen-substituted $C_{1-6}$ alkyl, halogen, cyano, =O, nitro, —OH, —O($C_{1-6}$ alkyl), —$NH_2$, —NH($C_{1-6}$ alkyl), —N($C_{1-6}$ alkyl) ($C_{1-6}$ alkyl).

In an embodiment, in the formula (V),

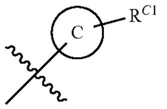

is selected from the group consisting of

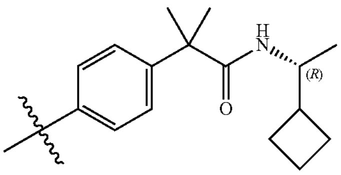,
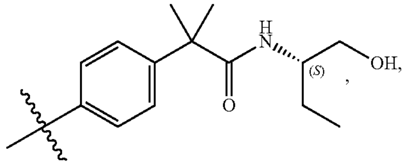,
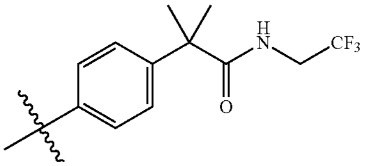
and
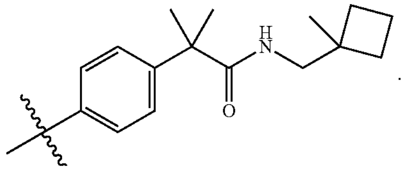.

In an embodiment, the compound is shown in formula (VI):

(VI)

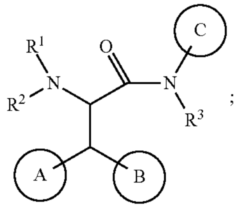;

wherein $R^1$ is —C(O)$R^{11}$; wherein $R^{11}$ is selected from the group consisting of

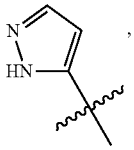, 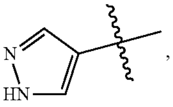, 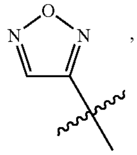, 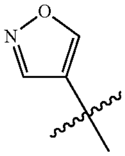, 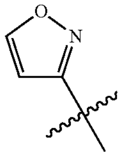 and 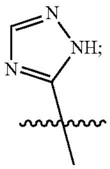;

wherein

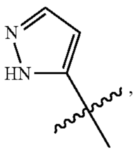, 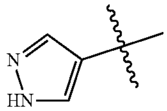, 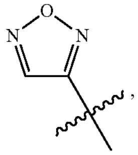, 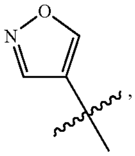, 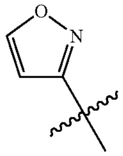 and 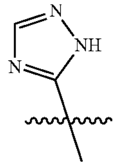

are independently unsubstituted or substituted with 1, 2 or 3 $R^{1a}$ groups; the $R^{1a}$ groups are each independently selected from the group consisting of hydrogen, halogen, cyano, —$C_{1-6}$ alkyl, halogen-substituted-$C_{1-6}$ alkyl, 3- to 6-membered cycloalkyl and —$C_{0-2}$ alkylene-$OR^{1b}$; wherein $R^{1b}$ is selected from the group consisting of hydrogen, $C_{1-6}$ alkyl and halogen-substituted $C_{1-6}$ alkyl.

$R^2$ and $R^3$ are independently selected from the group consisting of hydrogen and —$C_{1-6}$ alkyl;

the A ring is selected from the group consisting of

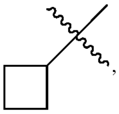, 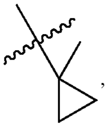, 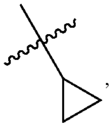, 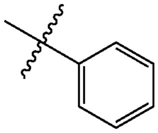 and

-continued

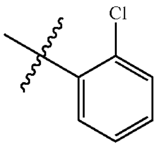;

the B ring is selected from the group consisting of

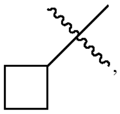, 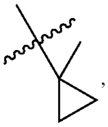, 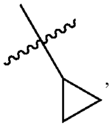, 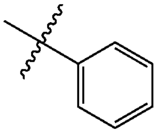 and

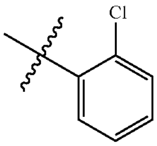;

and the C ring is selected from the group consisting of

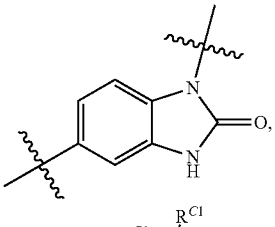,

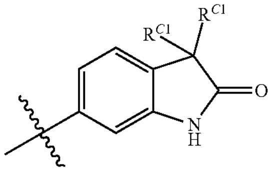 and

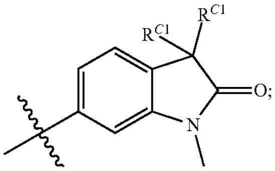;

wherein two $R^{C1}$ groups are independent or linked to form 3- to 10-membered cycloalkyl or 3- to 10-membered heterocycloalkyl.

In an embodiment, the C ring is selected from the group consisting of

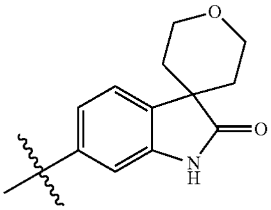 and

-continued
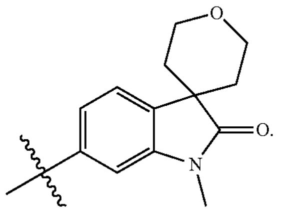
In an embodiment, the compound is selected from the group consisting of:
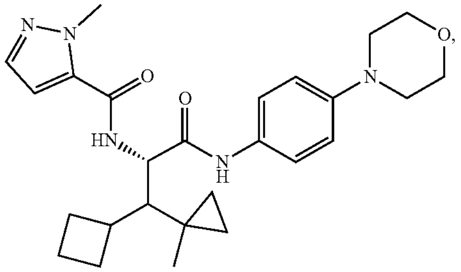,
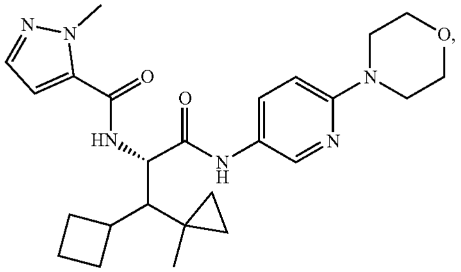,
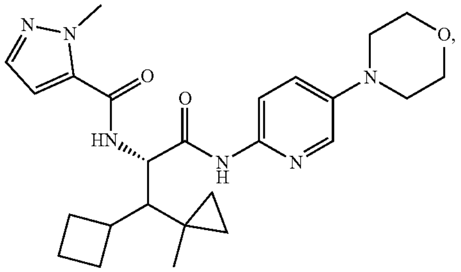,
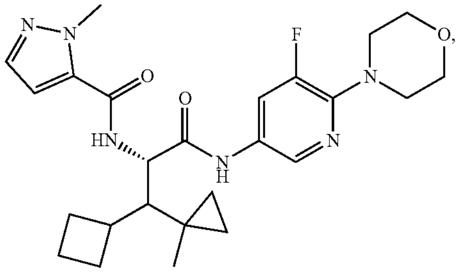,
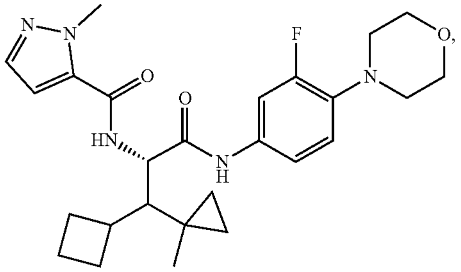,
-continued
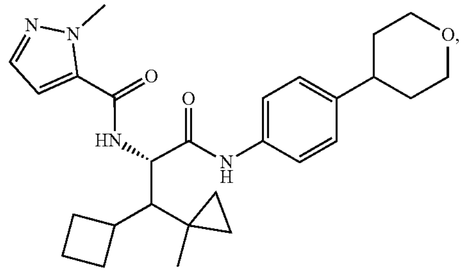,
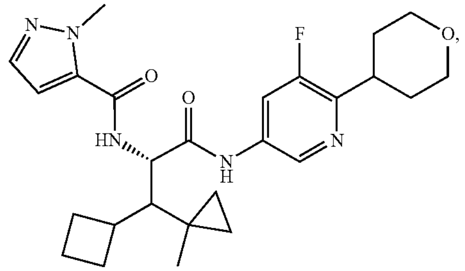,
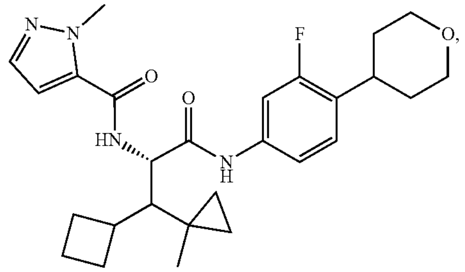,
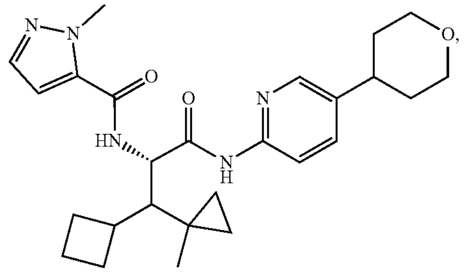,
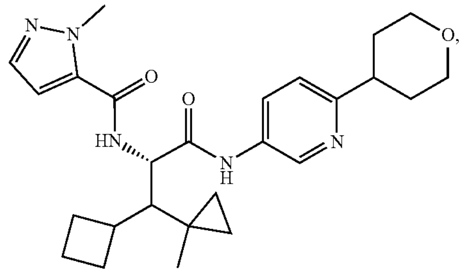,
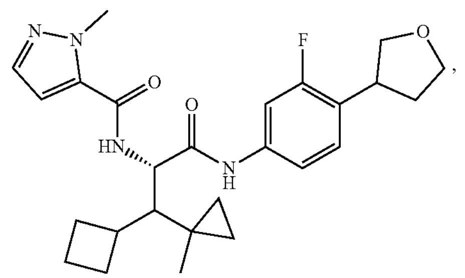, -continued
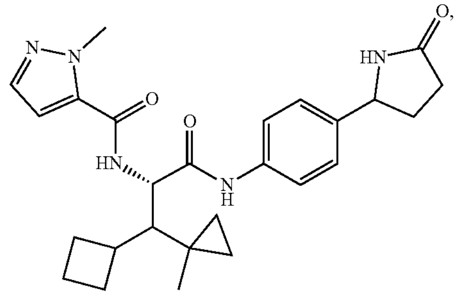
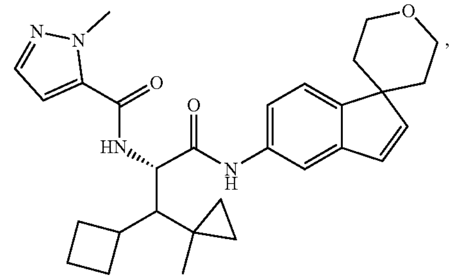
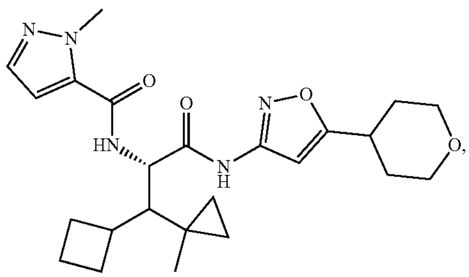
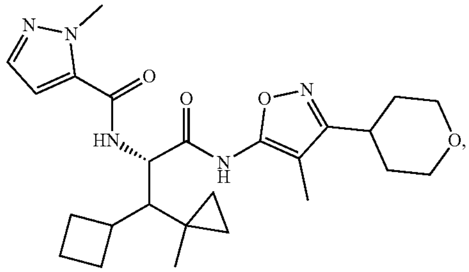
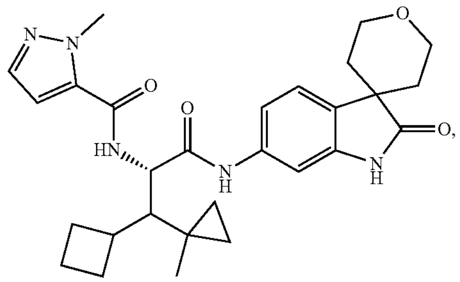
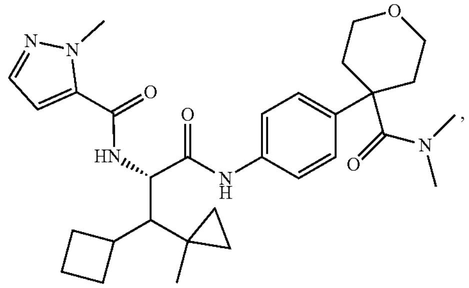
-continued
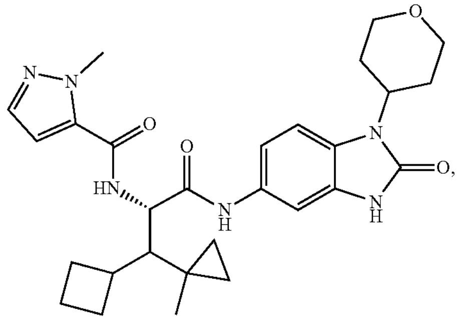
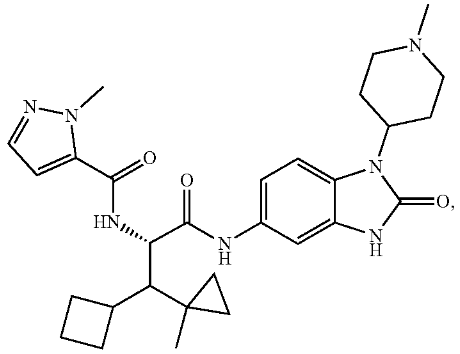
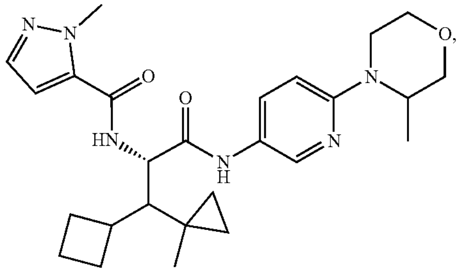
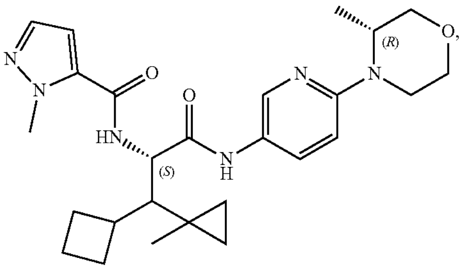
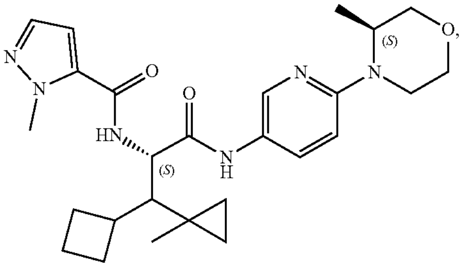

-continued
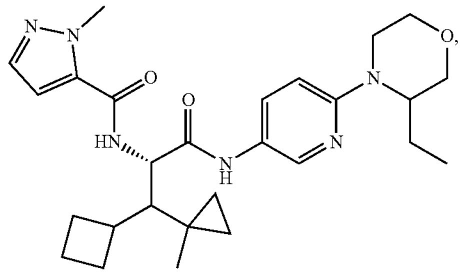
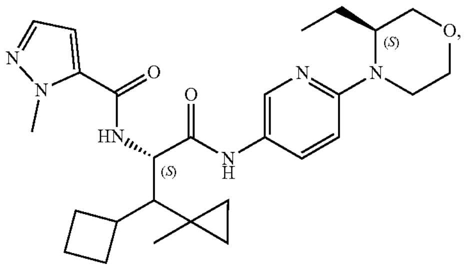
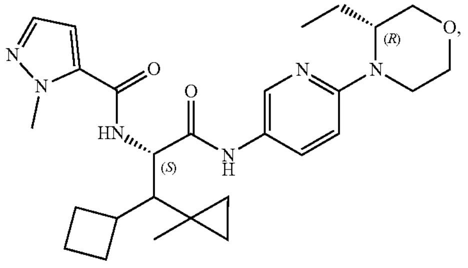
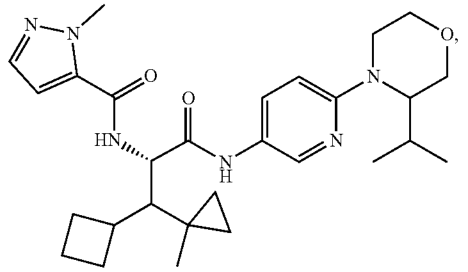
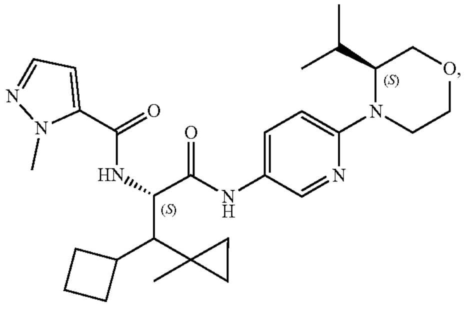
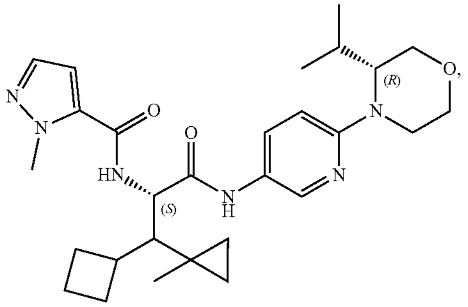
-continued
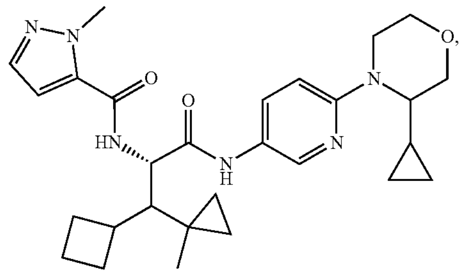
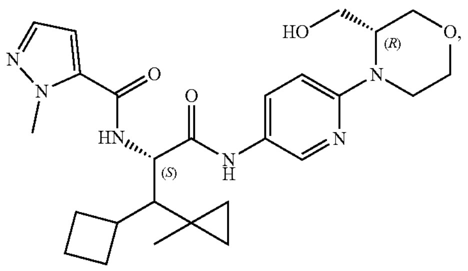
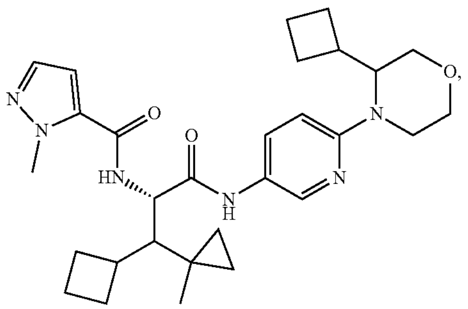
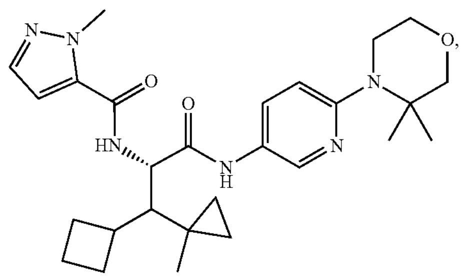
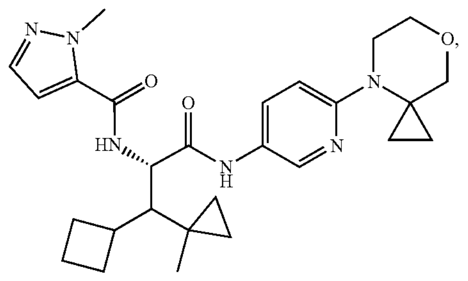
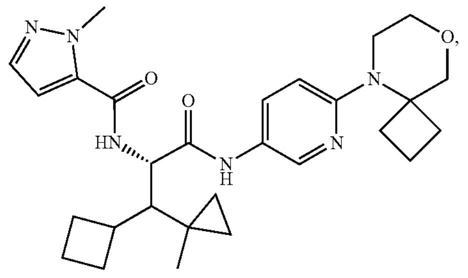

-continued
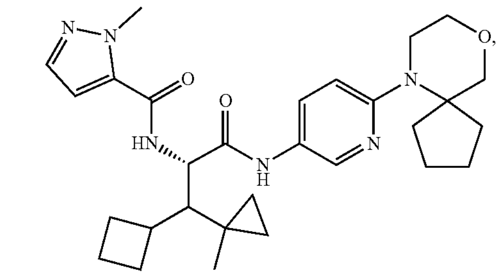,
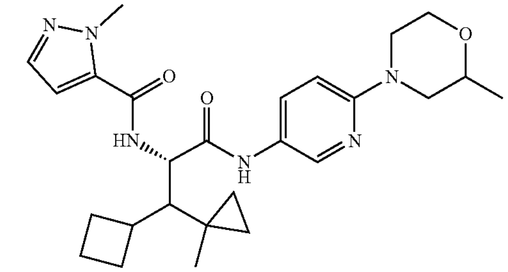,
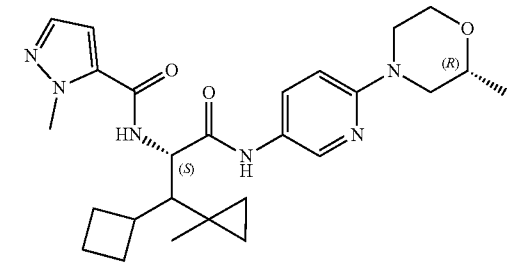,
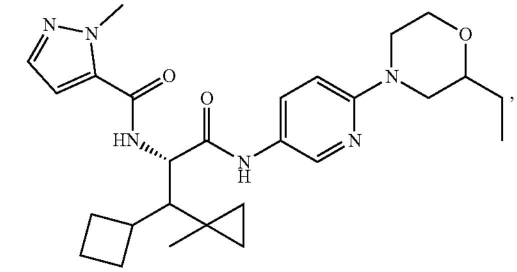,
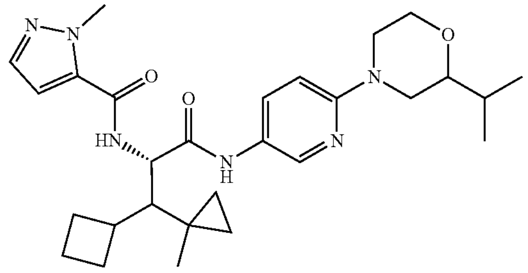,
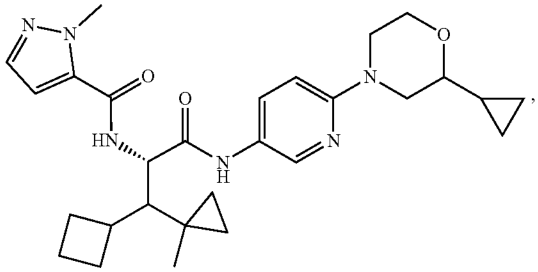,
-continued
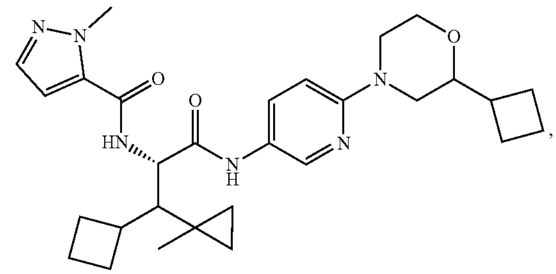,
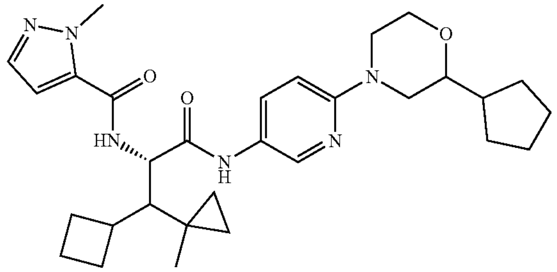,
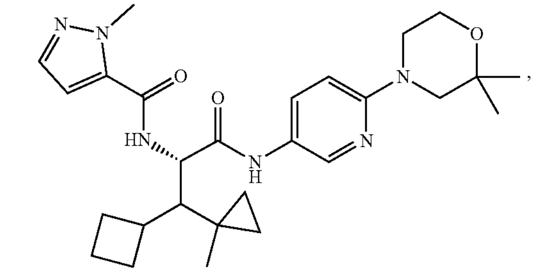,
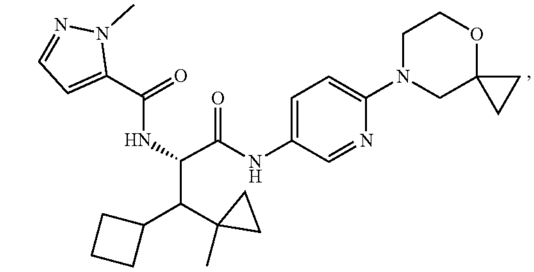,
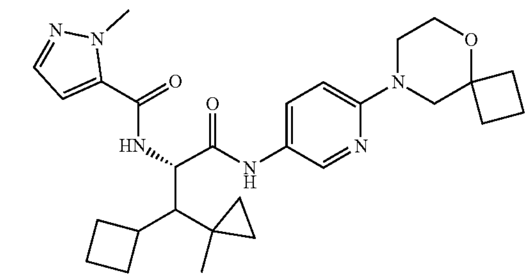,
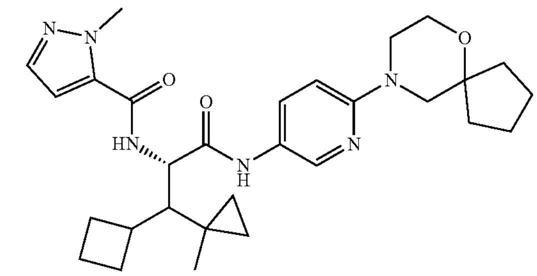, -continued
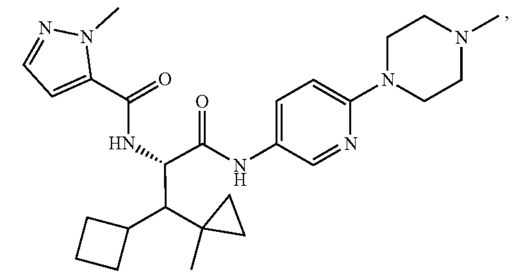
,
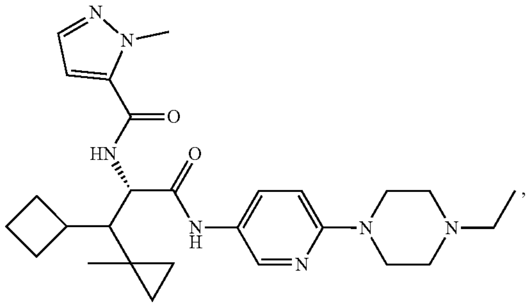
,
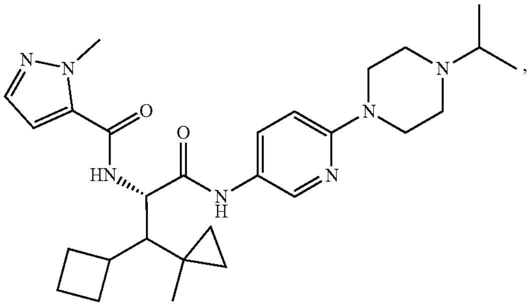
,
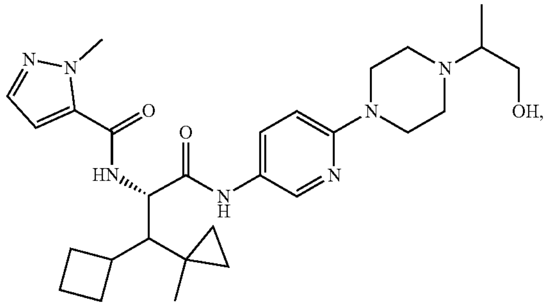
,
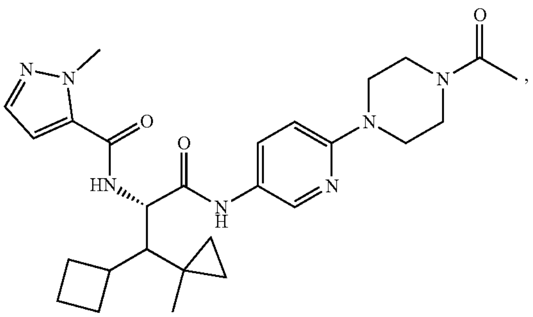
,
-continued
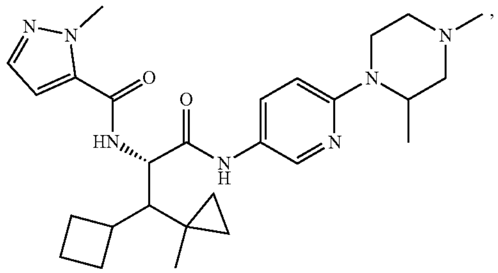
,
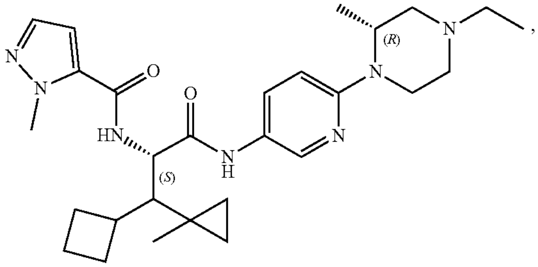
,
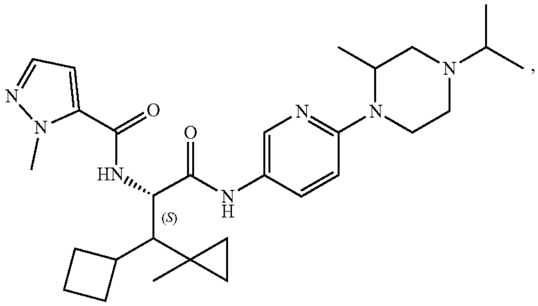
,
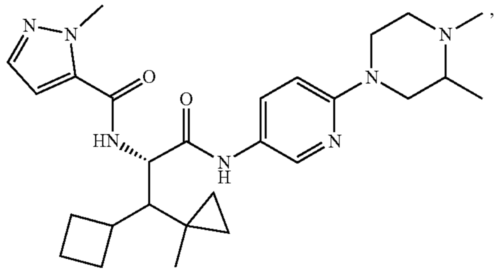
,
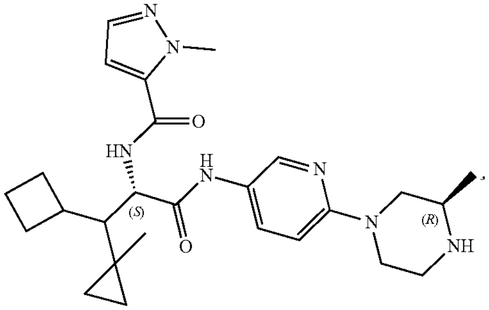
,
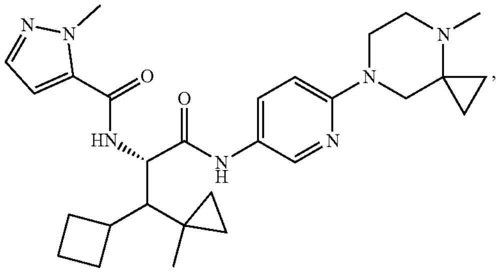
, -continued
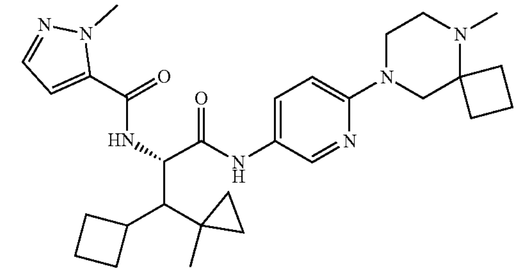
,
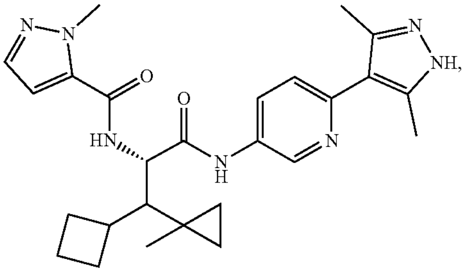
,
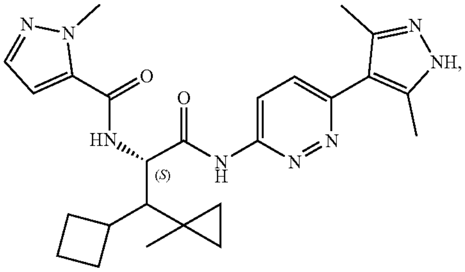
,
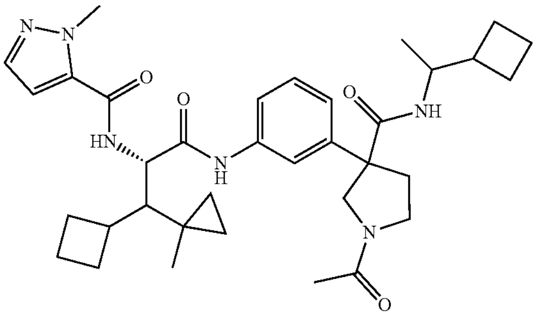
,
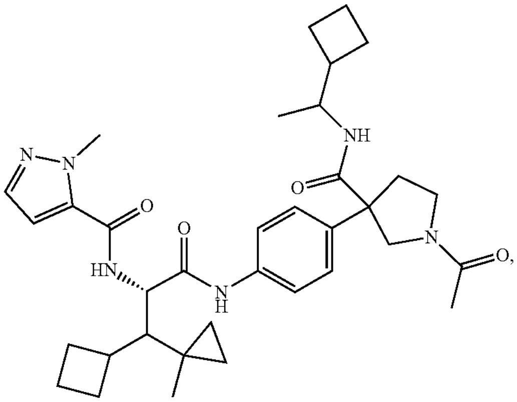
,
-continued
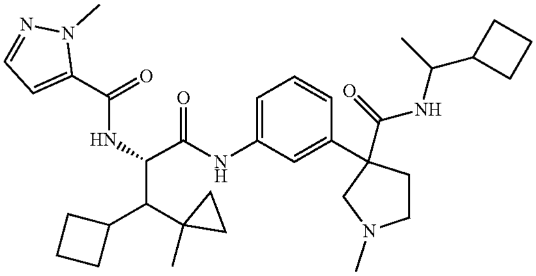
,
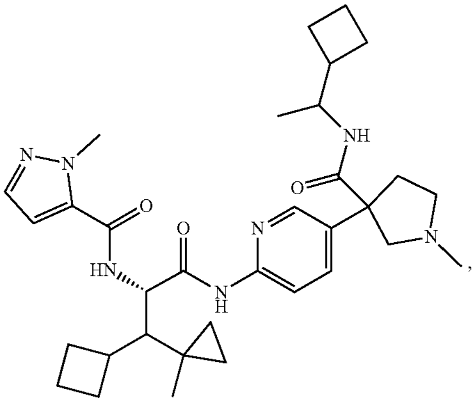
,
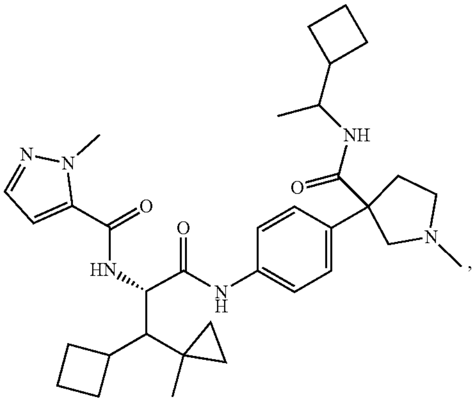
,
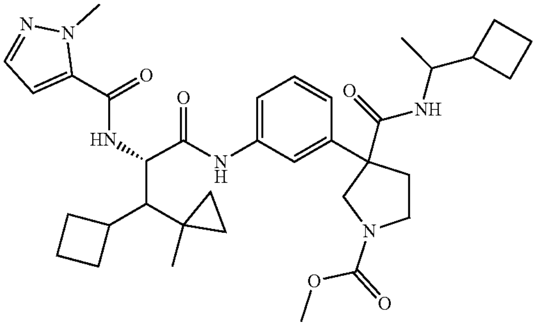
, -continued
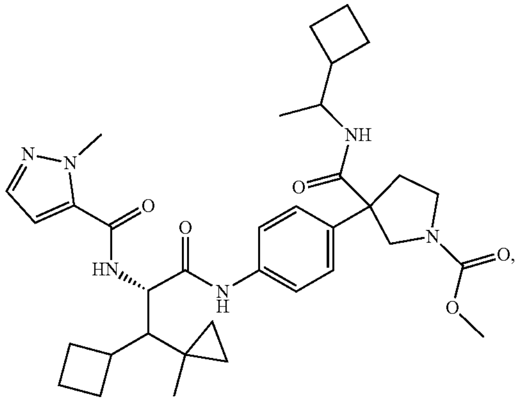
,
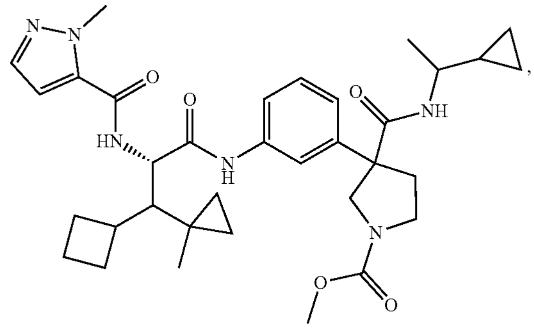
,
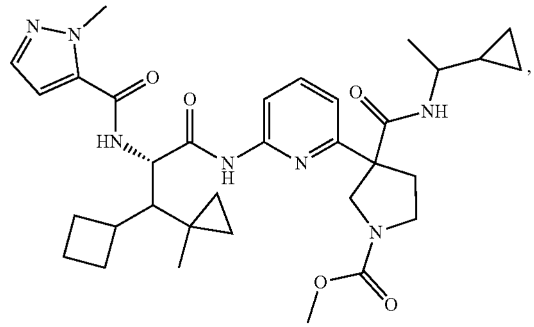
,
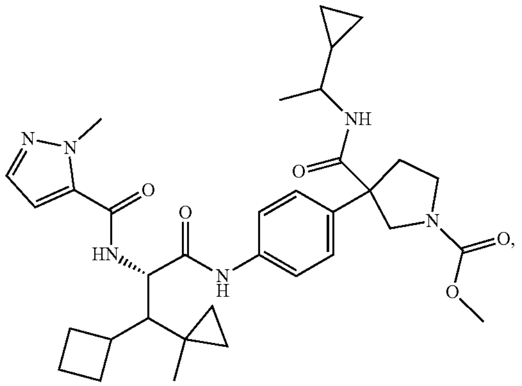
,
-continued
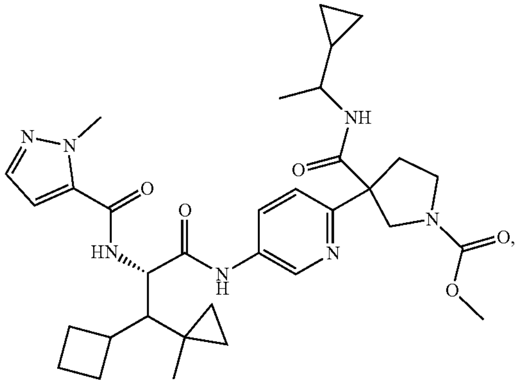
,
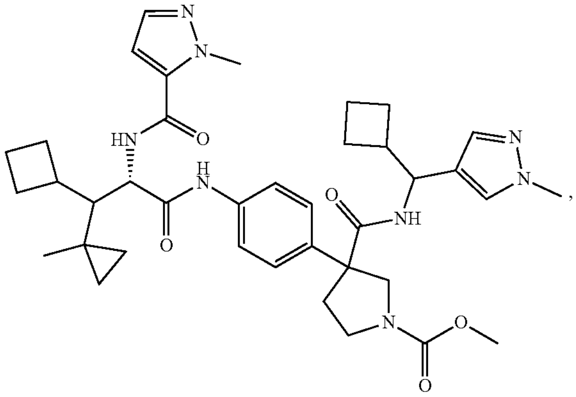
,
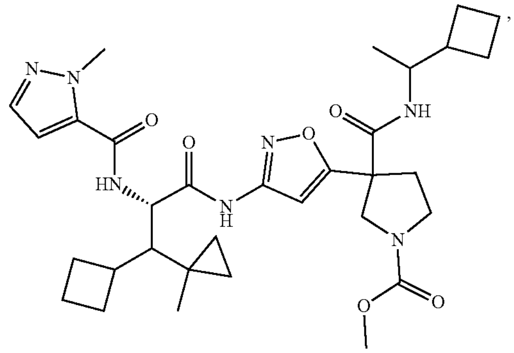
,
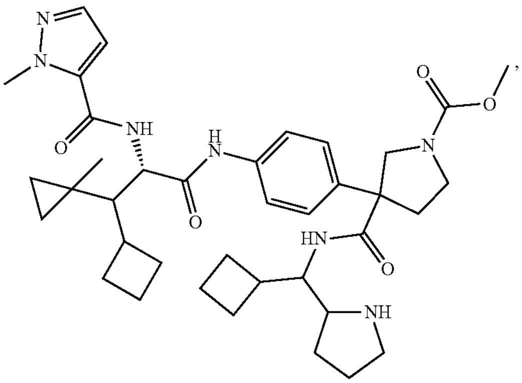
, -continued
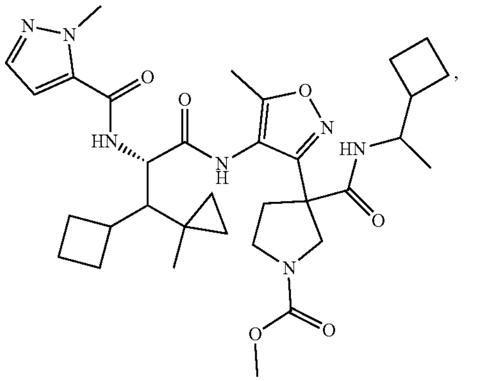
,
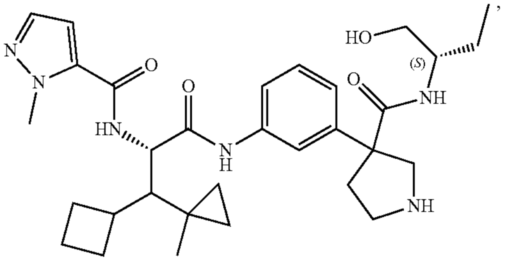
,
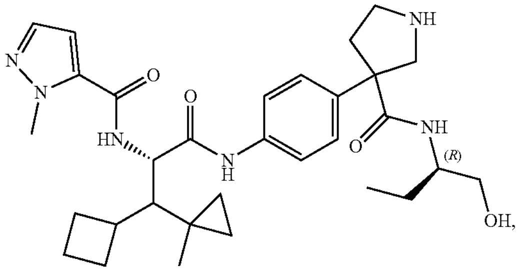
,
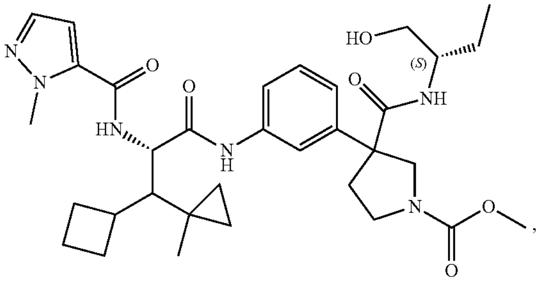
,
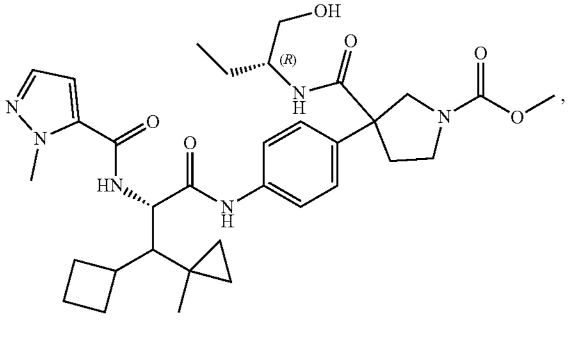
,
-continued
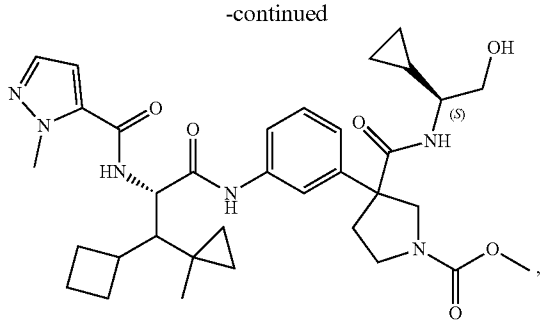
,
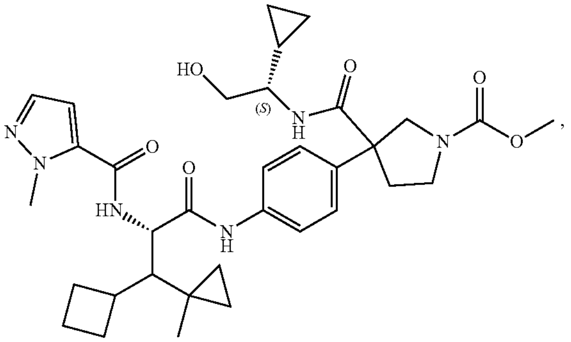
,
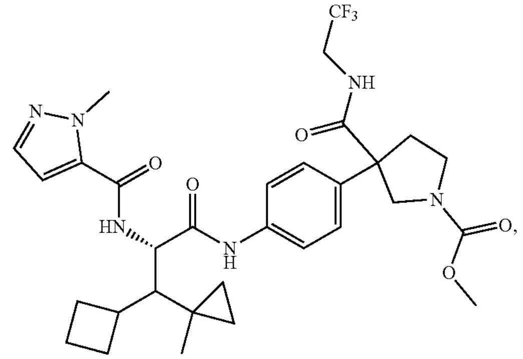
,
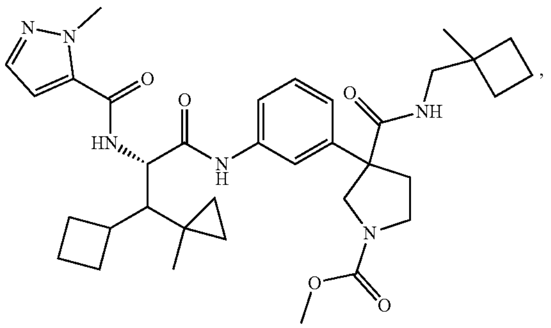
,
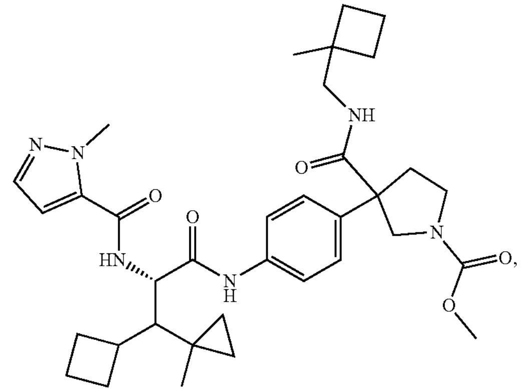
, -continued
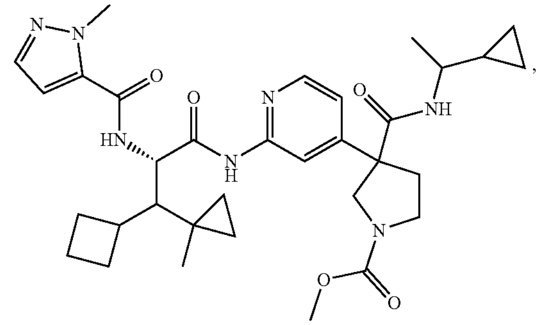
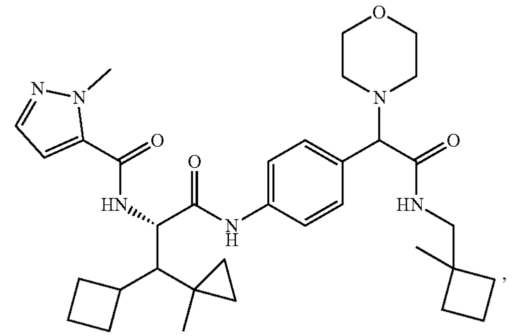
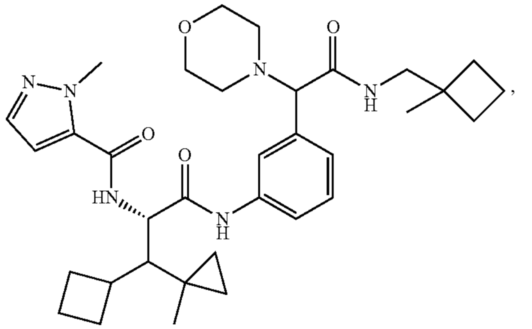
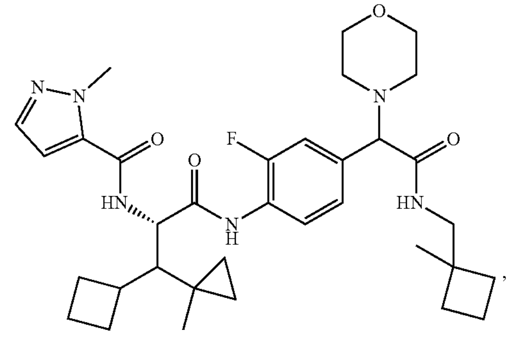
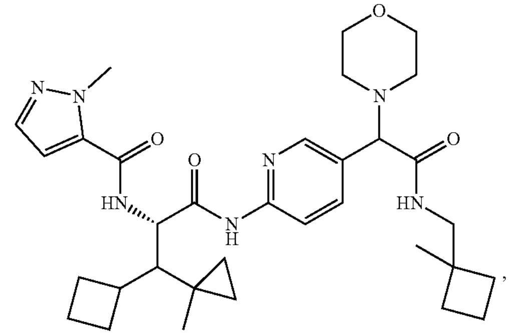
-continued
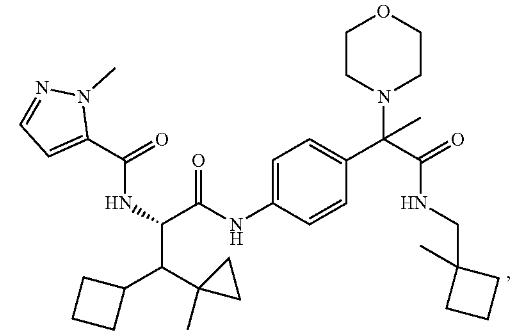
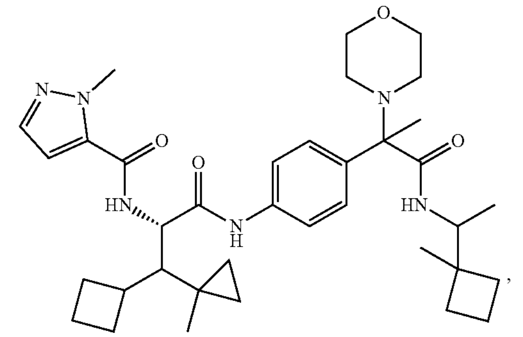
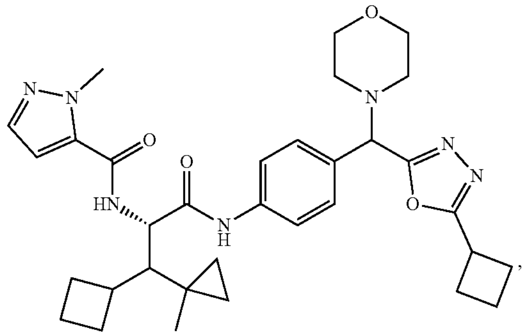
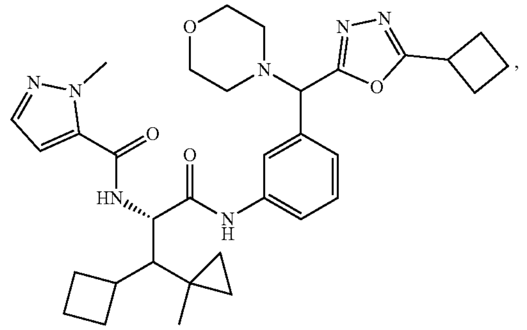
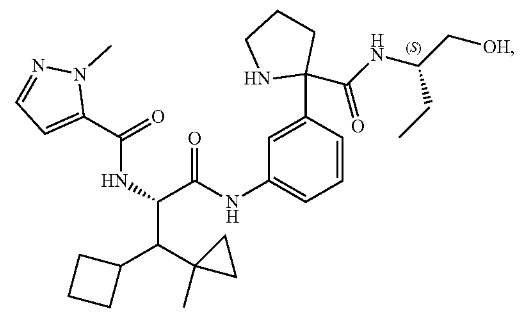

-continued
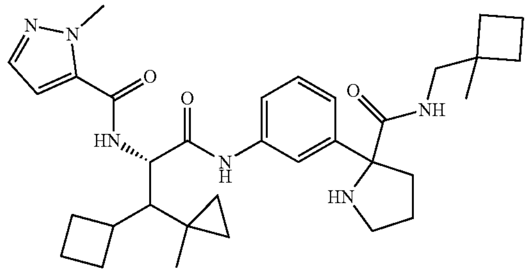
,
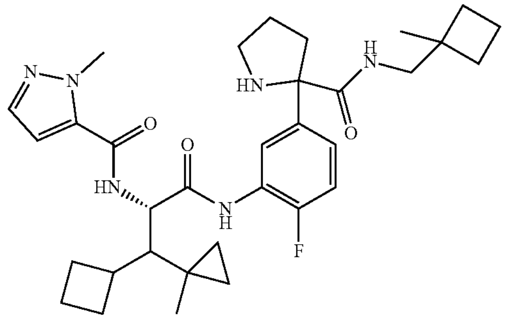
,
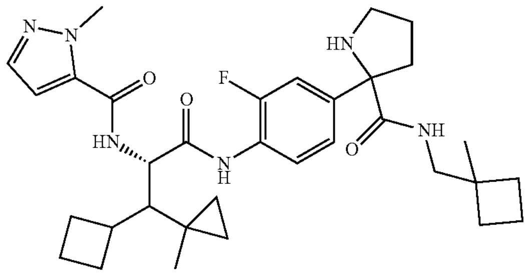
,
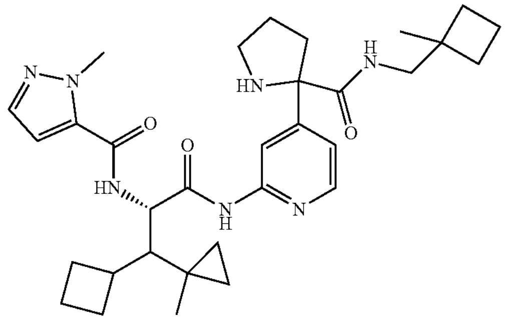
,
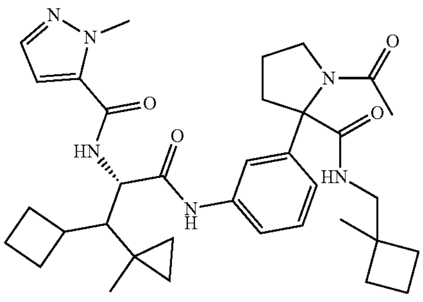
,
-continued
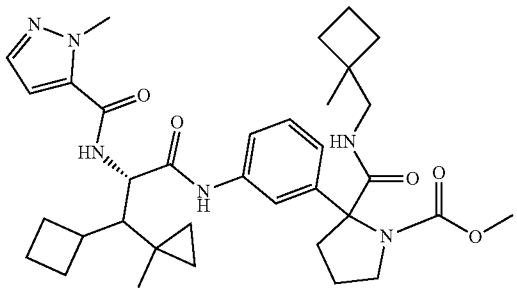
,
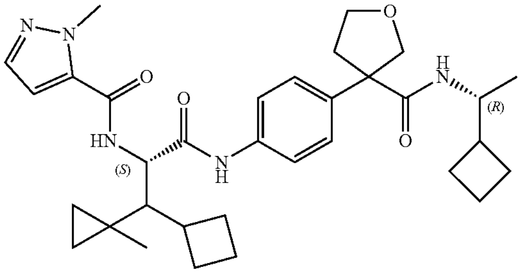
,
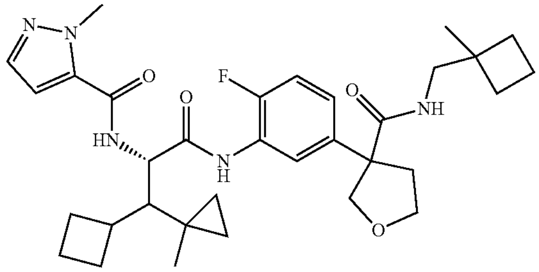
,
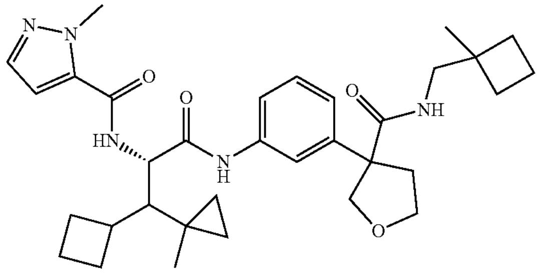
,
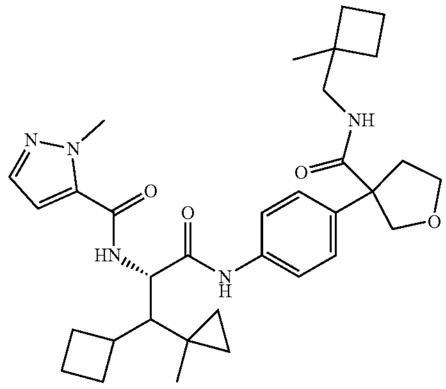
, -continued
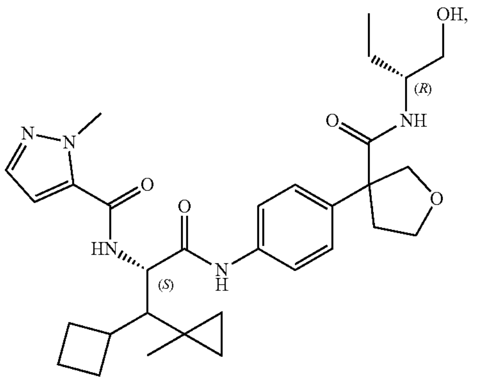
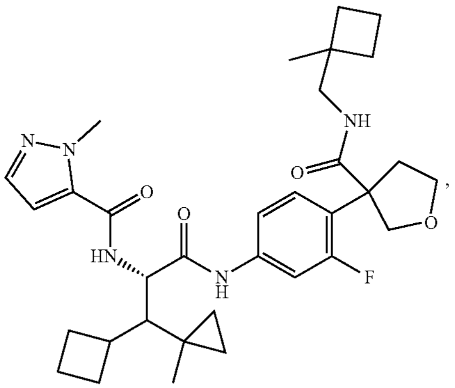
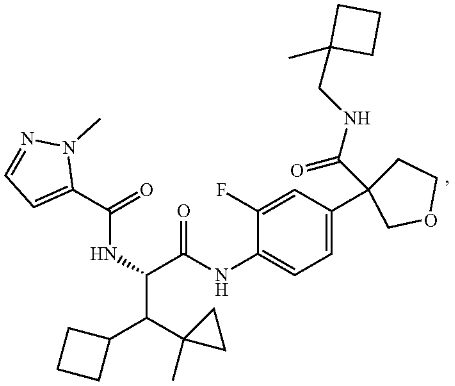
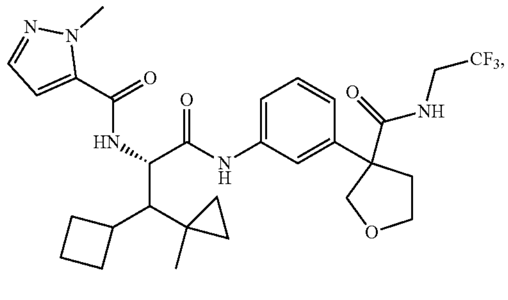
-continued
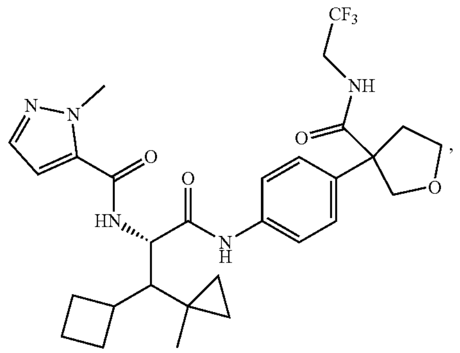
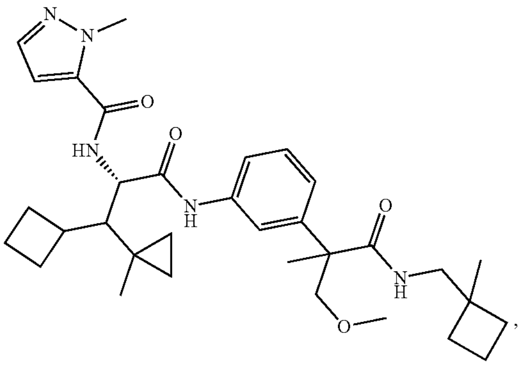
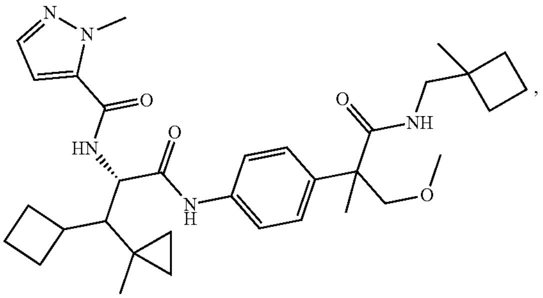
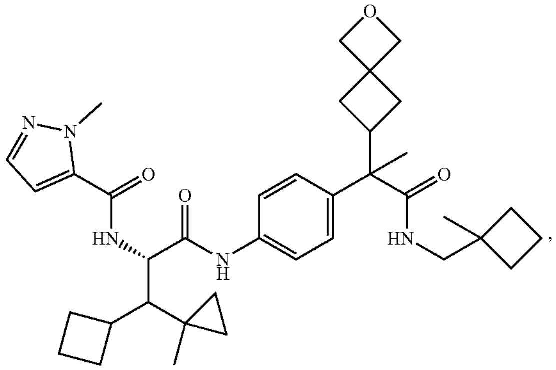

-continued
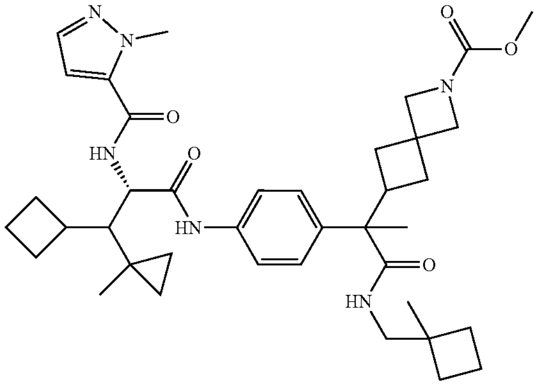
,
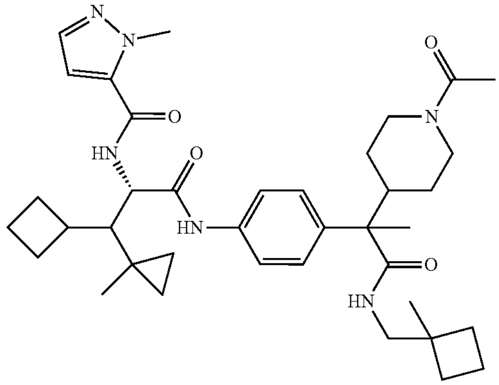
,
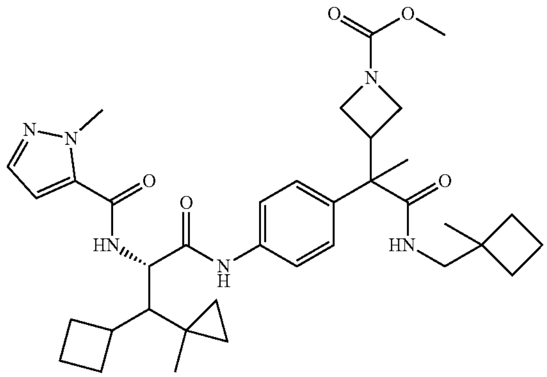
,
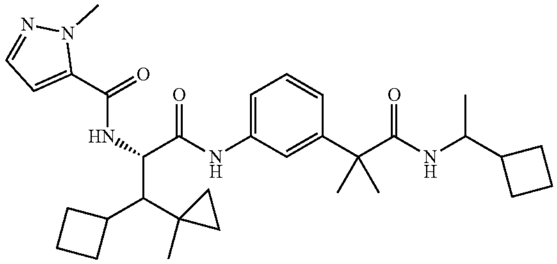
,
-continued
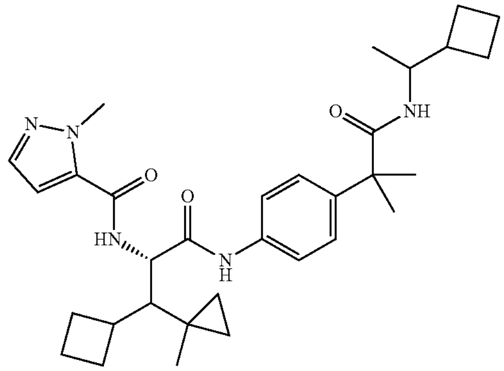
,
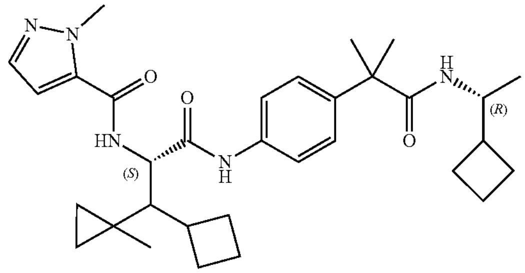
,
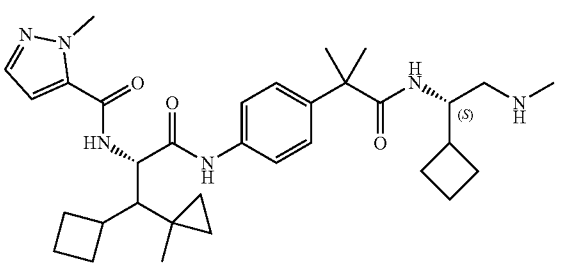
,
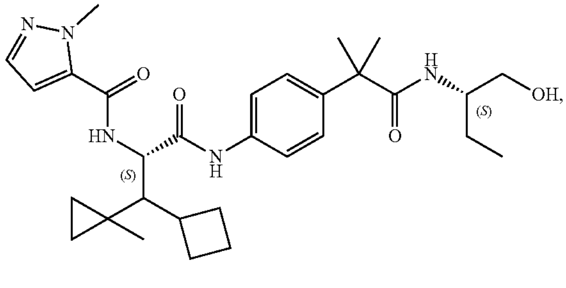
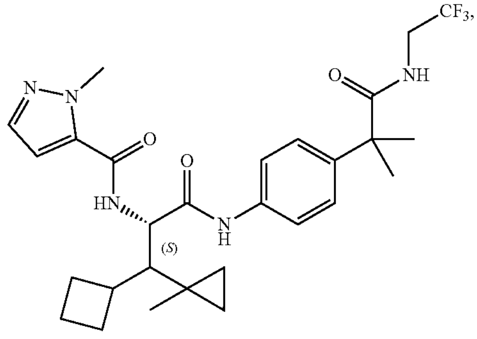

-continued
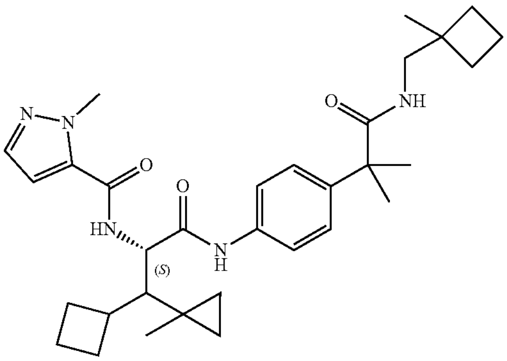
,
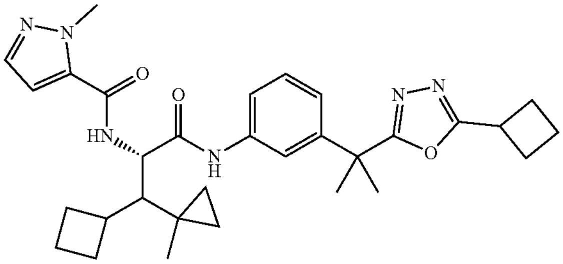
,
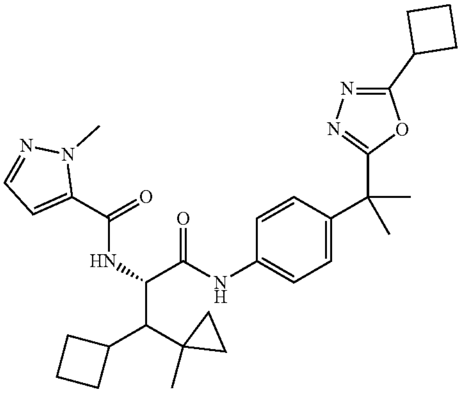
,
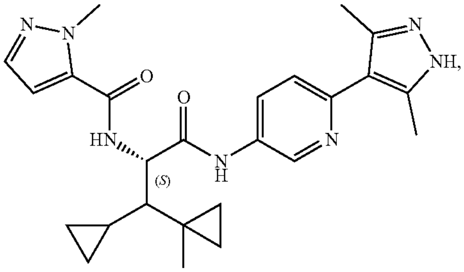
,
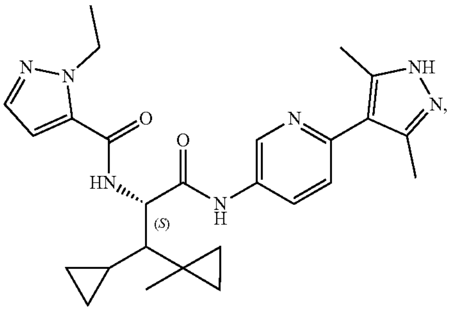
,
-continued
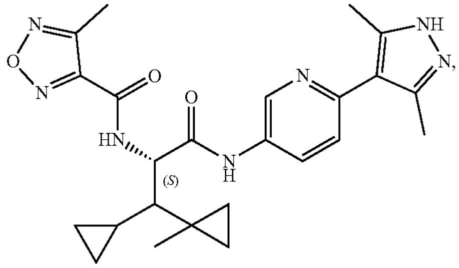
,
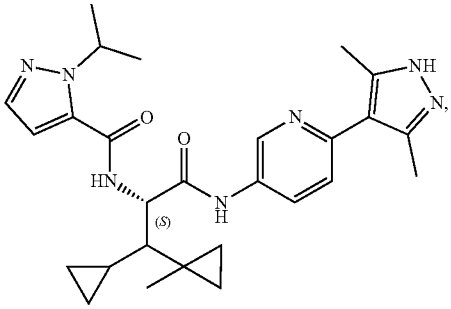
,
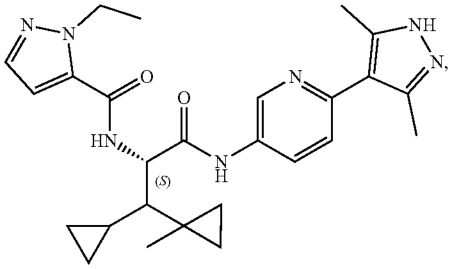
,
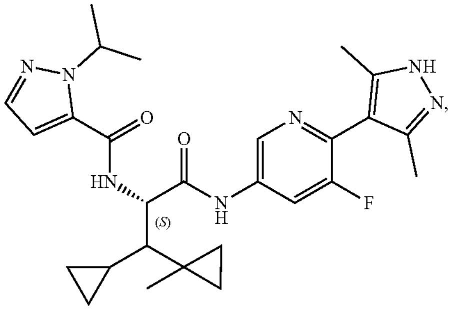
,
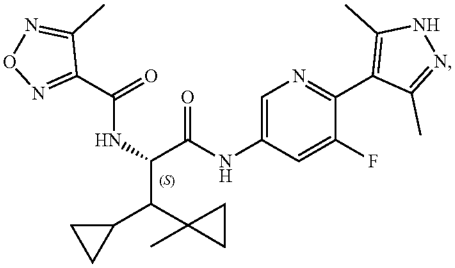
,
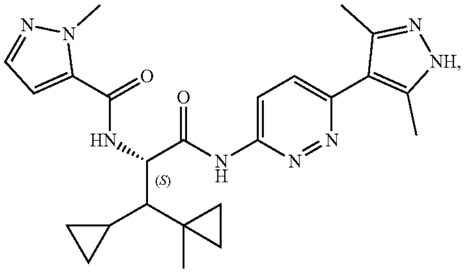
, -continued
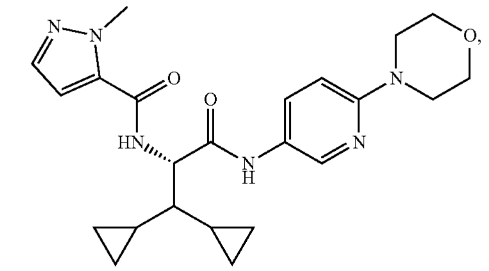
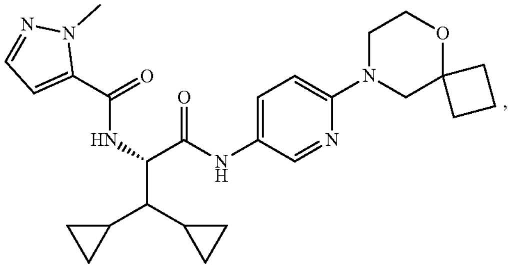
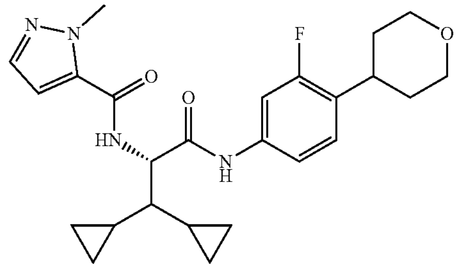
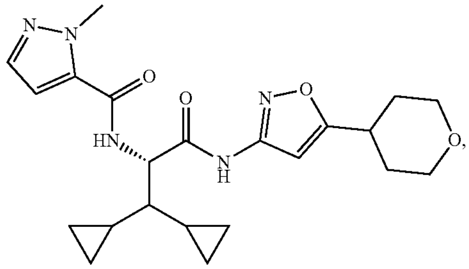
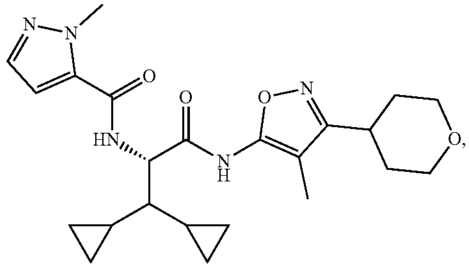
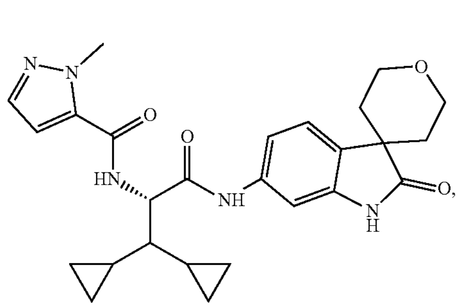
-continued
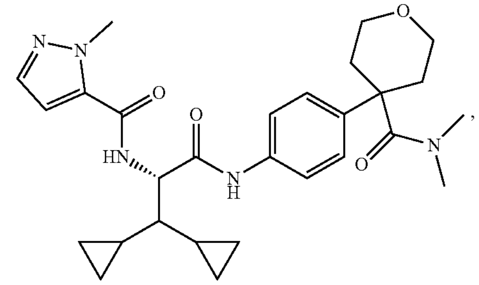
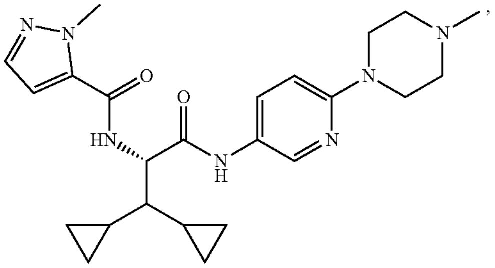
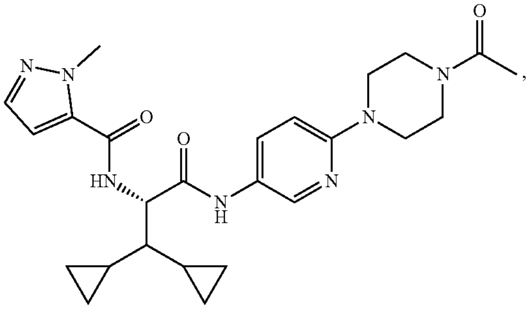
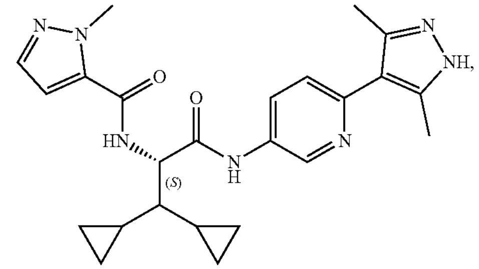
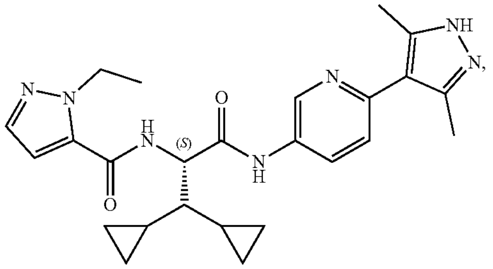
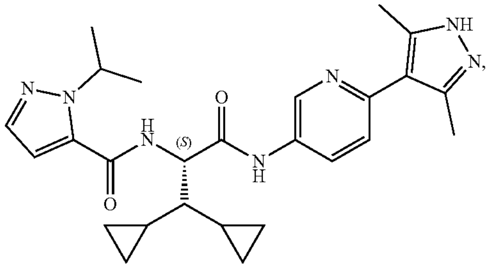

-continued
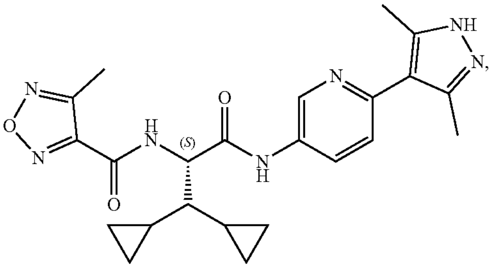
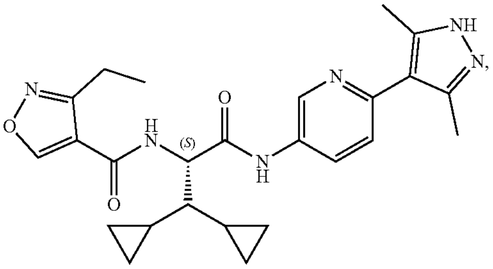
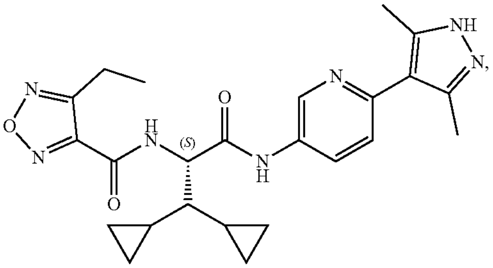
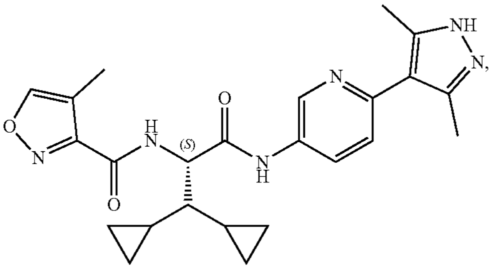
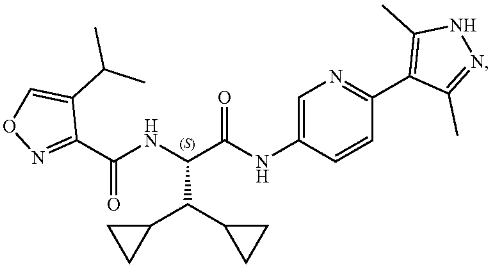
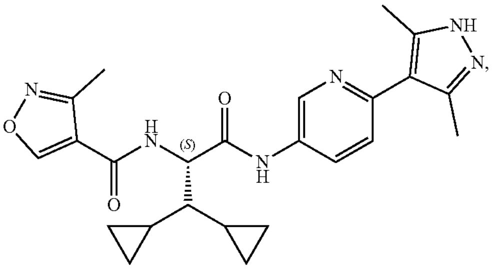
-continued
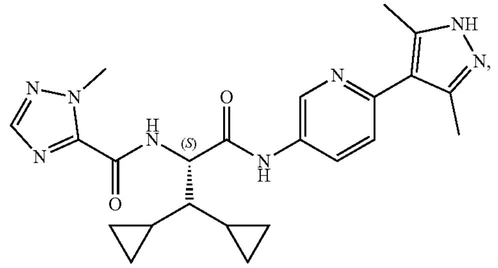
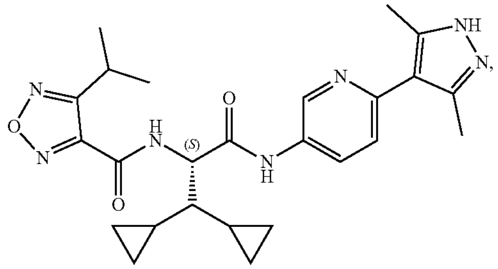
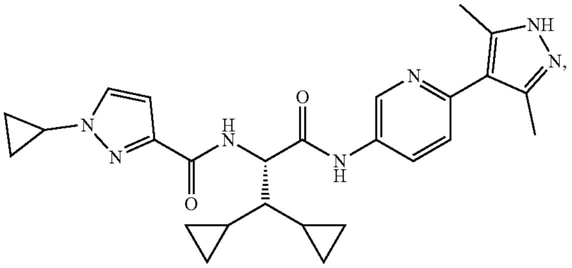
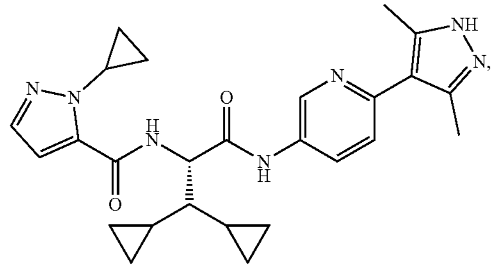
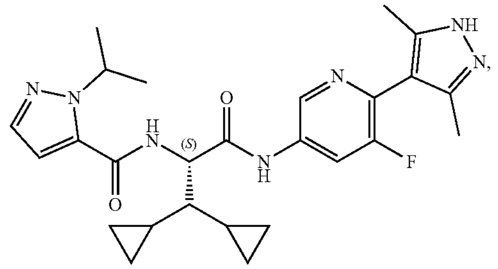
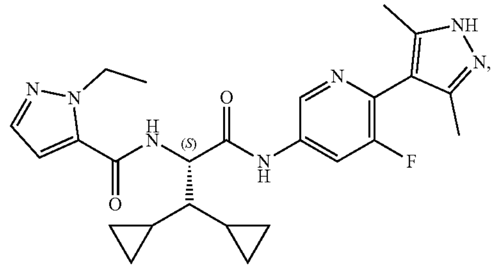

-continued
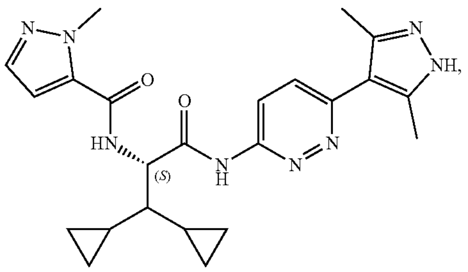
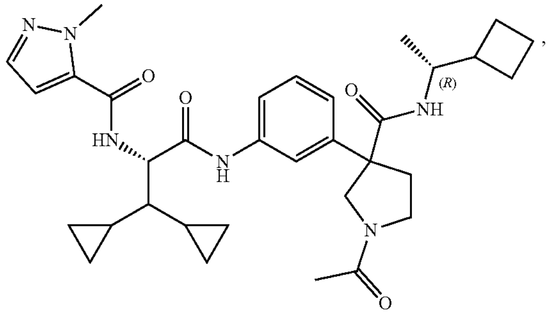
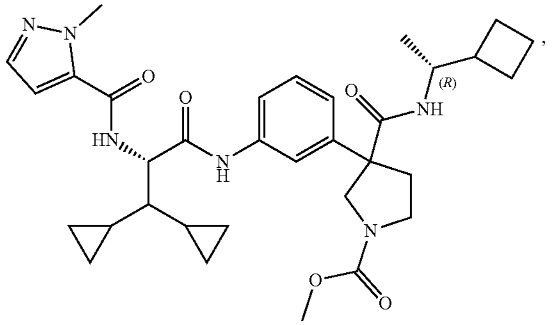
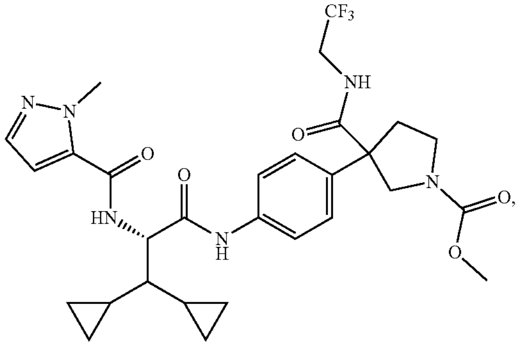
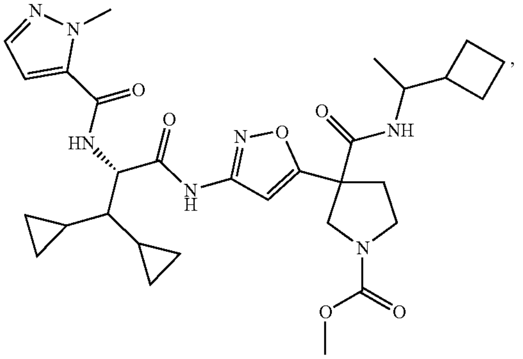
-continued
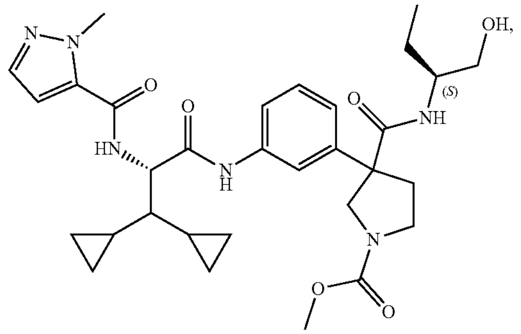
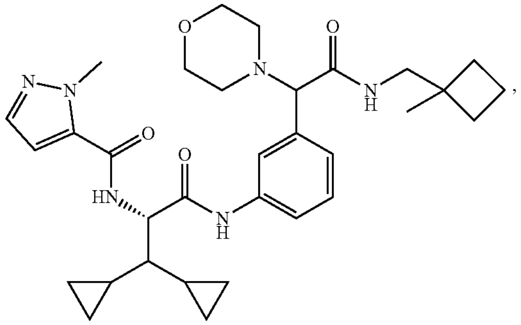
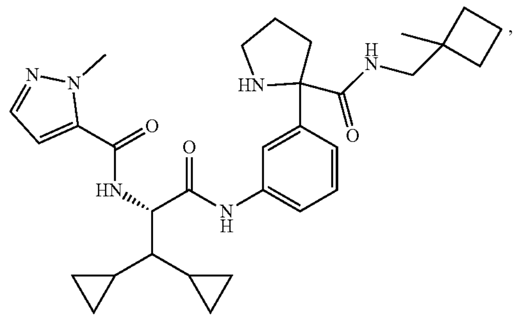
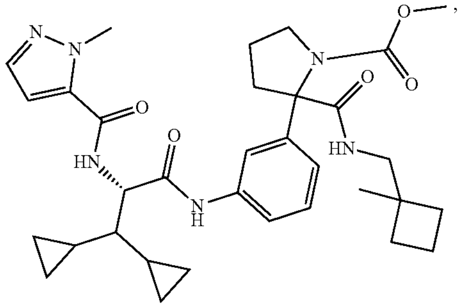
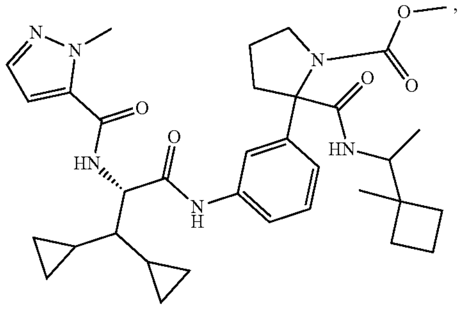

-continued
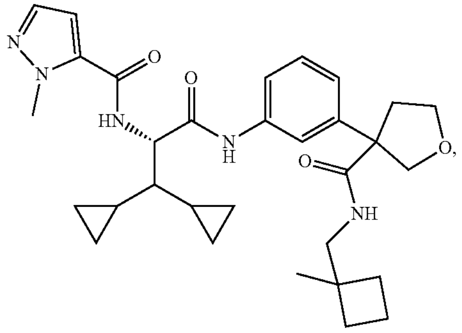
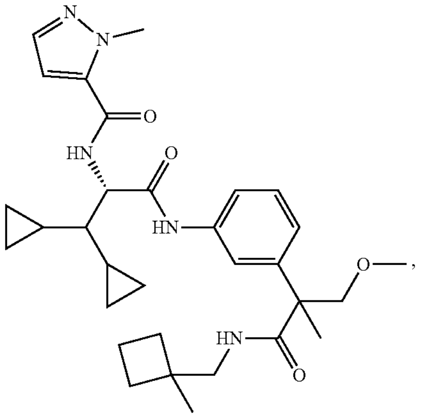
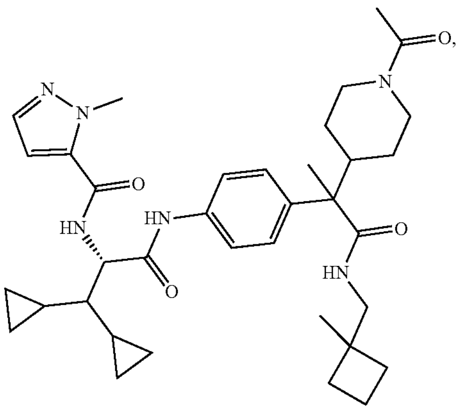
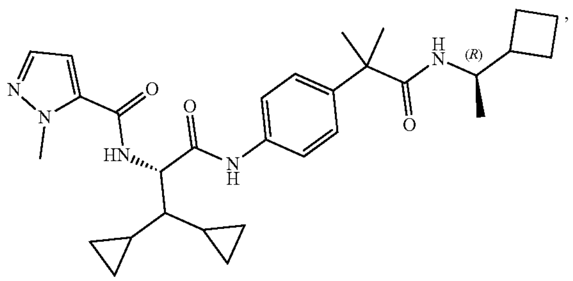
-continued
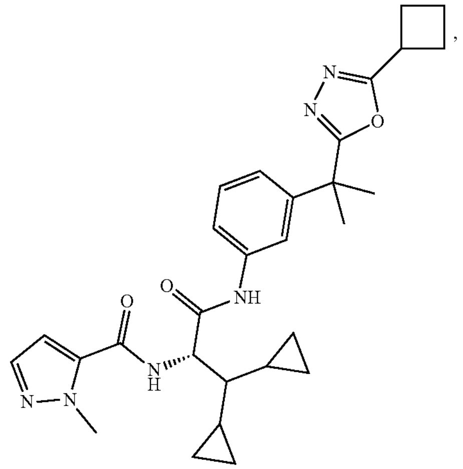
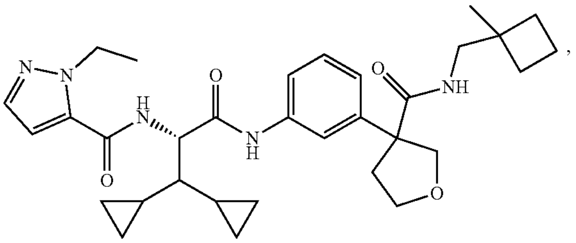
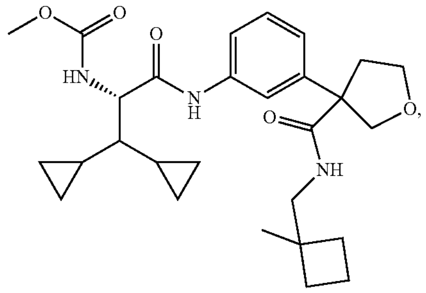
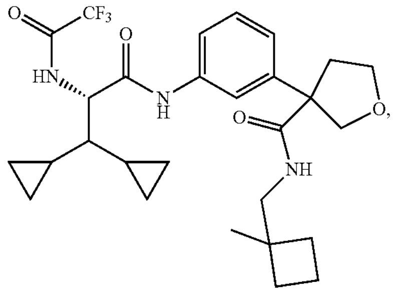
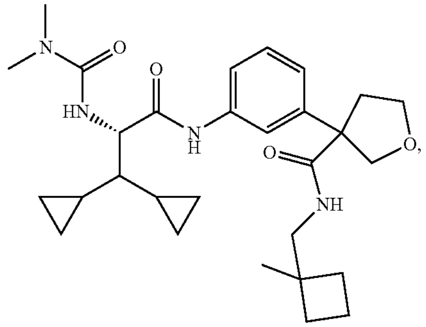

-continued
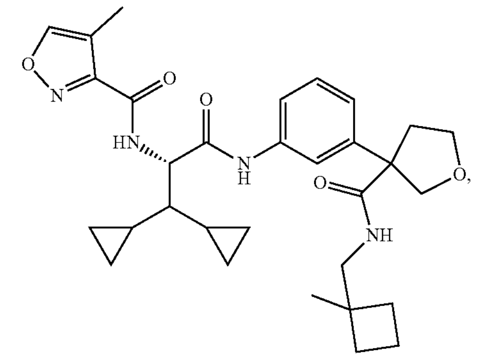
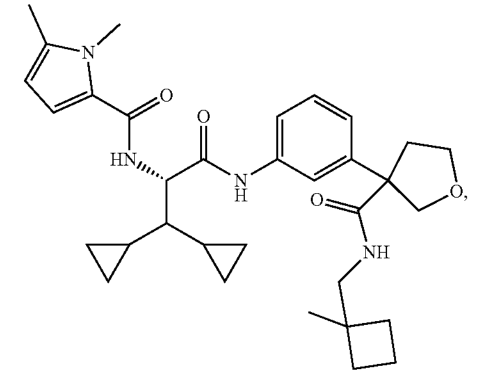
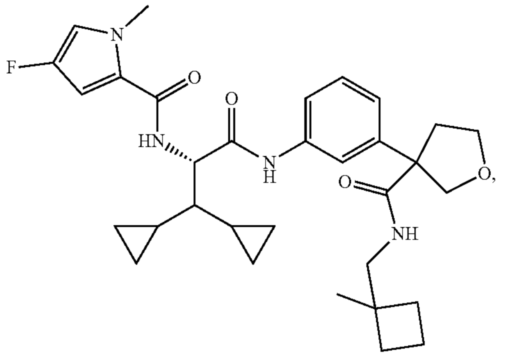
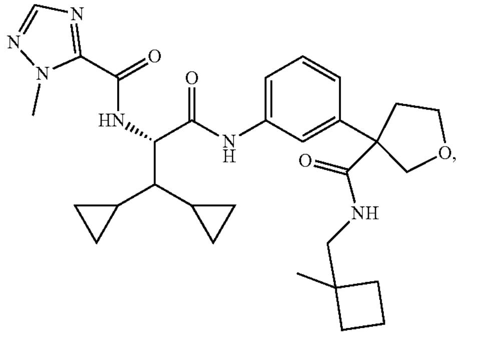
-continued
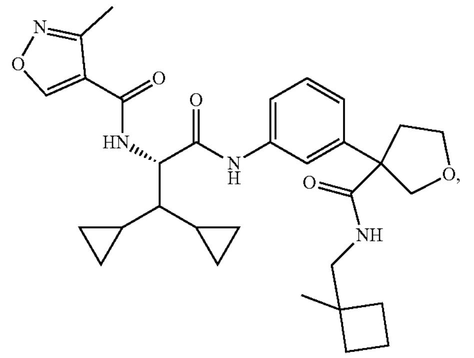
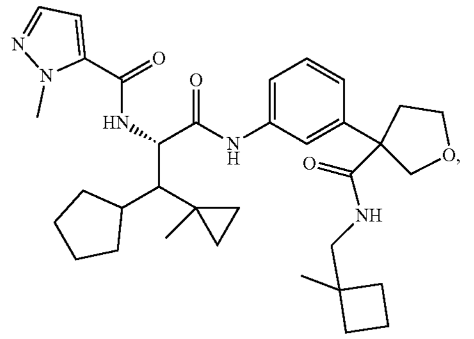
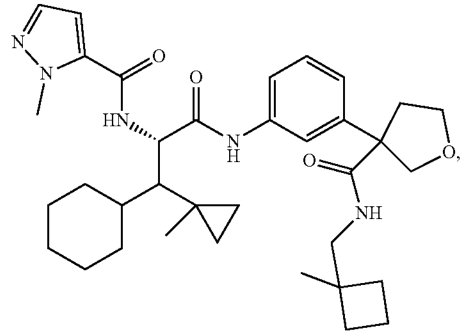
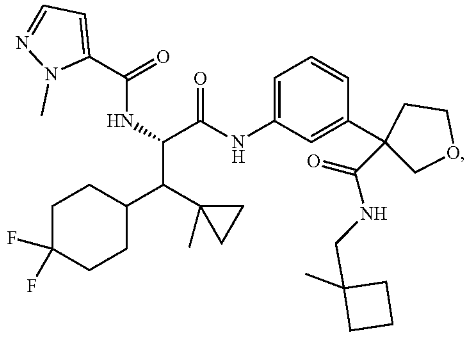
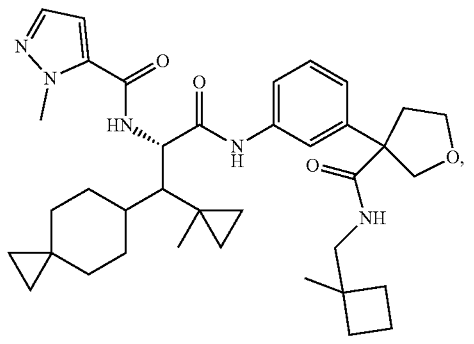

-continued
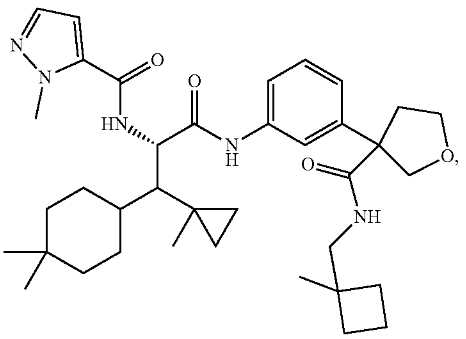
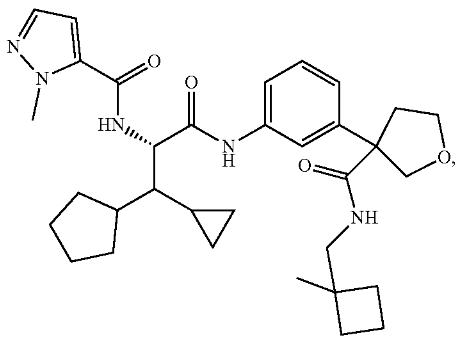
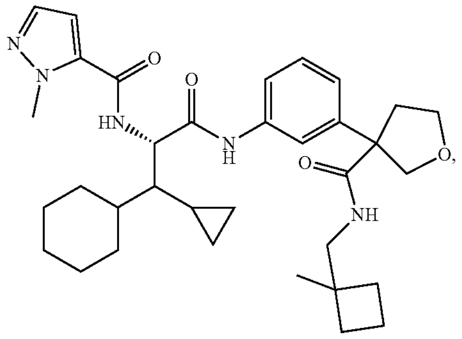
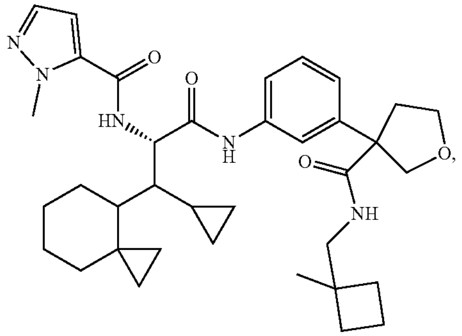
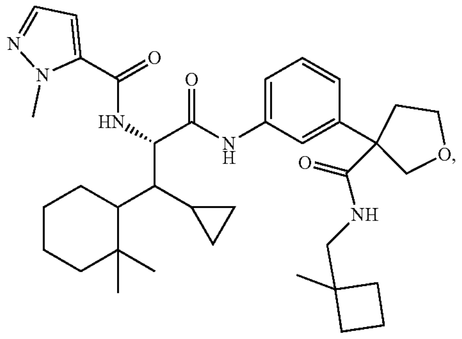
-continued
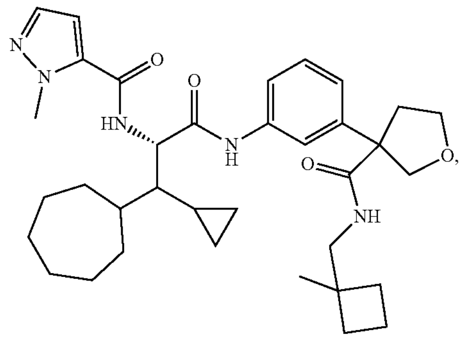
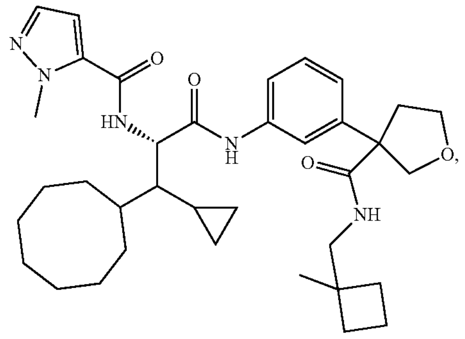
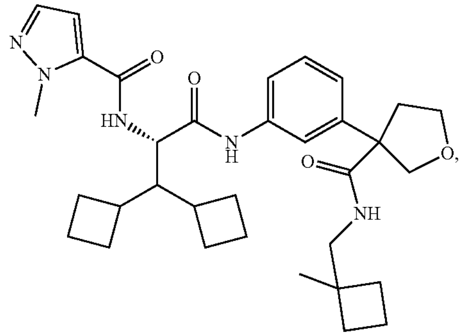
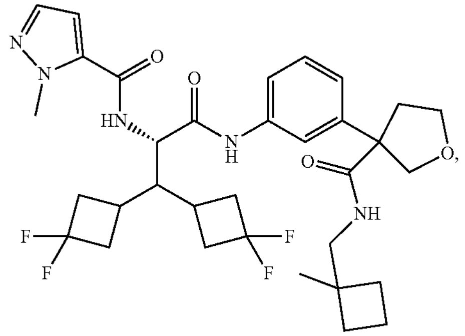
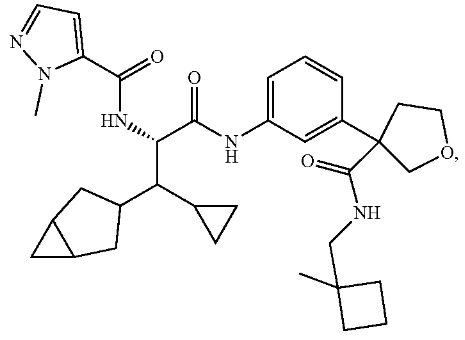

-continued
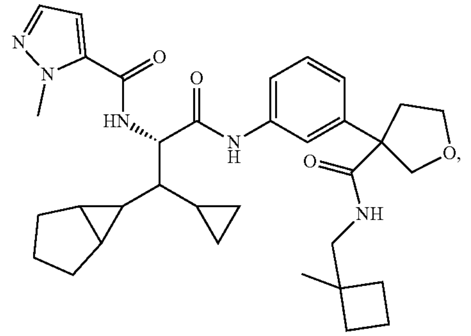
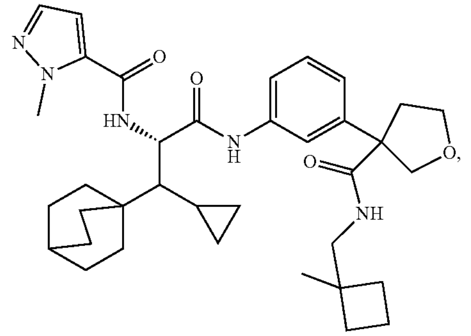
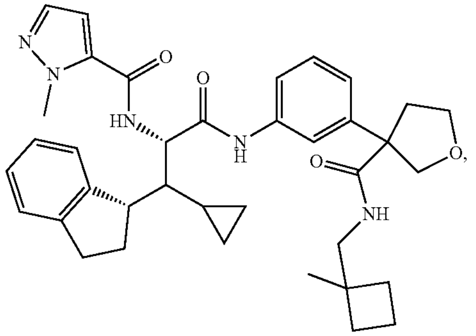
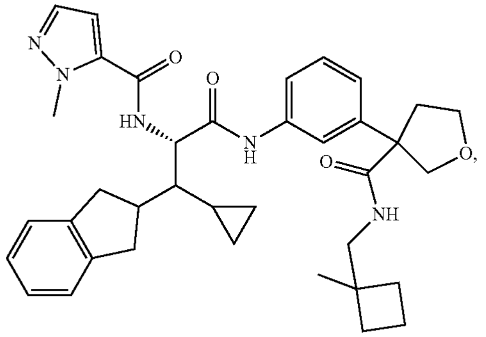
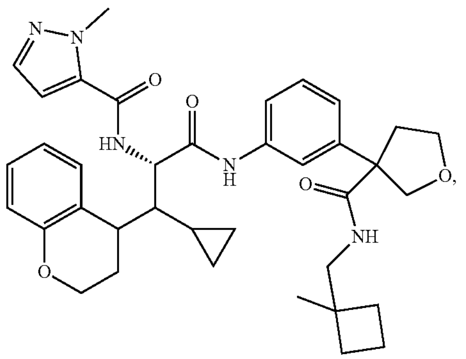
-continued
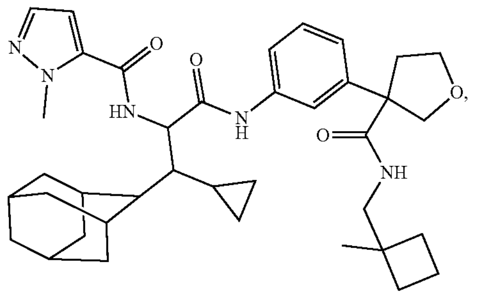
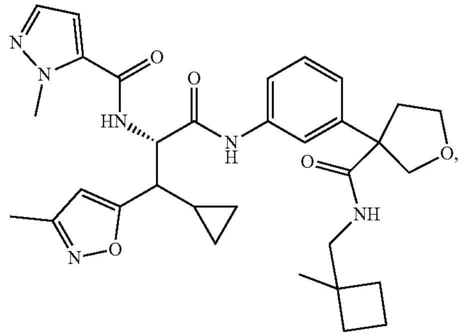
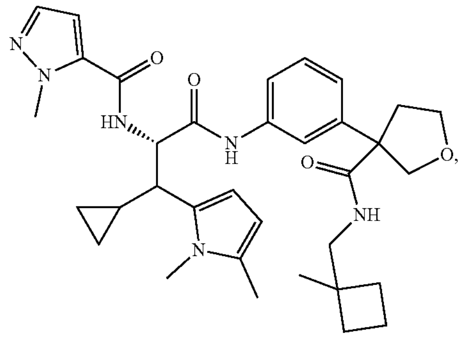
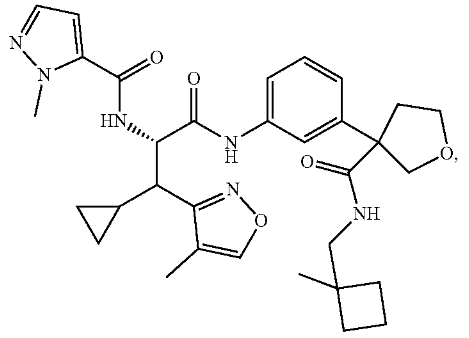
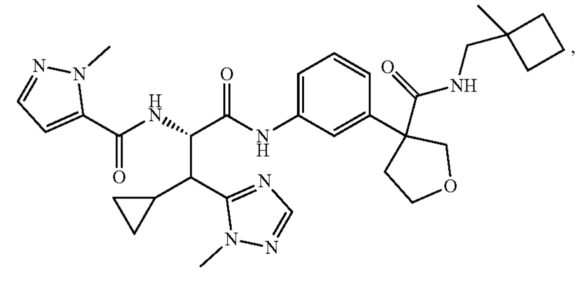

-continued
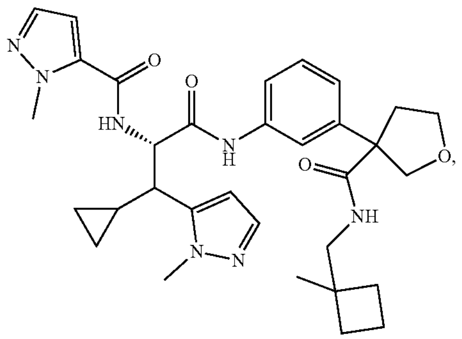
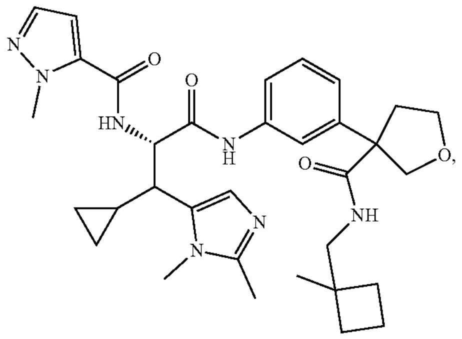
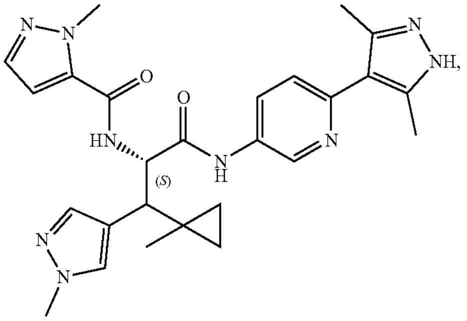
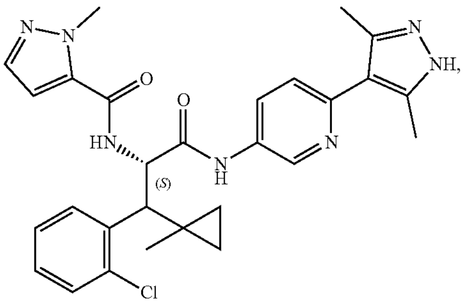
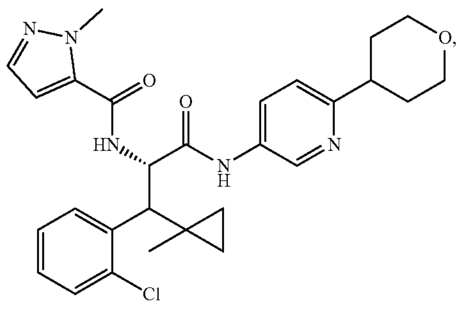
-continued
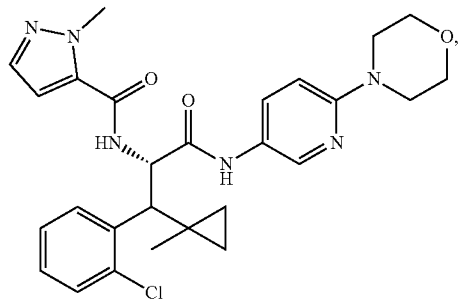
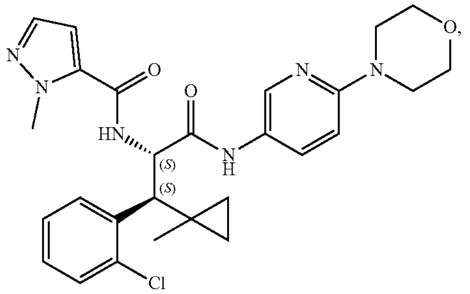
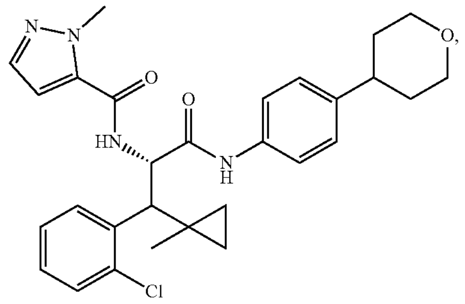
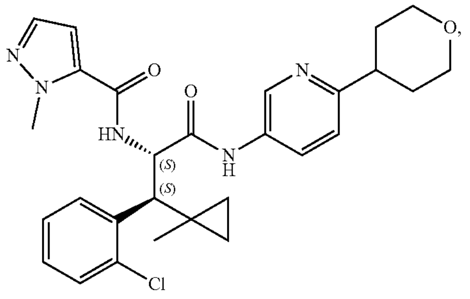
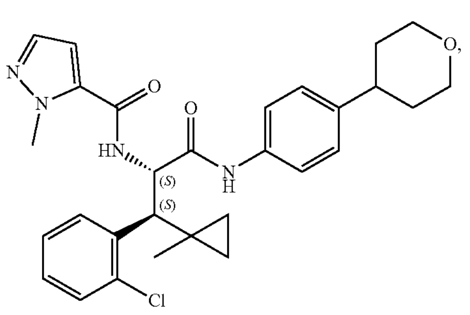

-continued

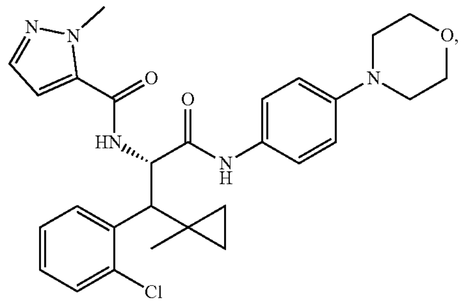

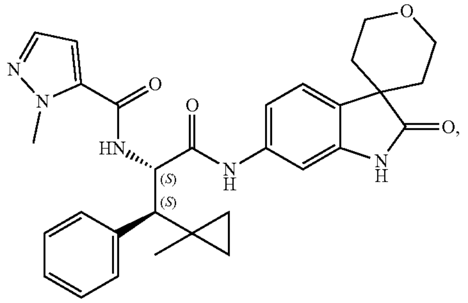

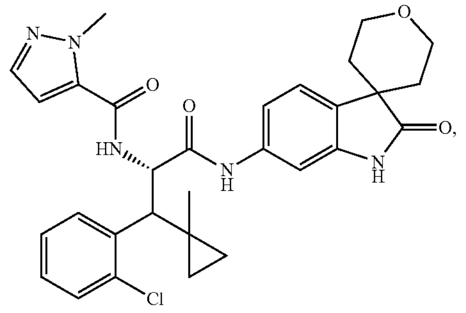

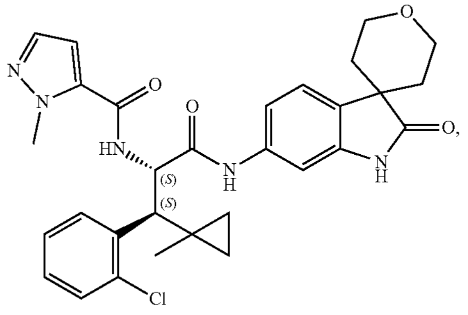

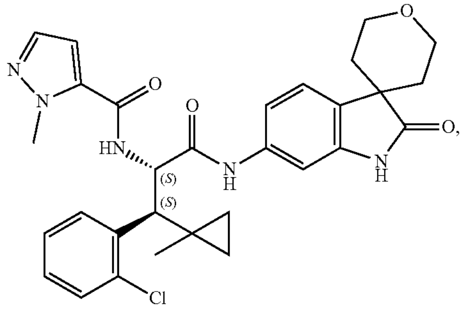

-continued

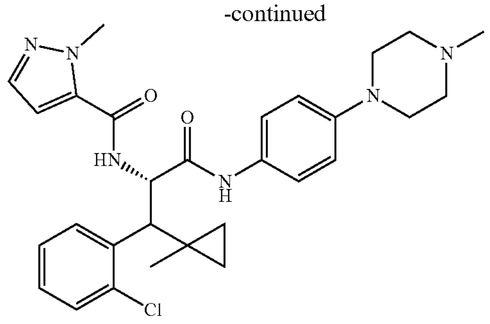

and

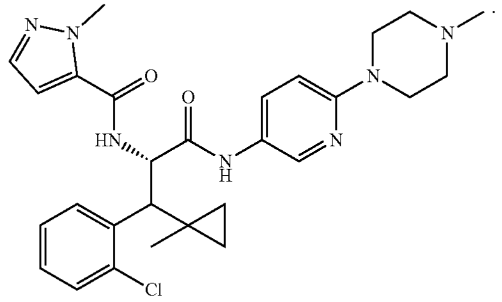

In a second aspect, this application provides a method for treating an interleukin-17 (IL-17)-mediated disease in a subject in need thereof, comprising:

administrating to the subject a therapeutically effective amount of the compounds mentioned above, or a deuterated compound, a stereoisomer, or a pharmaceutically acceptable salt thereof.

In an embodiment, the IL-17A-mediated disease is selected from the group consisting of inflammation, autoimmune diseases, infectious diseases, cancer, precancerous syndromes and a combination thereof.

In a third aspect, this application provides a pharmaceutical composition, comprising the compounds mentioned above or a deuterated compound, a stereoisomer, or a pharmaceutically acceptable salt thereof;

and a pharmaceutically-acceptable adjuvant.

In a fourth aspect, this application provides a method for treating an IL-17A-mediated disease in a subject in need thereof, comprising:

administrating to the subject a therapeutically effective amount of the compounds mentioned above, or a stereoisomer, a pharmaceutically acceptable salt, a solvate, a prodrug or a metabolite thereof.

IL-17A-mediated diseases as defined in this application are diseases in which IL-17A plays an important role in the pathogenesis of the disease. The main function of IL-17A is to coordinate local tissue inflammation, so as to play a role in various diseases. IL-17A-mediated diseases include one or more of inflammation, autoimmune diseases, infectious diseases, cancer, and precancerous syndrome-related diseases.

"Cancer" or "malignant tumor" refers to any of the diseases characterized by uncontrolled abnormal cell proliferation. Affected cells are any of the cells that have the ability to spread locally, or spread to other parts through blood and lymphatic system (i.e., metastasis), and characteristic structures and/or molecules.

"Cancer cell" refers to cells that undergo early, intermediate, or late stage of the multi-stage tumor progression. Cancers include sarcoma, breast cancer, lung cancer, brain cancer, osteocarcinoma, liver cancer, kidney cancer, colon cancer and prostatic cancer. In some embodiments, the compound of formula (I) is used to treat a cancer selected from the group consisting of colon cancer, brain cancer, breast cancer, fibrosarcoma and squamous cell carcinoma. In some embodiments, the cancer is selected from the group consisting of melanoma, breast cancer, colon cancer, lung cancer and ovarian cancer. In some embodiments, the cancer being treated is metastatic cancer.

Autoimmune diseases are caused by immune response of the body to substances and tissues that are normally present in the body. The autoimmune diseases include, for example, myocarditis, lupus nephritis, primary biliary cirrhosis, psoriasis, type 1 diabetes, Grave's disease, celiac disease, Crohn's disease, autoimmune neutropenia, juvenile arthritis, rheumatoid arthritis, fibromyalgia, Guillain-Barre syndrome, multiple sclerosis and autoimmune retinopathy. In some embodiments of this application, the treatment of autoimmune diseases such as psoriasis or multiple sclerosis is involved.

Inflammatory diseases include a variety of diseases characterized by characterized by histopathological inflammation. The inflammatory diseases include, for example, acne vulgaris, asthma, celiac disease, chronic prostatitis, glomerular nephritis, inflammatory bowel disease, pelvic inflammatory disease, reperfusion injury, rheumatoid arthritis, sarcoidosis, vasculitis, airway inflammation caused by house dust mites and interstitial cystitis. There is significant overlap between inflammatory diseases and autoimmune diseases. In some embodiments of this application, the treatment of the inflammatory disease such as asthma is involved. The immune system is often involved in inflammatory disorders, which can be manifested in allergic reactions and some myopathies, and many immune system disorders lead to abnormal inflammation. In addition, IL-17A-mediated diseases also include autoimmune inflammatory diseases.

The compounds provided herein and derivatives thereof can be named according to the IUPAC (International Union of Pure and Applied Chemistry) or CAS (Chemical Abstracts Services, Columbus, Ohio) naming system.

Unless otherwise specified, the initial definitions of a group or term used herein apply to that group or term throughout the specification. For terms without being specifically defined herein, those skilled in the art can understand their definitions based on the contents disclosed herein.

As used herein, term "substitution" means that one or more hydrogen atoms in a molecule are substituted with other different atoms or groups; or lone pair of electrons of the atoms in a molecule is substituted with other atoms or groups, for example, the lone pair of electrons on the S atom can be substituted with O atom to form

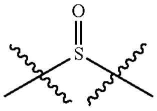
or
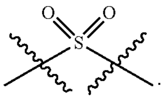
.

As used herein, term "may be further substituted with" means that "substitution" may but does not have to occur, including unsubstituted instance or substituted instance.

The minimum and maximum numbers of carbon atoms in a hydrocarbon group are indicated by a prefix, for example, a Ca-b alkyl indicates any alkyl group containing "a" to "b" carbon atoms. Therefore, for example, a $C_{1-6}$ alkyl refers to an alkyl containing 1-6 carbon atoms.

As used herein, term "alkyl" refers to a saturated hydrocarbon chain containing the specified number of atoms. Alkyl groups can be straight or branched. Representative branched alkyl groups have one, two or three branches. Alkyl groups may be optionally substituted with one or more substituents as defined herein. Alkyl groups include methyl, ethyl, propyl (n-propyl and isopropyl), butyl (n-butyl, isobutyl and tert-butyl), pentyl (n-pentyl, isopentyl and neopentyl) and hexyl. In addition, alkyl groups can also be part of other groups such as $—O(C_{1-6}$ alkyl).

As used herein, term "alkylene" refers to a divalent saturated aliphatic hydrocarbon group containing the specified number of atoms. A Ca-b alkylene refers to an alkylene group containing "a" to "b" carbon atoms. Alkylene groups include branched-chain hydrocarbyl groups and straight-chain hydrocarbyl groups. For example, term "propylene" can be exemplified by the structure of

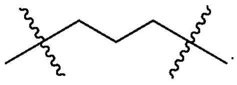 [SMILES: *CCC*]
.

Likewise, term "dimethylbutylene" for example, can be exemplified by any of the following structures of

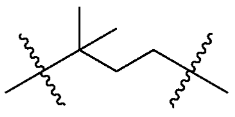
or
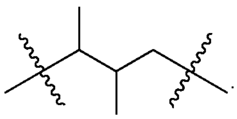
.

In this disclosure, a $—C_{0-2}$ alkylene group can be Co alkylene group, $C_1$ alkylene group (such as $—CH_2—$), $C_2$ alkylene group (such as $—CH_2CH_2—$). The $C_0$ alkylene group means that the group referred herein do not exist and the connection is realized by chemical bond, for example, A-$C_0$ alkylene-B refers to A-B, that is, the A group and the B group are directly connected by chemical bond.

As used herein, terms "cycloalkyl" and "cycloalkane" refer to a saturated group or a partially saturated cyclic group having carbon atoms and no heterocyclic atom and containing a monocyclic ring or a polycyclic ring (including fused ring and bridged ring). Terms "cycloalkyl", "cycloalkane" include cycloalkenyl groups such as cyclohexenyl. Cycloalkyl groups include, for example, adamantyl, cyclopropyl, cyclobutyl, cyclohexyl, cyclopentyl, cyclooctyl, cyclopentenyl, and cyclohexenyl. Cycloalkyl groups containing multiple bicycloalkyl systems are bicyclohexyl, bicyclopentyl, bicyclooctyl, and the like. Two bicycloalkyl polycyclic structures are exemplified and named as follows:

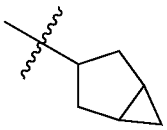 [SMILES: *C1CC2CC2C1]

bicyclohexyl and

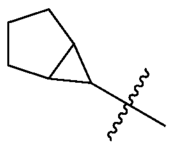 [SMILES: *C1C2CCCC12]

bicyclohexyl. "cycloalkyl" and "cycloalkane" further include a partially saturated cyclic group formed by fusing an aromatic ring with a non-aromatic ring, and the binding sites may be located at a non-aromatic carbon atom or an aromatic carbon atom, which includes 1,2,3,4-tetralin-5-yl and 5,6,7,8-tetralin-5-yl.

As used herein, term "unsaturated" means that groups or molecules contains carbon-carbon double bonds, carbon-carbon triple bonds, carbon-oxygen double bonds, carbon-sulfur double bonds, carbon-nitrogen triple bonds, etc. Those skilled in the art can freely select whether the unsaturated carbocyclic groups provided herein includes or does not include an aromatic ring group, and whether the unsaturated heterocyclic group includes and does not include a heteroaryl group.

As used herein, term "alkenyl" refers to straight-chain alkyl groups or branched-chain alkyl groups containing 2-10 carbon atoms (in some embodiments, containing 2 to 6 carbon atoms or 2 to 4 carbon atoms and having at least one site of unsaturated vinyl group (>C═C<)). For example, a (Ca-Cb) alkyl indicates an alkyl group containing "a" to "b" carbon atoms, such as vinyl, propenyl, isopropenyl, 1,3-butadienyl, and the like.

As used herein, term "alkynyl" refers to a straight-chain monovalent hydrocarbon group or a branched-chain monovalent hydrocarbon group containing at least one triple bond. Term "alkynyl" is also intended to include those hydrocarbon groups containing one triple bond and one double bond. For example, $(C_2$-$C_6)$alkynyl is intended to include ethynyl, propynyl, and the like.

As used herein, term "halogen" is fluorine, chlorine, bromine or iodine.

As used herein, terms "haloalkyl" and "halogen-substituted alkyl" mean that the hydrogen atoms in the alkyl group may be substituted with one or more halogen atoms. For example, a halogen-substituted $C_{1-4}$ alkyl group refers to an alkyl group containing 1 to 4 carbon atoms in which hydrogen atoms are substituted by one or more halogen atoms, which include monofluoromethyl group, difluoromethyl group and trifluoromethyl group.

As used herein, terms "heterocycloalkyl", "heterocycle", and "heterocycloalkane" refer to a saturated group or a partially saturated cyclic group containing at least one heteroatom and having a monocyclic ring or a polycyclic ring (including fused ring and bridged ring); Among them, the heteroatom refers to nitrogen atom, oxygen atom, sulfur atom and the like. A monovalent saturated or partially unsaturated monocyclic or bicyclic ring system are typical representatives of polycyclic ring atoms, containing 1-3 heterocyclic atoms independently selected from the group consisting of N, O and S, and the remaining ring atoms being carbon. Bicyclic ring consists of two rings that shares two atoms, i.e. the bridge separating the two rings is a single bond or a chain containing one or two heteroatoms. The monocyclic saturated heterocycloalkyl is, for example, oxetanyl, azetidinyl, pyrrolidinyl, 2-oxo-pyrrolidin-3-yl, tetrahydrofuroyl, tetrahydro-thienyl, pyrazolidinyl, imidazolidinyl, thiazolidinyl, piperidyl, tetrahydropyranyl, tetrahydrothiopyranyl, piperazinyl, morpholinyl,

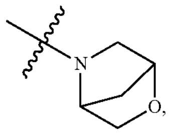 [SMILES: *N1CC2CC1CO2]

thiomorpholinyl, 1,1-dioxo-sulfur morpholin-4-yl, azepanyl, diazepanyl, homopiperazinyl or oxazepanyl. The bicyclic saturated heterocycloalkyl is, for example, 8-aza-bicyclo[3.2.1]octyl, quinuclidinyl, 8-oxa-3-aza-bicyclo[3.2.1]octyl, 9-aza-bicyclo[3.3.1]nonyl. The partially unsaturated heterocycloalkyl is dihydrofuranyl, imidazolinyl, tetrahydro-pyridyl or dihydropyranyl. Term "heterocycloalkyl" further includes the case where a partially saturated cyclic group formed by fusing an aromatic ring containing at least one heteroatom with a non-aromatic ring, and the binding sites may be located at a non-aromatic carbon atom, an aromatic carbon atom or a heteroatom, which include, for example, ■ ■ ■, ■ ■ ■, ■ ■ ■, ■ ■ ■ and ■ ■ ■.

As used herein, term "aromatic ring group" and "aromatic ring" refer to an aromatic hydrocarbon group containing multiple carbon atoms. Aryl groups are typically monocyclic, bicyclic or tricyclic aryl groups containing multiple carbon atoms. In addition, as used herein, the term "aryl" refers to an aromatic substituent which may be a single aromatic ring or multiple aromatic rings that are fused together, which include, for example, phenyl, naphthyl or tetrahydronaphthyl.

As used herein, term "stereoisomer" includes enantiomers and diastereomers.

In "—OR", "—NRR" etc. described herein, a R group is connected to an oxygen atom or a nitrogen atom by a single bond.

In "—C(O)R", "—$S(O)_2$R", etc. described herein, an oxygen atom is connected with a carbon atom or a sulfur atom by a double bond, and a R group is connected with a carbon atom or a sulfur atom by a double bond.

In "═O" and "═S" etc. described herein, an oxygen atom and a sulfur atom are connected to a substitution position through a double bond.

"- - -" and

""

in the groups mentioned herein are used to describe a position where a group is substituted.

As used herein, term "deuterated compound" means that one or more hydrogen atoms in a molecule or group are substituted with deuterated atoms, where a proportion of deuterated atoms is greater than the abundance of deuterated in nature.

As used herein, term "pharmaceutically acceptable" means that a carrier, a supporter, a diluent and an excipient and/or salts thereof are generally chemically or physically compatible with the other ingredients in the pharmaceutical preparation, and are physiologically compatible with the recipient.

As used herein, terms "salt" and "pharmaceutically acceptable salt" refer to a salt formed by the above-mentioned compound or stereoisomers thereof with an organic and/or inorganic acid and/or base, including acid salt, basic salt, zwitterionic salt (inner salt) and quaternary ammonium salt (such as alkylammonium salt). These salts can be directly obtained in the final separation and purification of the compound of this application, and can be also prepared by mixing the above compound or a stereoisomer thereof with an appropriate amount (such as equal equivalent) of an acid or a base. Specifically, these salts may be precipitated and collected by filtration, or recovered after evaporation of the solvent, or prepared by lyophilization. The salt described herein may be a hydrochloride, sulfate, citrate, benzenesulfonate, hydrobromide, hydrofluorate, phosphate, acetate, propionate, succinate, oxalate, malate, fumarate, maleate, tartrate or trifluoroacetate of the compound.

In some embodiments, the compounds mentioned in this disclosure can be used in combination with each other, or used in combination with any other active agents to prepare a medication or a pharmaceutical composition for regulating cell function or treating a disease. In the case of using a group of compounds, these compounds can be simultaneously, separately or sequentially administered to the subject.

Obviously, based on the common technical knowledge and conventional means in the art, various modifications, replacements and variations can be made without departing from the spirit of this application, which should fall within the scope of the application.

This application will be further described below with reference to the embodiments, and these embodiments are not intended to limit this application. Any technologies implemented based on the above-mentioned description shall fall within the scope of this application.

DETAILED DESCRIPTION OF EMBODIMENTS

Figure 1A:
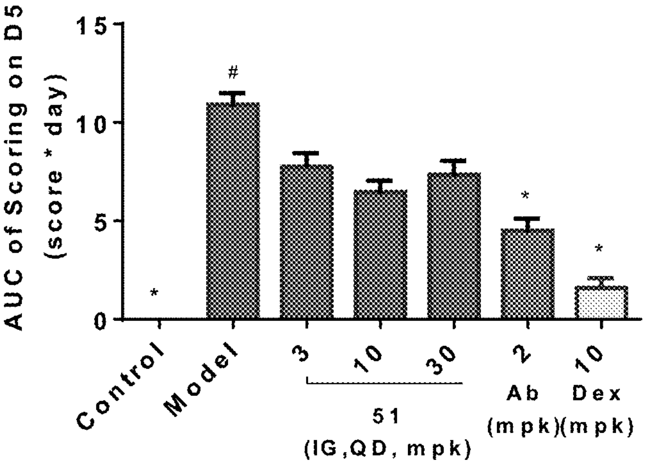
FIGS. 1A-D show efficacy test results of compound 51 in an imiquimod-induced psoriasis mouse model.

Compounds are structurally identified by nuclear magnetic resonance (NMR) and mass spectrometry (MS), where the NMR shift (δ) is expressed by ppm ($10^{-6}$); the NMR analysis is carried out by using Bruker AvanceIII 400 and Bruker Avance 300; the solvents include dimethyl sulfoxide-d6 (DMSO-d6), chloroform-d ($CDCl_3$) and methanol-d ($CD_3OD$); and tetramethylsilane (TMS) is adopted as an internal standard.

LC-MS analysis is performed using Shimadzu LC-MS 2020 (ESI). HPLC analysis is performed using Shimadzu LC-20A. MPLC (medium pressure preparative liquid chromatography) is performed using a Gilson GX-281 reversed-phase preparative chromatographic instrument. Thin-layer chromatography employs HSGF254 (Yantai Huanghai Co. Ltd) or GF254 (Qingdao Haiyang Co. Ltd) silica gel plate with a thickness of 0.4-0.5 mm. Column chromatography employs 200-300 mesh silica gel (Yantai Huanghai Co. Ltd) as the carrier.

The known starting materials used herein can be synthesized using the methods known in the art, or purchased from manufactures such as Energy Chemical Co., Chengdu Kelong Chemical Co., Ltd., Accela ChemBio Co., Ltd., and J&K Scientific Ltd.

Unless otherwise specified, the reaction is carried out at room temperature under nitrogen atmosphere; the solutions mentioned below are all aqueous solutions; and M indicates mol/L.

Abbreviations of some chemical reagents used herein are listed as follows: triethylamine (TEA or $Et_3N$); N,N-diisopropylethylamine (DIPEA); 1-hydroxybenzotriazole (HOBt); dichloromethane (DCM); petroleum ether (PE); ethyl acetate (EA or EtOAc); tetrahydrofuran (THF); N,N-dimethylformamide (DMF); N-methylpyrrolidone (NMP); N-methylmorpholine oxide (NMO); Methanol (MeOH); ethanol (EtOH); dimethyl sulfoxide (DMSO); trifluoroacetic acid (TFA); sodium borohydride ($NaBH_4$); methanesulfonyl chloride (MsCl); diisobutylaluminium hydride (DIBAL); N-Bromosuccinimide (NBS); N-Chlorosuccinimide (NCS); dimethyl sulfide (DMS); N-(Benzyloxycarbonyloxy) succinimide (CbzOSu); diethylzinc (ZnEt2); palladium (Pd/C); diisopropyl azodicarboxylate (DIAD); diethyl azodicarboxylate (DEAD); triphenylphosphine ($PPh_3$); oxalyl chloride ($(COCl)_2$); n-Butyllithium (n-BuLi); titanium ethoxide ($Ti(OEt)_4$); trimethylsilyl cyanide (TMSCN); caesium fluoride (CsF); methyl tert-butyl ether (MTBE); hydrogen peroxide ($H_2O_2$); di-tert-butyl dicarbonate ($(Boc)_2O$); 2-(trimethylsilyl) ethoxymethyl chloride (SEMCl); sodium hydride (NaH); chloroiodomethane ($ICH_2Cl$); phosphorus tribromide ($PBr_3$); paraformaldehyde ($(CH2O)_n$); diisopropylamine trifluoroacetate (TFA·PrNH); 2-(7-azobenzotriazole)-tetramethylurea hexafluorophosphate (HATU); 1-hydroxy-7-azobenzotriazole (HOAT); O-Benzotriazole-N,N,N',N'-tetramethylurea hexafluorophosphate (HBTU); propylphosphonic anhydride (T3P); benzotriazole-1-yl-oxytripyrrolidinophosphonium hexafluorophosphate (PyBOP); dicyclohexylcarbodiimide (DCC); 1-(3-dimethylaminopropyl)-3-ethylcarbodiimide hydrochloride (EDC or EDCI); and 9-fluorenylmethyl-N-succinimide carbonate (Fmoc-Osu).

Preparation of Intermediate 1

The intermediate I was prepared through the following route:

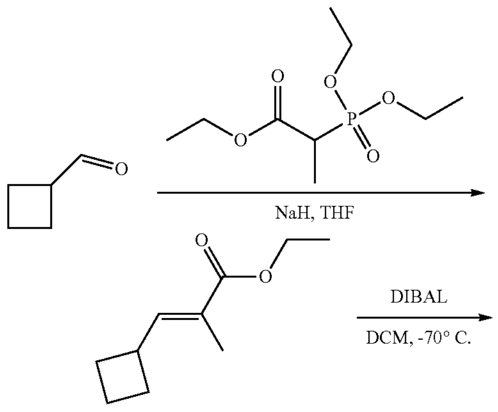

1-1

-continued

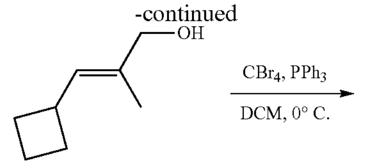

1-2

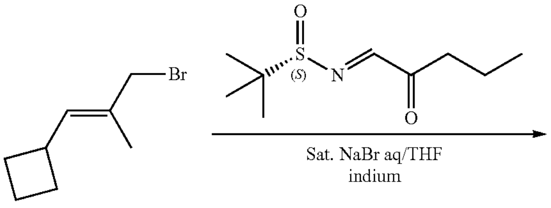

1-3

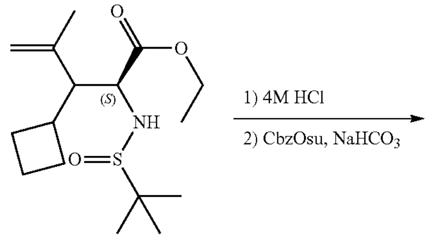

1-4

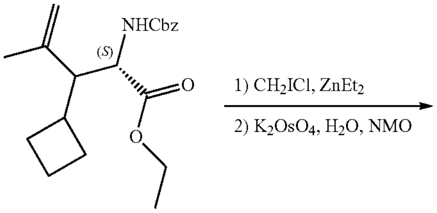

1-5

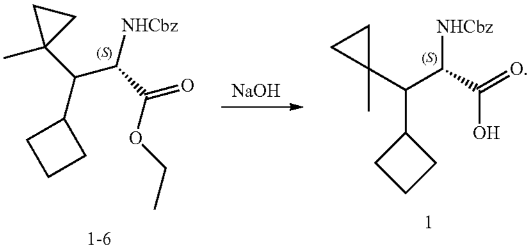

1-6 1

Step 1 Preparation of Intermediate 1-1

To a dispersion of 251.65 mg of NaH (10.49 mmol) in 25 mL of THE under ice bath was dropwise added 2.04 g of triethyl 2-phosphonopropionate (10.49 mmol). The reaction mixture was stirred at 0° C. for 20 min and dropwise added with 840 mg of cyclobutanecarboxaldehyde (9.99 mmol). Then the reaction mixture was restored to room temperature, stirred overnight for reaction, quenched with saturated ammonium chloride and subjected to extraction with ethyl acetate. The organic phases were combined and subjected to rotary evaporation to obtain a crude product, which was further purified by silica gel column chromatography to obtain 1.6 g of the intermediate 1-1 (9.51 mmol) with a yield of 95.24%.

Step 2 Preparation of Intermediate 1-2

To a solution of 9.0 g of the intermediate 1-1 (53.50 mmol) in 60 mL of DCM at −70° C. was dropwise added 15.11 g of DIBAL (107.00 mmol, 18.93 mL). The reaction mixture was reacted at −70° C. for 2 h. When the reaction was confirmed by thin-layer chromatography (TLC) to be complete, the reaction mixture was quenched with water, and filtered to obtain a filtrate. Once the organic phase and the aqueous phase in the filtrate were separated, the organic phase was transferred to rotary evaporation to obtain a crude product, which was further purified by silica gel column chromatography to give 5.6 g of the intermediate 1-2 (44.38 mmol) with a yield of 82.95%.

Step 3 Preparation of Intermediate 1-3

To a solution of 1.5 g of the intermediate 1-2 (12.12 mmol) in 60 mL of DCM at −70° C. was added 4.57 g of $CBr_4$ (13.94 mmol), and then dropwise added a solution of 3.33 g of $PPh_3$ (127.30 mmol) in 5 mL of DCM. The reaction mixture was stirred at 0° C. for 1 h, and filtered to collect a filtrate, which was concentrated to obtain a crude product, which was purified by silica gel column chromatography (eluent: petroleum ether) to obtain 2.2 g of the intermediate 1-3 (11.6 mmol) with a yield of 95.96%.

Step 4 Preparation of Intermediate 1-4

To a solution of 1.4 g of the intermediate 1-3 (7.40 mmol) and 507 mg of ethyl (2Z)-2-[(S)-tert-butylsulfinyl]iminoacetate) (2.47 mmol) in 15 mL of THF at room temperature was added 679.68 mg of Sat.NaBr·$H_2O$ (2.59 mmol, 30 mL), and then added 1.13 g of indium powder (9.87 mmol). The reaction mixture was stirred at room temperature under nitrogen protection overnight, and filtered to collect a filtrate, which was diluted with water and subjected to extraction with ethyl acetate. The organic phases were combined, washed with NaCl solution, dried with anhydrous sodium sulfate, filtered, and concentrated to obtain a crude product (770 mg, 2.44 mmol), which was used directly in the next reaction without purification.

MS m/z: 316 $(M+1)^+$.

Step 5 Preparation of Intermediate 1-5

To a solution of 150 mg of intermediate 1-4 (475.48 μmol) in 1.6 mL of methanol under ice bath was dropwise added 0.5 mL of HCl/EA (4 M). The reaction mixture was stirred at room temperature for 1 h, and concentrated. The crude product was dissolved in a mixture of 2 mL of THF and 2 mL of water, added with 79.88 mg of $NaHCO_3$ (950.96 μmol) and 118.50 mg of CbzOSu (475.48 μmol) in sequence, stirred at room temperature for 30 min, diluted with water, and subjected to extraction with ethyl acetate. The organic phase was collected, dried with anhydrous sodium sulfate, filtered and concentrated to obtain a crude product, which was separated and purified by silica gel column chromatography to give 20 mg of intermediate 1-5 (57.90 μmol) with a yield of 12.18%.

MS m/z: 346 $(M+1)^+$.

Step 6 Preparation of Intermediate 1-6

To a solution of 500 mg of the intermediate 1-5 (1.45 mmol) in 10 mL of dry dichloromethane under nitrogen protection at room temperature was added 1.1 mL of $CH_2ICl$. The reaction mixture was cooled to −20° C.~−25° C., dropwise added with 8.7 mL of ZnEt2, and stirred at room temperature overnight.

The reaction mixture was quenched with saturated ammonium chloride, and subjected to extraction with ethyl acetate. The organic phases were combined and concentrated to obtain a crude product, in which there was still about 10% of the intermediate 1-5. The crude product was dissolved in a mixture of MeOH/THF/$H_2O$ (1/1/1, a total of 150 mL), added with 70 mg of $K_2OsO_4$ (0.19 mmol) and 0.5 mmol of NMO, and stirred at room temperature overnight for reaction. After the reaction was completed, the reaction mixture was concentrated, diluted with water, and subjected to extraction with ethyl acetate. The organic phases were combined and washed with water and saturated NaCl solution, and concentrated to obtain a crude product, which was separated and purified by silica gel column chromatography to obtain 313 mg of the intermediate 1-6 with a yield of 59%.

MS m/z: 360 $(M+1)^+$.

$^1H$ NMR (400 MHz, Chloroform-d) δ 7.38-7.29 (m, 5H), 5.11 (s, 2H), 4.48 (dd, J=9.7, 6.1 Hz, 1H), 4.22-4.06 (m, 2H), 2.64-2.46 (m, 1H), 2.03 (d, J=8.5 Hz, 1H), 2.00-1.75 (m, 3H), 1.75-1.62 (m, 3H), 1.27 (t, 3H), 0.92 (s, 3H), 0.30-0.09 (m, 4H).

Step 7 Preparation of Intermediate 1

To a solution of 420 mg of the intermediate 1-6 (1.17 mmol) in THF (2 mL)/MeOH (2 mL)/$H_2O$ (2 mL) was added 147.22 mg of LiOH $H_2O$ (3.51 mmol). The reaction mixture was stirred at room temperature overnight, and concentrated under reduced pressure. The crude product was diluted with water, adjusted to pH 4-6 with 6 N dilute hydrochloric acid, and subjected to extraction with dichloromethane. The organic phases were combined, dried with anhydrous sodium sulfate, filtered and concentrated to obtain 340 mg of the intermediate 1 (1.03 mmol) with a yield of 87.80%.

MS m/z: 332 $(M+1)^+$.

Preparation of Intermediate 2

The intermediate 2 was prepared through the following route:

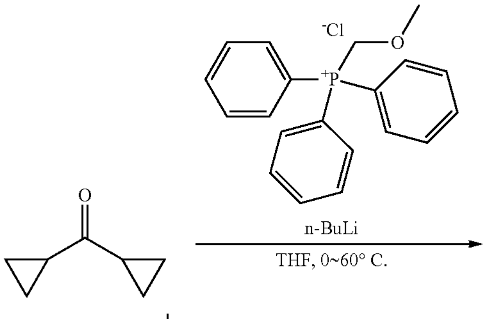

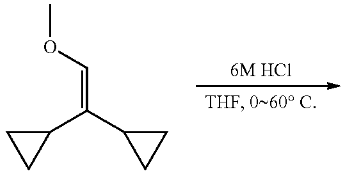

2-1

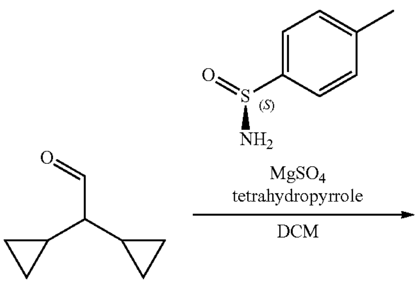

2-2

-continued

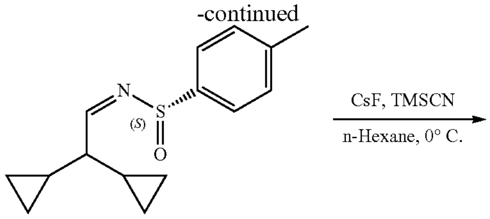

2-3

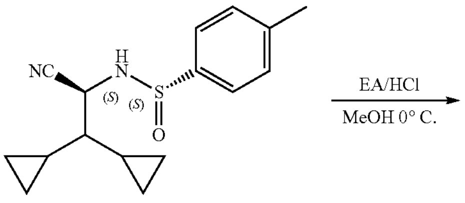

2-4

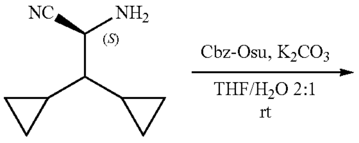

2-5

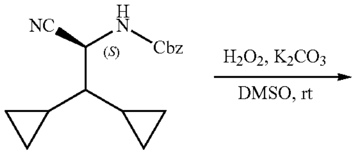

2-6

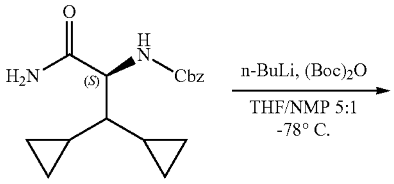

2-7

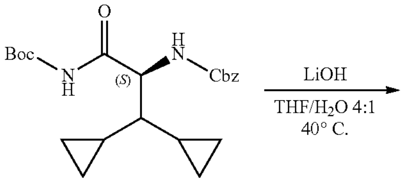

2-8

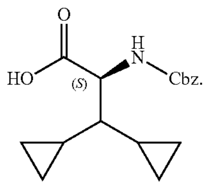

2

Step 1 Preparation of Intermediate 2-1

To a solution of 300 g of (methoxymethyl)triphenylphosphonium chloride (4.09 mol) in 2.4 L of THE under ice bath and nitrogen protection was dropwise added n-BuLi (2.5 M in hexane, 4.09 mol, 1.63 L). The reaction mixture was stirred at 0° C. for 1 h. When turned dark brown, the reaction mixture was dropwise added with a solution of 300 g of dicyclopropyl ketone (2.72 mol) in 0.6 L of THF. The reaction mixture was heated to 60° C. and stirred for 4 h. After the reaction completed, the reaction mixture was cooled to room temperature, quenched with a 30% $NH_4Cl$ aqueous solution, subjected to extraction with ethyl acetate. The organic phases were combined and washed with saturated NaCl solution, dried with anhydrous sodium sulfate, filtered and subjected to rotary evaporation to obtain the crude product, which was subjected to reduced pressure distillation for separation and purification, so as to give 279 g of the intermediate 2-1 with a yield of 74.2%, which was in a clarified oil state.

Step 2 Preparation of Intermediate 2-2

To a solution of 279 g of the intermediate 2-1 (2.02 mol) in 1.7 L of THF was added 1.7 L of 6M HCl under ice bath. The reaction mixture was heated to 60° C. and stirred at 60° C. for 5 h. After the reaction completed, the reaction mixture was subjected to extraction with ethyl acetate. The organic phases were combined, dried and concentrated to give a crude product of 239.6 g of the intermediate 2-2, which was in a clarified oil state. The crude product was directly used in the next reaction without further purification.

Step 3 Preparation of Intermediate 2-3

239 g of the crude product of the intermediate 2-2 (1.92 mol, based on 100% purity), 299 g of (S)-4-methylbezenesulfinamide (1.92 mol), 697 g of magnesium sulfate (5.79 mol), 2.5 L of DCM and 13.73 g of tetrahydropyrrole (0.193 mol) were mixed in a 5 L three-necked flask. The reaction mixture was stirred at room temperature overnight for reaction, concentrated by reduced pressure distillation at 40° C., and added with petroleum ether followed by beating and filtration to obtain a filtrate. The filtrate was concentrated, and separated and purified by silica gel column chromatography (eluent: PE/EA=10/1) to give 217 g of the intermediate 2-3 (0.83 mol) with a yield of 43%.

MS m/z: 262 $(M+1)^+$.

Step 4 Preparation of Intermediate 2-4

To a solution of 217 g of the intermediate 2-3 (0.83 mol) in 2 L of n-hexane was added with 252 g of CsF (1.66 mol). The reaction mixture was cooled to 0° C. under nitrogen protection, and then dropwise added with 165 g of TMSCN (1.66 mol). The reaction mixture was restored to room temperature and stirred overnight for reaction. After the reaction completed, the reaction mixture was concentrated, and subjecting to beating with n-hexane and filtration 2 times. The solids were concentrated under reduced pressure to give 168 g of the intermediate 2-4 (0.58 mol).

MS m/z: 289 $(M+1)^+$.

Step 5 Preparation of Intermediate 2-5

84 g of the intermediate 2-4 (2.92 mol) was dissolved in 840 mL of MeOH solution. The reaction mixture was added with HCl/EA (4M, 146 ml, 0.583 mol) under ice bath, and stirred for 2 h. After the reaction completed, the reaction mixture was concentrated to obtain a crude product, which was beaten and washed several times with petroleum ether, followed by filtration and drying to give 54.4 g of the intermediate of 2-5, which was directly used in the next reaction without purification.

MS m/z: 187 $(M+1)^+$.

Step 6 Preparation of Intermediate 2-6

100 g of $K_2CO_3$ (0.73 mol) and 87.4 g of (Boc) 20 (0.35 mol) were added to a mixed solution of 54.4 mg of the intermediate 2-5 (0.292 mol, based on 100% purity) in THF (300 mL)/$H_2O$ (300 mL). The reaction mixture was stirred at 25° C. for 2 h. After the reaction completed, the reaction mixture was subjected to extraction with ethyl acetate. The organic phases were combined and concentrated to obtain a crude product, which was separated and purified by silica gel column chromatography (eluent: PE/EA=5/1) to give 75.4 g of the intermediate 2-6 (0.264 mol) with a yield of 90.8%, which was in a white solid state.

MS m/z: 285 $(M+1)^+$.

Step 7 Preparation of Intermediate 2-7

To a solution of 75.4 g of the intermediate 2-6 (0.264 mol, based on 100% purity) in 750 mL of DMSO solution was added 54.9 mg of $K_2CO_3$ (0.398 mol). The reaction mixture was cooled to 10° C., and then $H_2O_2$ (content of 30%, 90 g, 0.79 mol), the reaction mixture was stirred at 25° C. overnight for reaction. After the reaction completed, the reaction mixture was diluted with water, subjected to extraction with ethyl acetate. The organic phases were combined and concentrated to obtain 73.5 g of the intermediate 2-7 solid, which was directly used in the next reaction without purification.

MS m/z: 303 $(M+1)^+$.

Step 8 Preparation of Intermediate 2-8

To a mixed solution of 73.5 g of the intermediate 2-7 (0.24 mol, based on 100% purity) in THF (500 mL)/NMP (150 mL) was dropwise added 204 mL of n-BuLi (0.5 mol, 2.5 M in hexane) at −78° C. under nitrogen protection. The reaction mixture was stirred at −78° C. for 1 h, added with a solution of 57.5 mg of (Boc) 20 (0.26 mol) in 250 mL of THE, and stirred for 1 h. After the reaction completed, the reaction mixture was quenched with cold $NH_4Cl$, (30% w/v) aqueous solution, and subjected to extraction with ethyl acetate, and concentrated to obtain 86 g of the crude product of intermediate 2-8, which was directly used in the next reaction without further purification.

MS m/z: 403 $(M+1)^+$.

Step 9 Preparation of Intermediate 2

To a mixed solution of 86 g of the intermediate 2-8 (0.21 mol, based on 100% purity) in MeOH (800 mL)/$H_2O$ (200 mL) was added 17.4 g of LiOH (0.426 mol). The reaction mixture was heated to 60° C. and stirred at 60° C. overnight for reaction. After the reaction completed, the reaction mixture was distilled under reduced pressure to remove solvents. The crude product of the intermediate 2 was dissolved in water, subjected to extraction with ethyl acetate to obtain a filtrate. The aqueous phase was adjusted to pH 2-3 with 6M HCl, subjected to extraction with ethyl acetate, and concentrated to obtain a product. The product was separated and purified by column chromatography to give 48 g of the intermediate 2 (0.158 mol) with a three-step yield of 75.1%.

MS m/z: 304 $(M+1)^+$; chiral purity: 98%.

Preparation of Intermediate 3

The intermediate 3 was shown as follows:

3

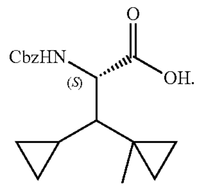

Similarly, cyclopropanecarboxaldehyde was used as a starting material. The intermediate 3 was prepared according to the synthetic route of the intermediate 1.

MS m/z: 318 $(M+1)^+$.

Preparation of Intermediate Z2

The intermediate Z2 was prepared through the following route:

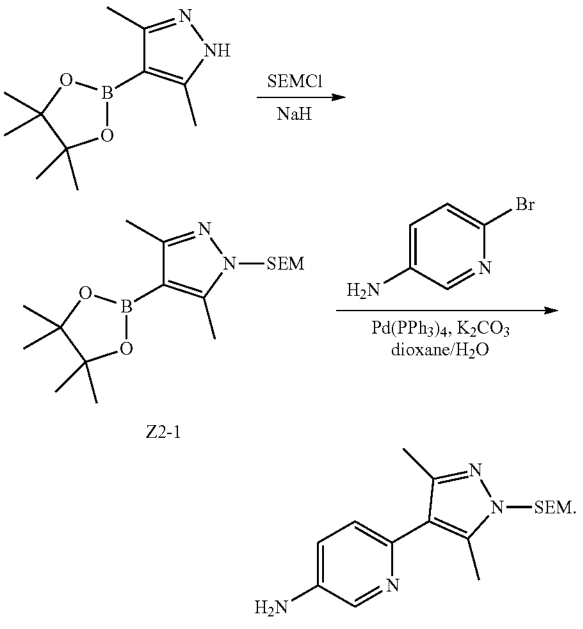

Z2-1

Z2

Step 1 Preparation of Intermediate Z2-1

To a solution of 50 g of 3,5-dimethylpyrazole-4-boronic acid pinacol ester (225.13 mmol) in 800 mL of DMF under ice bath was added 13.51 g of NaH (337.70 mmol, 60% purity). The reaction mixture was stirred at 0° C. for 1 h and dropwise added with 39.48 g of SEMCl (236.39 mmol) at 0° C. The reaction mixture was restored to room temperature and stirred for 20 h, and then quenched with water, subjected to extraction with ethyl acetate, washed with NaCl solution, and dried with anhydrous sodium sulfate. The organic phases were combined and subjected to rotary evaporation to obtain a crude product. The crude product was further purified by silica gel column chromatography to obtain 73.5 g of the intermediate Z2-1 (208.60 mmol) with a yield of 92.66%. MS m/z: 353 $(M+1)^+$.

Step 2 Preparation of Intermediate Z2

To a mixed solution of 3 g of 6-bromo-3-aminopyridine (17.34 mmol) in dioxane (75 mL)/H2O (15 mL) was added 10.47 g of the intermediate Z2-1 (20.81 mmol), 4.79 g of $K_2CO_3$ (34.68 mmol) and 1.20 g of $Pd(PPh_3)_4$ (1.04 mmol). After nitrogen replacement, the reaction mixture was heated to 90° C. under nitrogen protection, and stirred overnight for reaction. After the reaction completes, the reaction mixture was quenched with NaCl solution, subjected to extraction with ethyl acetate. The organic phases were combined and washed with saturated NaCl solution, dried with anhydrous sodium sulfate, filtered to collect a filtrate, which was concentrated to obtain a crude product, which was further purified by silica gel column chromatography (ethyl acetate/petroleum ether/dichloromethane=1/2/1, v/v/v) to give 5.1 g of the intermediate Z2 (12.81 mmol) with a yield of 73.88%. MS m/z: 319 $(M+1)^+$.

$^1H$ NMR (400 MHz, Chloroform-d) § 8.32 (s, 1H), 7.16 (d, 2H), 5.40 (s, 2H), 3.62 (t, J=8.9, 7.6 Hz, 2H), 2.44 (s, 3H), 2.33 (s, 3H), 0.93 (t, 2H).

Preparation of intermediate Z3

The intermediate Z3 was shown as follows:

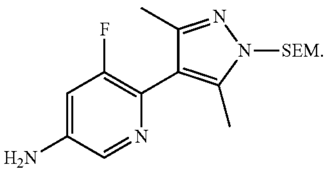

Z3

Referring to the synthetic scheme of the intermediate Z2, in step 2, the reagents are the same except that the 6-bromo-3-aminopyridine was substituted with 5-amino-2-bromo-3-fluoropyridine, such that the intermediate Z3 can be obtained. MS m/z: 337 $(M+1)^+$.

$^1H$ NMR (400 MHz, Chloroform-d) δ 8.18 (s, 1H), 6.92 (d, J=10.7 Hz, 1H), 5.40 (s, 2H), 3.63 (t, 2H), 2.33 (s, 3H), 2.24 (s, 3H), 0.92 (t, 2H), 0.00 (s, 9H).

Example 1 Preparation of Compound 1 (General Route A)

The general route A was shown as follows:

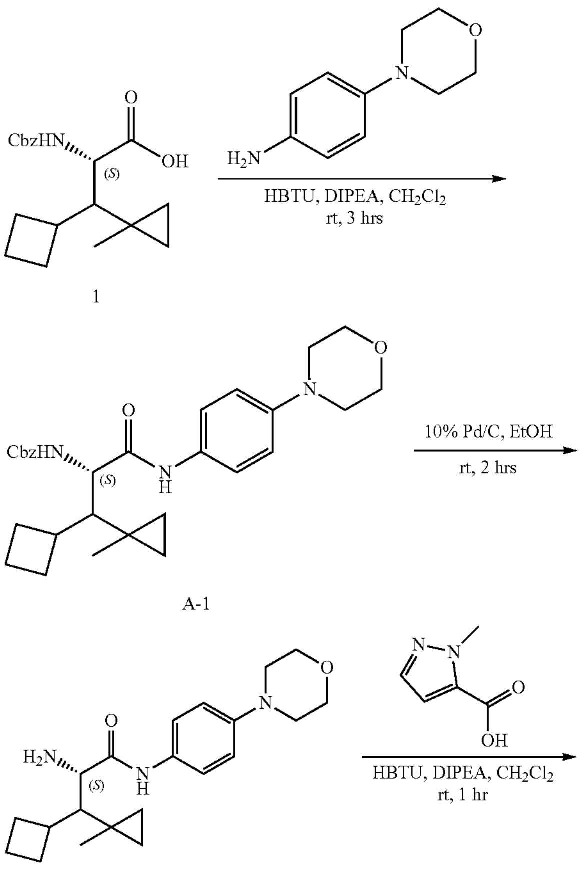

1

A-1

A-2

-continued

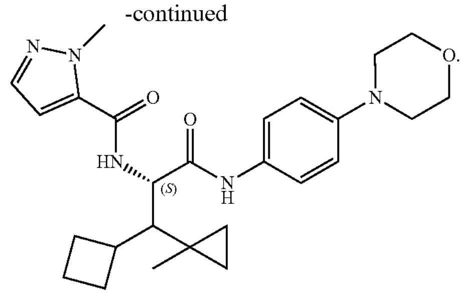

Example 1

Step 1 Preparation of Intermediate A-1

500 mg of the intermediate 1 (1.61 mmol), 731.2 mg of HBTU (1.93 mmol), 622.2 mg of DIPEA (4.82 mmol) were added to a 100 mL single-necked flask, and dissolved in 16 mL of $CH_2Cl_2$. The reaction mixture was stirred at room temperature for 10 min, added with 314.8 mg of 4-morpholinoaniline (1.77 mmol) at room temperature, and reacted under stirring at room temperature for 3 h. After that, the reaction mixture was added with 30 mL of water, and subjected to extraction with $CH_2Cl_2$ (30 mL*2). The organic phases were combined, washed with saturated NaCl (30 mL*2), dried with anhydrous sodium sulfate, filtered, and concentrated under reduced pressure. The residue was separated and purified by silica gel column chromatography to obtain 592 mg of the intermediate A-1 (1.21 mmol) with a yield of 75%.

MS m/z: 492.0 $(M+1)^+$.

Step 2 Preparation of Intermediate A-2

To a 100 mL single-necked flask was added 592 mg of the intermediate A-1 (1.21 mmol) and 20 mL of EtOH, and added 180 mg of Pd/C (50% (w/w)) under stirring in the nitrogen protection at room temperature. The reaction mixture was reacted under stirring at room temperature in the presence of hydrogen for 2 h, filtered, and concentrated under reduced pressure to obtain 430 mg of the intermediate A-2 (1.20 mmol) with a yield of 98%.

MS m/z: 358.0 $(M+1)^+$.

Step 3 Preparation of Compound 1

10.59 mg of 1-methylpyrazole-5-carboxylic acid (0.084 mmol), 38.20 mg of HBTU (0.10 mmol), 32.51 mg of DIPEA (0.25 mmol) were added to a 25 mL single-necked flask, and dissolved in 2 mL of $CH_2Cl_2$. The reaction mixture was reacted under stirring at room temperature for 10 min, added with 30 mg of the intermediate A-2 (0.084 mmol) at room temperature, and then reacted under stirring at room temperature for 1 h. After that, the reaction mixture was added with 5 mL of water, and subjected to extraction with $CH_2Cl_2$ (5 mL*2). The organic phases were combined, dried with anhydrous sodium sulfate, filtered, and concentrated under reduced pressure. The residue was separated and purified by MPLC (ACN/$H_2O$, 0.05% FA) to give 23.83 mg of the compound 1 with a yield of 61%.

MS m/z: 466.0 $(M+1)^+$.

Examples 2-23 Preparation of Compounds 2-23

Compounds 2-23 were synthesized through the general route A in combination with operation steps described in Example 1. Briefly, in step (1), the 4-(4-morpholinyl) aniline used in Example 1 was replaced with other arylamines to undergo condensation with the intermediate 1; in step (2), the benzyloxycarbonyl (Cbz) protecting group was removed by Pd/C-catalyzed hydrogenation; and in step (3), the hydrogenated product underwent condensation with 1-methyl-5-pyrazolecarboxylic acid.

| Examples | Formula | Arylamine reactant | $^1$H NMR and/or LC-MS: |
|---|---|---|---|
| 2 | 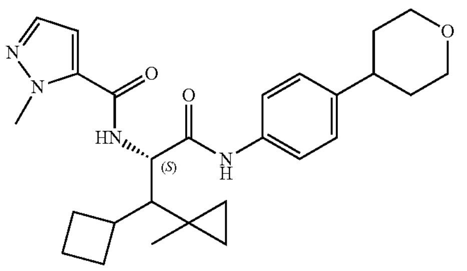 | 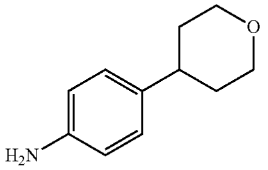 | MS m/z: 465 $(M + 1)^+$. |
| 3 | 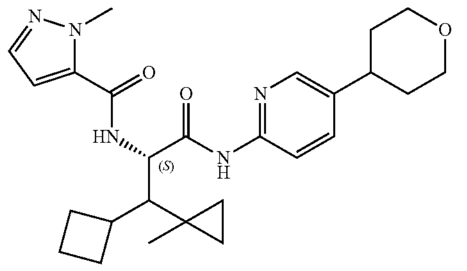 | 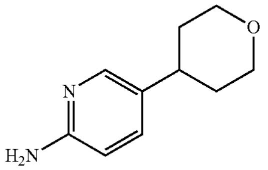 | $^1$H NMR (400 MHz, Methanol-$d_4$) δ 0.28 (4H, m, J = 11.89 Hz), 1.08 (3H, s), 1.42 (1H, t, J = 10.10 Hz), 1.71 (1H, q, J = 5.76 Hz), 1.98 (8H, m, J = 8.87 Hz), 2.66 (1H, q, J = 8.79 Hz), 3.20 (1H, q, J = 5.47 Hz), 3.58 (2H, m, J = 3.70 Hz), 4.09 (3H, s), 6.82 (1H, d, J = 2.16 Hz), 7.46 (1H, d, J = 2.12 Hz), 7.83 (1H, d, J = 8.84 Hz), 8.39 (1H, q, J = 3.76 Hz), 9.15 (1H, d, J = 2.36 Hz). MS m/z: 466 $(M + 1)^+$. |

-continued
| Examples | Formula | Arylamine reactant | $^1$H NMR and/or LC-MS: |
|---|---|---|---|
| 4 | 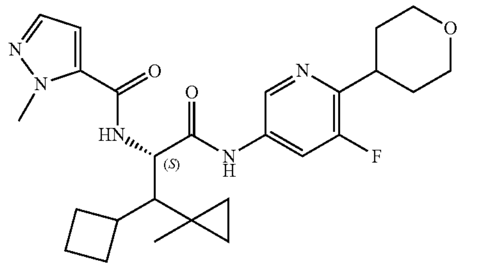 | 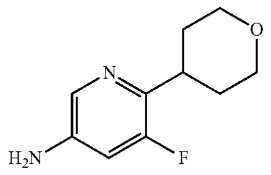 | $^1$H NMR (400 MHz, Methanol-d4) δ 8.51-8.44 (m, 1H), 8.24 (d, J = 9.1 Hz, 1H), 8.08-7.91 (m, 1H), 7.45 (d, J = 2.1 Hz, 1H), 6.80 (d, J = 2.2 Hz, 1H), 4.09 (s, 3H), 4.07-3.97 (m, 2H), 3.65-3.50 (m, 2H), 2.70-2.58 (m, 1H), 2.14-1.91 (m, 7H), 1.91-1.76 (m, 2H), 1.75-1.65 (m, 3H), 1.46-1.33 (m, 1H), 1.07 (s, 3H), 1.00 (d, J = 6.8 Hz, 1H), 0.54-0.44 (m, 1H), 0.42-0.33 (m, 1H), 0.30-0.24 (m, 1H). MS m/z: 484 $(M + 1)^+$. |
| 5 | 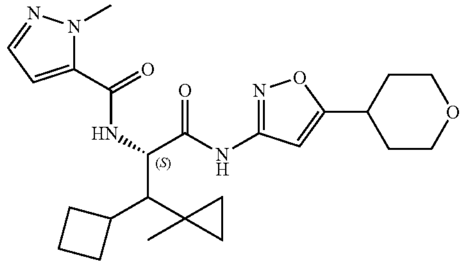 | 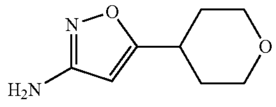 | MS m/z: 456 $(M + 1)^+$ |
| 6 | 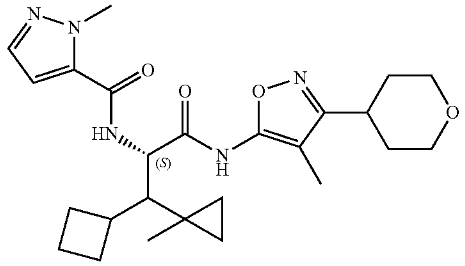 | 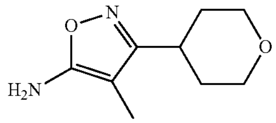 | MS m/z: 570 $(M + 1)^+$ |
| 7 | 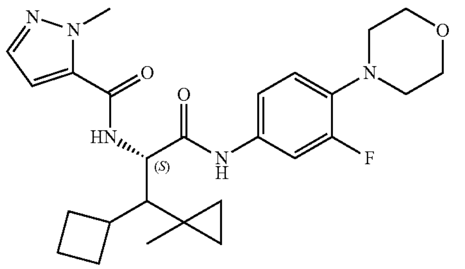 | 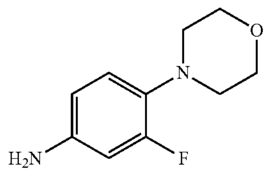 [SMILES: Nc1ccc(N2CCOCC2)c(F)c1] | MS m/z: 484 $(M + 1)^+$ |
| 8 | 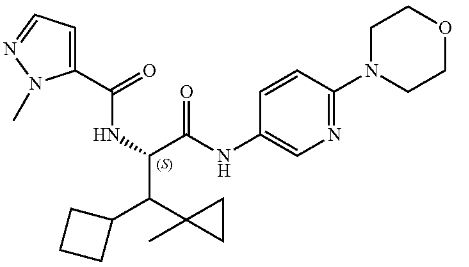 | 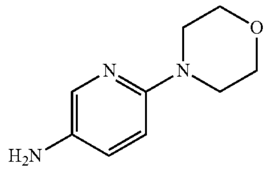 [SMILES: Nc1ccc(N2CCOCC2)nc1] | MS m/z: 467 $(M + 1)^+$ |

-continued

| Examples | Formula | Arylamine reactant | $^1$H NMR and/or LC-MS: |
|---|---|---|---|
| 9 | 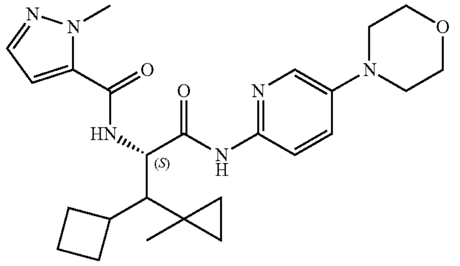 | 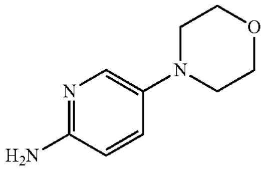 [SMILES: Nc1ccc(N2CCOCC2)cn1] | MS m/z: 467 (M + 1)$^+$ |
| 10 | 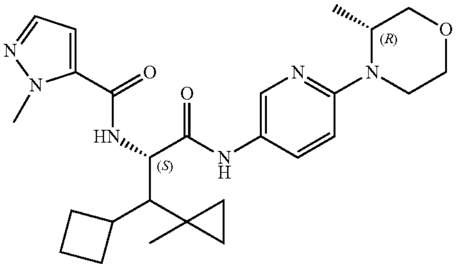 | 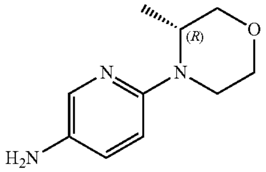 | $^1$H NMR (400 MHz, Methanol-$d_4$) δ 8.62 (d, J = 2.5 Hz, 1H), 8.10-8.01 (m, 1H), 7.46 (d, J = 2.1 Hz, 1H), 7.38 (d, J = 9.8 Hz, 1H), 6.81 (d, J = 2.2 Hz, 1H), 4.83 (dd, J = 9.6, 2.8 Hz, 2H), 4.17 (d, J = 6.9 Hz, 1H), 4.09 (s, 4H), 3.87-3.75 (m, 2H), 3.75-3.60 (m, 2H), 3.49 (td, J = 12.1, 3.9 Hz, 1H), 2.63 (p, J = 9.0 Hz, 1H), 2.06 (td, J = 10.1, 9.5, 6.9 Hz, 2H), 2.02-1.90 (m, 2H), 1.90-1.79 (m, 1H), 1.75-1.65 (m, 1H), 1.37 (d, J = 6.6 Hz, 3H), 1.07 (s, 3H), 0.50 (dt, J = 9.6, 4.9 Hz, 1H), 0.36 (dt, J = 9.4, 4.7 Hz, 1H), 0.29 (ddd, J = 9.5, 5.6, 4.0 Hz, 1H), 0.05 (ddd, J = 9.2, 5.6, 4.1 Hz, 1H). MS m/z: 481 (M + 1)$^+$. |
| 11 | 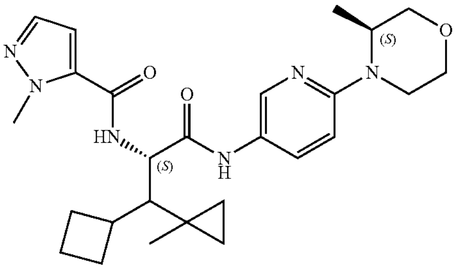 | 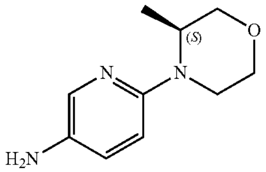 | $^1$H NMR (400 MHz, Methanol-$d_4$) δ 8.56 (d, J = 2.6 Hz, 1H), 8.24 (d, J = 9.1 Hz, 1H), 7.99 (dd, J = 9.6, 2.6 Hz, 1H), 7.46 (d, J = 2.1 Hz, 1H), 7.26 (d, J = 9.7 Hz, 1H), 6.81 (d, J = 2.1 Hz, 1H), 4.25-4.12 (m, 2H), 4.09 (s, 3H), 4.05 (dd, J = 11.5, 3.9 Hz, 1H), 3.87-3.79 (m, 3H), 3.82-3.71 (m, 2H), 3.76-3.67 (m, 2H), 3.70-3.59 (m, 2H), 3.51-3.36 (m, 1H), 2.72-2.56 (m, 2H), 2.14-2.01 (m, 2H), 2.01-1.90 (m, 2H), 1.89-1.78 (m, 1H), 1.75-1.66 (m, 1H), 1.38 (t, J = 10.1 Hz, 1H), 1.33 (d, J = 6.7 Hz, 3H), 1.07 (s, 3H), 0.55-0.45 (m, 1H), 0.44-0.33 (m, 2H), 0.34-0.24 (m, 1H). 0.11-0.01 (m, 1H). MS m/z: 481 (M + 1)$^+$. |
| 12 | 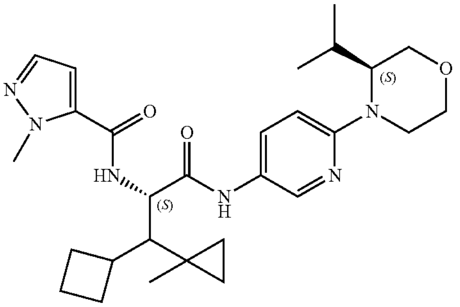 | 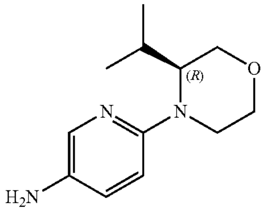 | $^1$H NMR (400 MHz, Methanol-d4) δ 8.21 (d, J = 2.6 Hz, 1H), 7.71 (dd, J = 9.2, 2.7 Hz, 1H), 7.45 (d, J = 2.2 Hz, 1H), 6.79 (d, J = 2.2 Hz, 1H), 6.73 (d, J = 9.2 Hz, 1H), 4.10 (s, 3H), 4.04 (d, J = 11.6 Hz, 1H), 3.99-3.93 (m, 1H), 3.91-3.84 (m, 2H), 3.57-3.51 (m, 2H), 2.73-2.55 (m, 1H), 2.55-2.37 (m, 1H), 2.06 (td, J = 10.0, 9.4, 6.7 Hz, 2H), 2.02-1.90 (m, 2H), 1.82 (q, J = 9.0 Hz, 1H), 1.75-1.63 (m, 1H), 1.43-1.26 (m, 2H), 1.08 (s, 3H), 1.04 (d, J = 6.6 Hz, 3H), 0.76 (d, J = 6.9 Hz, 3H), 0.53-0.39 (m, 2H), 0.32-0.23 (m, 1H), 0.15-0.06 (m, 1H). MS m/z: 509 (M + 1)$^+$. |

-continued

| Ex-am-ples | Formula | Arylamine reactant | $^1H$ NMR and/or LC-MS: |
|---|---|---|---|
| 13 | 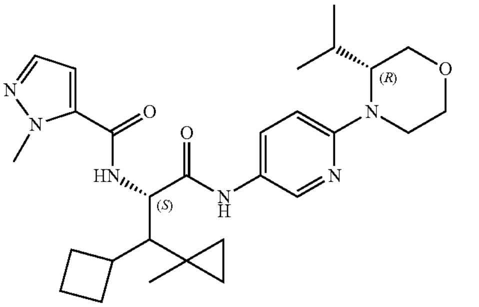 | 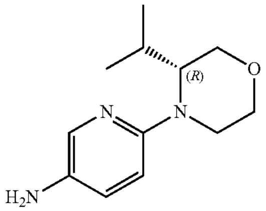 | $^1H$ NMR (400 MHz, Methanol-$d_4$) δ 8.56-8.46 (m, 1H), 7.96 (dd, J = 9.7, 2.6 Hz, 1H), 7.52-7.42 (m, 1H), 7.29 (d, J = 9.7 Hz, 1H), 6.81 (d, J = 2.1 Hz, 1H), 4.81 (s, 1H), 4.13 (d, J = 12.2 Hz, 1H), 4.09 (s, 3H), 3.97 (dd, J = 11.4, 3.6 Hz, 1H), 3.82 (d, J = 13.3 Hz, 1H), 3.75 (d, J = 10.2 Hz, 1H), 3.62 (td, J = 11.7, 2.9 Hz, 2H), 3.48 (td, J = 12.8, 3.6 Hz, 1H), 2.65 (p, J = 8.9 Hz, 1H), 2.59-2.47 (m, 1H), 2.06 (q, J = 9.7, 9.2 Hz, 3H), 1.95 (t, J = 8.2 Hz, 2H), 1.89-1.77 (m, 1H), 1.77-1.65 (m, 1H), 1.16-1.04 (m, 6H), 0.82 (d, J = 6.9 Hz, 3H), 0.50 (dt, J = 9.6, 4.8 Hz, 1H), 0.37 (dt, J = 9.5, 4.8 Hz, 1H), 0.29 (ddd, J = 9.5, 5.5, 4.0 Hz, 1H), 0.06 (ddd, J = 9.4, 5.6, 4.2 Hz, 1H). MS m/z: 509 $(M + 1)^+$. |
| 14 | 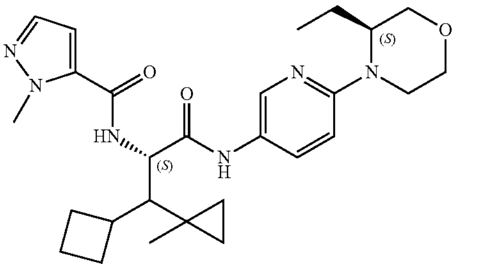 | 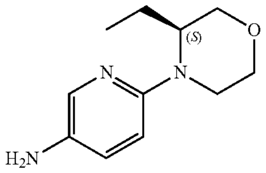 | $^1H$ NMR (400 MHz, Methanol-d4) δ 8.27 (dd, J = 2.7, 0.6 Hz, 1H), 7.77 (dd, J = 9.1, 2.7 Hz, 1H), 7.45 (d, J = 2.1 Hz, 1H), 6.79 (d, J = 2.1 Hz, 1H), 6.74 (d, J = 9.1 Hz, 1H), 4.83 (s, 1H), 4.10 (s, 3H), 4.05-3.97 (m, 1H), 3.94 (dd, J = 11.3, 3.8 Hz, 2H), 3.80 (dd, J = 13.2, 3.1 Hz, 1H), 3.68-3.52 (m, 2H), 3.23-3.11 (m, 1H), 2.72-2.57 (m, 1H), 2.13-2.02 (m, 2H), 2.00-1.90 (m, 2H), 1.89-1.79 (m, 2H), 1.75-1.65 (m, 1H), 1.63-1.50 (m, 1H), 1.36 (t, J = 10.1 Hz, 1H), 1.08 (s, 3H), 0.90 (t, J = 7.5 Hz, 3H), 0.55-0.40 (m, 2H), 0.32-0.23 (m, 1H), 0.15-0.07. MS m/z: 495 $(M + 1)^+$. |
| 15 | 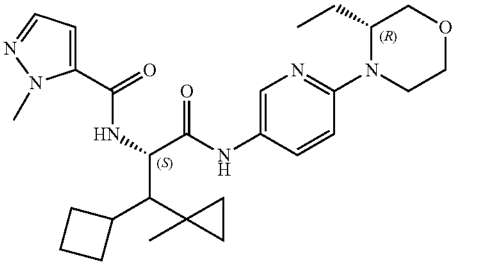 | 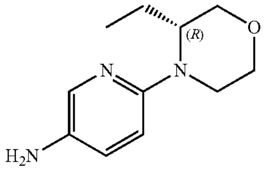 | MS m/z: 495 $(M + 1)^+$. |
| 16 | 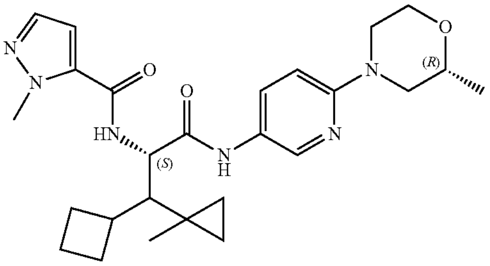 | 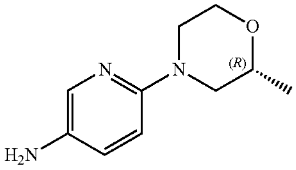 | $^1H$ NMR (400 MHz, Methanol-d4) δ 8.33-8.27 (m, 1H), 7.84-7.77 (m, 1H), 7.45 (d, J = 2.1 Hz, 1H), 6.86-6.75 (m, 2H), 4.09 (s, 3H), 4.06-3.88 (m, 4H), 3.74-3.61 (m, 2H), 2.91-2.81 (m, 1H), 2.68-2.58 (m, 1H), 2.58-2.46 (m, 1H), 2.11-2.01 (m, 3H), 2.00-1.89 (m, 2H), 1.87-1.76 (m, 1H), 1.69 (s, 1H), 1.40-1.31 (m, 1H), 1.22 (d, J = 6.2 Hz, 4H), 1.08 (s, 3H), 0.54-0.36 (m, 3H), 0.34-0.20 (m, 1H), 0.15-0.03 (m, 2H). MS m/z: 481 $(M + 1)^+$. |

-continued

| Examples | Formula | Arylamine reactant | $^1$H NMR and/or LC-MS: |
|---|---|---|---|
| 17 | 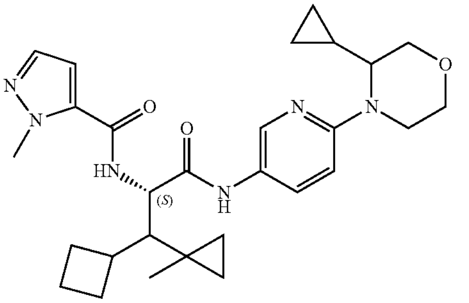 | 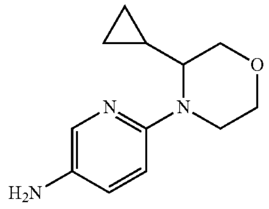 | $^1$H NMR (400 MHz, Methanol-$d_4$) δ 8.58 (d, J = 2.4 Hz, 1H), 8.02 (dd, J = 9.8, 2.5 Hz, 1H), 7.46 (d, J = 2.1 Hz, 1H), 7.39 (d, J = 9.8 Hz, 1H), 6.82 (d, J = 2.1 Hz, 1H), 4.82 (d, J = 2.6 Hz, 1H), 4.09 (s, 3H), 4.07-3.99 (m, 2H), 3.78 (dd, J = 11.6, 2.9 Hz, 1H), 3.75-3.61 (m, 3H), 3.56 (dd, J = 9.7, 2.7 Hz, 1H), 2.64 (q, J = 8.6 Hz, 1H), 2.06 (td, J = 10.0, 9.5, 7.1 Hz, 2H), 1.95 (t, J = 8.3 Hz, 2H), 1.90-1.76 (m, 1H), 1.67 (dtd, J = 26.2, 9.2, 8.5, 5.3 Hz, 2H), 1.07 (s, 3H), 0.62 (ddd, J = 8.8, 6.9, 4.2 Hz, 1H), 0.50 (dtt, J = 19.7, 9.6, 4.6 Hz, 3H), 0.41-0.24 (m, 3H), 0.06 (dq, J = 9.2, 4.4 Hz, 1H). MS m/z: 507 $(M + 1)^+$. |
| 18 | 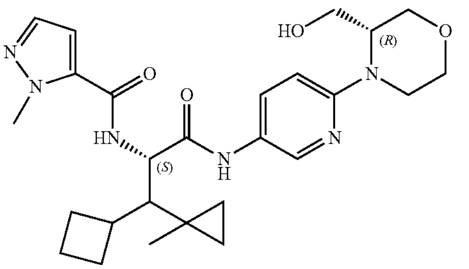 | 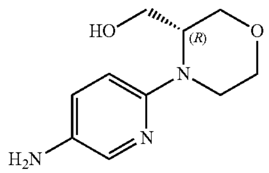 | $^1$H NMR (400 MHz, Methanol-d4) δ 8.44 (d, J = 2.6 Hz, 1H), 7.94-7.85 (m, 1H), 7.50-7.42 (m, 1H), 7.12 (d, J = 9.5 Hz, 1H), 6.81 (d, J = 2.2 Hz, 1H), 4.24-4.12 (m, 1H), 4.06 (s, 1H), 4.01 (dd, J = 11.6, 3.8 Hz, 1H), 3.90-3.72 (m, 4H), 3.71 (dd, J = 11.9, 3.2 Hz, 1H), 3.69-3.57 (m, 2H), 3.40-3.30 (m, 2H), 2.72-2.55 (m, 1H), 2.16-2.01 (m, 2H), 2.01-1.90 (m, 3H), 1.91-1.76 (m, 1H), 1.76-1.56 (m, 0H), 1.37 (t, J = 10.1 Hz, 1H), 1.29 (s, 1H), 1.07 (s, 3H), 0.57-0.44 (m, 1H), 0.45-0.34 (m, 1H), 0.34-0.21 (m, 1H), 0.13-0.02 (m, 1H). MS m/z: 497 $(M + 1)^+$. |
| 19 | 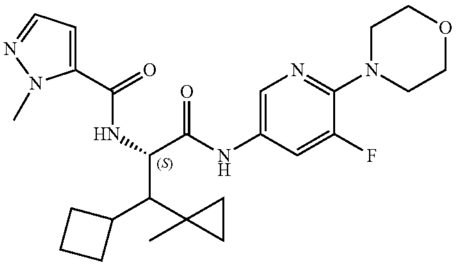 | 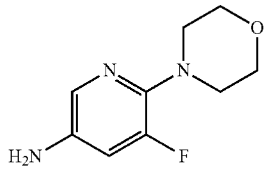 | $^1$H NMR (400 MHz, Methanol-$d_4$) δ 8.21-8.14 (m, 1H), 7.86 (dd, J = 14.4, 2.2 Hz, 1H), 7.50-7.43 (m, 1H), 6.80 (d, J = 2.2 Hz, 1H), 4.09 (s, 3H), 3.83-3.77 (m, 4H), 3.40-3.35 (m, 4H), 2.63 (hept, J = 10.1, 9.5 Hz, 1H), 2.13-1.98 (m, 3H), 1.94 (dd, J = 10.0, 6.7 Hz, 2H), 1.84 (p, J = 9.6 Hz, 1H), 1.75-1.65 (m, 1H), 1.07 (s, 3H), 0.49 (dt, J = 9.6, 4.8 Hz, 1H), 3.9 (dt, J = 9.5, 4.8 Hz, 1H), 0.31-0.24 (m, 1H), 0.06 (ddd, J = 9.4, 5.5, 4.2 Hz, 1H). MS m/: 485 $(M + 1)^+$. |
| 20 | 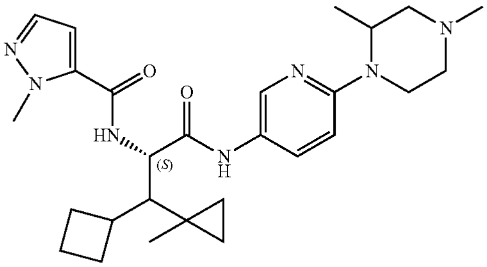 | 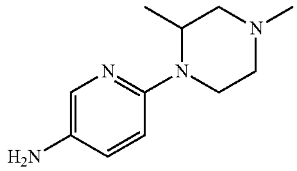 | $^1$H NMR (400 MHz, Methanol-$d_4$) δ 8.34 (d, J = 2.7 Hz, 1H), 7.83 (dd, J = 9.1, 2.7 Hz, 1H), 7.46 (d, J = 2.2 Hz, 1H), 6.84 (d, J = 9.2 Hz, 1H), 6.80 (d, J = 2.1 Hz, 1H), 4.82 (s, 1H), 4.72-4.55 (m, 2H), 4.10 (s, 3H), 3.25-3.16 (m, 2H), 3.09-2.99 (m, 1H), 2.73-2.57 (m, 3H), 2.13-1.89 (m, 4H), 1.89-1.77 (m, 1H), 1.75-1.65 (m, 0H), 1.43-1.17 (m, 16H), 1.08 (s, 3H), 0.95-0.81 (m, 3H), 0.56-0.37 (m, 2H), 0.33-0.23 (m, 1H), 0.11-0.07 (m, 1H). MS m/z: 494 $(M + 1)^+$. |

-continued

| Examples | Formula | Arylamine reactant | $^1$H NMR and/or LC-MS: |
|---|---|---|---|
| 21 | 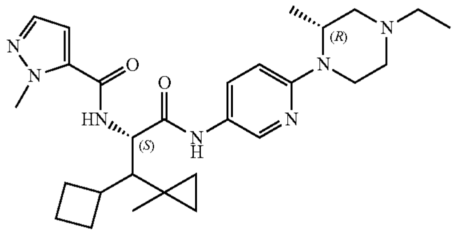 | 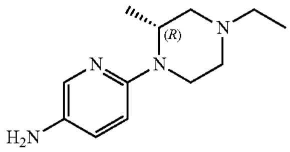 | $^1$H NMR (400 MHz, Methanol-d4) δ 8.50-8.37 (m, 1H), 7.90 (d, J = 8.8 Hz, 1H), 7.52-7.39 (m, 1H), 6.96 (d, J = 9.2 Hz, 1H), 6.79 (d, J = 2.1 Hz, 1H), 4.43-4.25 (m, 1H), 4.09 (s, 3H), 3.73-3.48 (m, 2H), 3.29-3.21 (m, 3H), 3.10 (d, J = 12.6 Hz, 1H), 2.76-2.53 (m, 1H), 2.13-2.02 (m, 2H), 2.02-1.90 (m, 2H), 1.90-1.77 (m, 1H), 1.77-1.59 (m, 1H), 1.48-1.36 (m, 4H), 1.36-1.23 (m, 4H), 1.08 (s, 3H), 0.55-0.46 (m, 1H), 0.46-0.35 (m, 1H), 0.35-0.22 (m, 1H), 0.13-0.04 (m, 1H). MS m/z: 508 $(M + 1)^+$. |
| 22 | 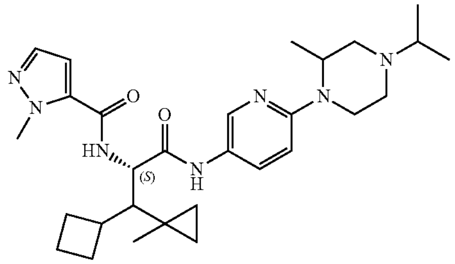 | 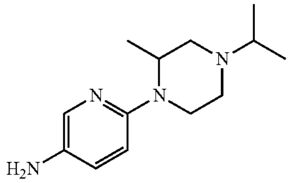 | $^1$H NMR (400 MHz, Methanol-$d_4$) δ 8.29 (d, J = 2.6 Hz, 1H), 7.79 (dd, J = 9.2, 2.7 Hz, 1H), 7.48 (d, J = 2.1 Hz, 1H), 6.82 (d, J = 2.1 Hz, 1H), 6.78 (d, J = 9.1 Hz, 1H), 4.85 (s, 1H), 4.48-4.36 (m, 0H), 4.16-4.08 (m, 6H), 3.95-3.85 (m, 1H), 3.20-3.08 (m, 1H), 3.03-2.92 (m, 1H), 2.91-2.82 (m, 1H), 2.82-2.58 (m, 2H), 2.56-2.48 (m, 1H), 2.44-2.33 (m, 1H), 2.15-1.91 (m, 4H), 1.91-1.77 (m, 1H), 1.77-1.67 (m, 1H), 1.42-1.27 (m, 6H), 1.20 (d, J = 6.6 Hz, 3H), 1.17-1.06 (m, 9H), 0.96-0.87 (m, 1H), 0.55-0.41 (m, 2H), 0.34-0.26 (m, 1H), 0.19-0.09 (m, 1H). MS m/z: 522 $(M + 1)^+$. |
| 23 | 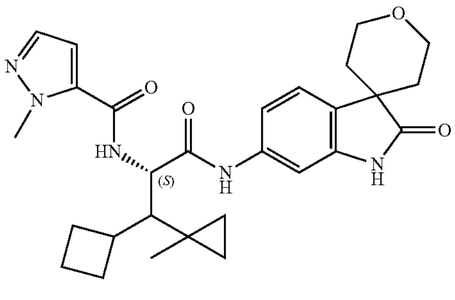 | 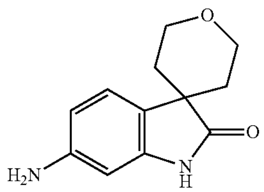 [SMILES: Nc1ccc2c(c1)NC(=O)C21CCOCC1] | $^1$H NMR (400 MHz, Methanol-d4) δ 7.49-7.39 (m, 3H), 7.13 (dd, J = 8.1, 2.0 Hz, 1H), 6.81 (d, J = 2.2 Hz, 1H), 4.83 (d, J = 2.5 Hz, 1H), 4.21-4.12 (m, 2H), 4.10 (s, 3H), 3.97-3.87 (m, 2H), 2.65 (h, J = 8.9 Hz, 1H), 2.14-2.02 (m, 2H), 1.97 (q, J = 9.0, 8.3 Hz, 2H), 1.92-1.83 (m, 3H), 1.82-1.66 (m, 4H), 1.08 (s, 3H), 0.52-0.38 (m, 2H), 0.31-0.22 (m, 1H), 0.11-0.03 (m, 1H). MS m/z: 506 $(M + 1)^+$. |

Example 24 Preparation of Compound 24

Compound 24 were synthesized through the general route A, in combination with operation steps described in Example 1. Briefly, in step (1), the 4-(4-morpholinyl) aniline used in Example 1 was replaced with arylamine shown in the following table to undergo condensation with the intermediate 1; in step 2, the benzyloxycarbonyl (Cbz) protecting group was removed by Pd/C-catalyzed hydrogenation; and in step (3), the hydrogenated product underwent condensation with 1-methyl-5-pyrazolecarboxylic acid, and tert-butoxycarbonyl (Boc) protecting group was removed by trifluoroacetic acid.

| Example | Formula | Arylamine, reactant, | $^1$HNMR and/or LCMS: |
|---|---|---|---|
| 24 | 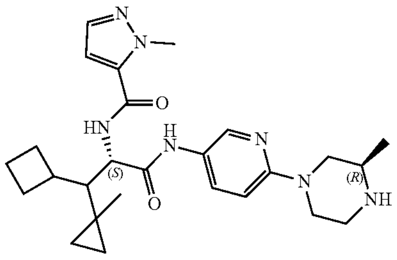 | 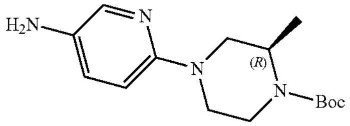 | MS m/z: 480 $(M + 1)^+$ |

Examples 25 to 27 Preparation of Compounds 25-27

Compounds 25 to 27 were synthesized through the general route A, in combination with operation steps described in Example 1. Briefly, in step (1), the starting material intermediate 1 in Example 1 was replaced with other amino acids shown in the following table, and 4-(4-morpholinyl) aniline was replaced with other amines, so as to realize the condensation of the amino acid and the amine; in step 2, the benzyloxycarbonyl (Cbz) protecting group was removed by Pd/C-catalyzed hydrogenation; and in step 3, the hydrogenated product underwent condensation with 1-methyl-5-pyrazolecarboxylic acid.

| Examples | Formula | Amino acids | Amine, reactant, | $^1$HNMR and/or LCMS: |
|---|---|---|---|---|
| 25 | 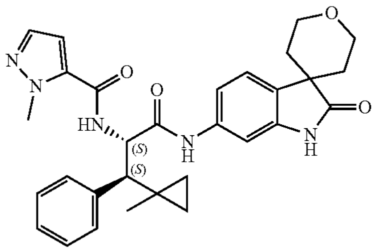 | 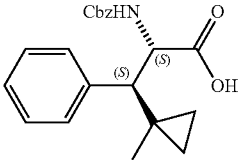 | 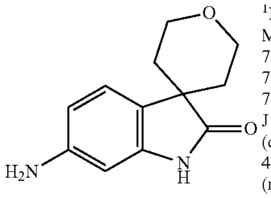 | $^1$H NMR (400 MHz, Methanol-d4) δ 7.52-7.42 (m, 2H), 7.34-7.25 (m, 6H), 7.25-7.19 (m, 2H), 6.26 (d, J = 2.1 Hz, 1H), 5.35 (d, J = 11.9 Hz, 1H), 4.58 (s, 2H), 4.22-4.11 (m, 3H), 3.98-3.88 (m, 3H), 3.85 (s, 3H), 2.62 (d, J = 11.9 Hz, 1H), 1.90 (d, J =15.1 Hz, 3H), 1.84-1.74 (m, 2H), 1.34-1.24 (m, 4H), 1.12 (s, 4H), 0.89 (d, J = 6.9 Hz, 1H), 0.79-0.68 (m, 1H), 0.59-0.50 (m, 1H), 0.39-0.30 (m, 1H). MS m/z: 528 $(M + 1)^+$ |

-continued
| Ex-am-ples | Formula | Amino acids | Amine, reactant, | $^1$HNMR and/or LCMS: |
|---|---|---|---|---|
| 26 | 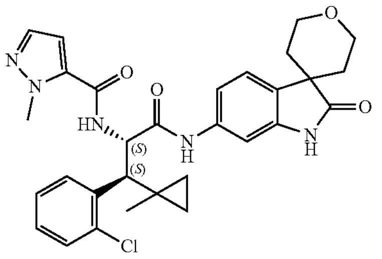 | 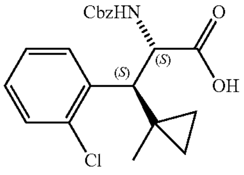 | 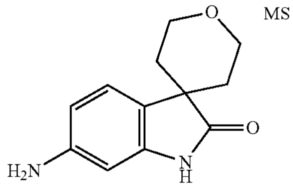 | MS m/z: 563 $(M + 1)^+$ |
| 27 | 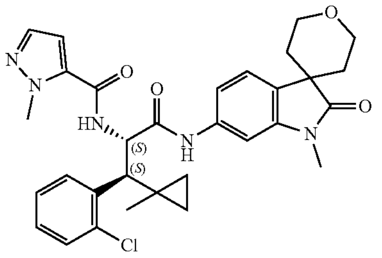 | 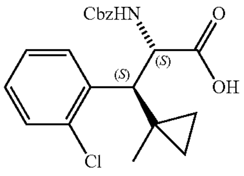 | 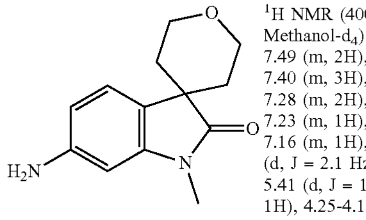 | $^1$H NMR (400 MHz, Methanol-$d_4$) $\delta$ 7.55-7.49 (m, 2H), 7.50-7.40 (m, 3H), 7.32-7.28 (m, 2H), 7.30-7.23 (m, 1H), 7.25-7.16 (m, 1H), 6.30 (d, J = 2.1 Hz, 1H), 5.41 (d, J = 11.6 Hz, 1H), 4.25-4.13 (m, 3H), 3.99-3.88 (m, 3H), 3.84 (s, 3H), 3.83 (d, J = 1.8 Hz, 1H), 3.54 (d, J = 11.7 Hz, 1H), 3.22 (s, 3H), 1.92-1.75 (m, 4H), 1.39-1.26 (m, 3H), 1.20 (s, 3H), 0.93-0.88 (m, 1H), 0.68-0.58 (m, 1H), 0.36-0.26 (m, 1H), 0.14-0.06 (m, 1H). MS m/z: 577 $(M + 1)^+$. |
Example 28 Preparation of Compound 28 (General Route B)
The general route B was shown as follows:
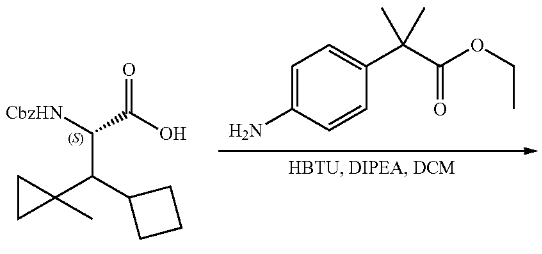
1
-continued
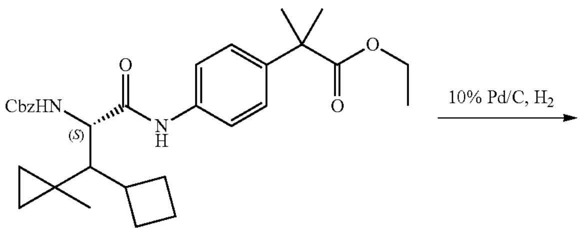
28-1

-continued

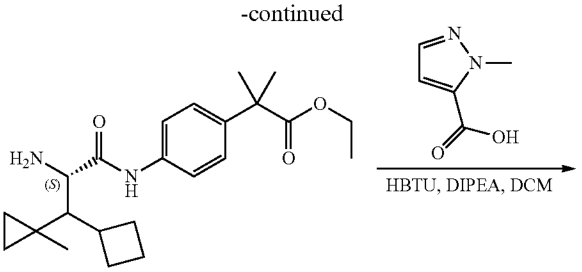

28-2

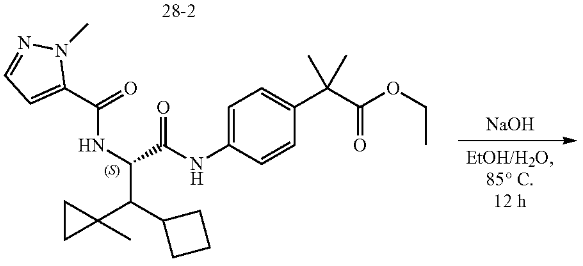

28-3

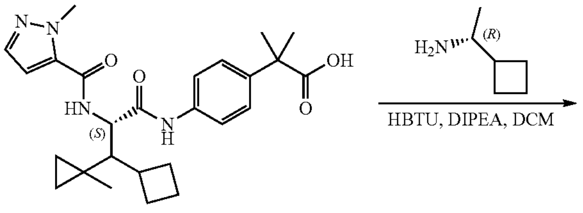

28-4

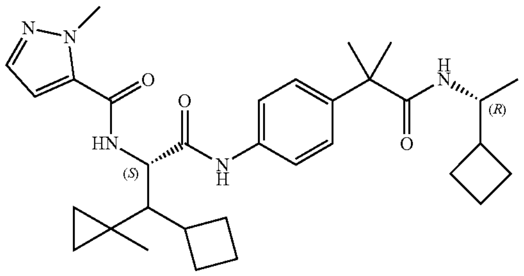

28

Step 1 Preparation of Intermediate 28-1

500 mg of the intermediate 1 (1.51 mmol), 686.75 mg of HBTU (1.81 mmol), 584.37 mg of DIPEA (4.53 mmol) were added to a 100 mL single-necked flask, and dissolved in 15 mL of $CH_2Cl_2$. The reaction mixture was reacted under stirring at room temperature for 10 min, and added with 374.67 mg of ethyl 2-(4-aminophenyl)-2-methylpropanoate (1.81 mmol). Then, the reaction mixture was reacted under stirring at room temperature for 3 h, and added with 30 ml of water, and extract with $CH_2Cl_2$ (30 mL*2). The organic phases were combined, washed with saturated NaCl solution ((30 mL*2)), dried with anhydrous sodium sulfate, filtered, and concentrated under reduced pressure. The residue was separated and purified by silica gel column chromatography to obtain 588.90 mg of the intermediate 28-1 (1.13 mmol) with a yield of 75%. MS m/z: 521.0 $(M+1)^+$.

Step 2 Preparation of Intermediate 28-2

To a 100 mL single-necked flask was added 588.90 mg of the intermediate 28-1 (1.13 mmol) and 20 mL of EtOH, and added 177 mg of 10% Pd/C (w/w 50%) at room temperature under stirring and nitrogen protection. The reaction mixture was reacted under stirring at room temperature in the presence of hydrogen for 2 h, filtered, and concentrated under reduced pressure to give 397 mg of the intermediate 28-2 (1.03 mmol) with a yield of 91%. MS m/z: 387.0 $(M+1)^+$.

Step 3 Preparation of Intermediate 28-3

129.78 mg of 1-methylpyrazole-5-carboxylic acid (1.03 mmol), 468.44 mg of HBTU (1.24 mmol), 98.61 mg of DIPEA (33.09 mmol) were added to a 100 mL single-necked flask, and dissolved in 10 mL of $CH_2Cl_2$. The reaction mixture was reacted under stirring at room temperature for 10 min, and added with 397 mg of the intermediate 28-2 (1.03 mmol) at room temperature. Then, the reaction mixture was reacted under stirring at room temperature for 1 h, and added with 30 mL of water, and extract with $CH_2Cl_2$ (30 mL*2). The organic phases were combined, washed with saturated NaCl solution (30 mL*2), dried with anhydrous sodium sulfate, filtered, and concentrated under reduced pressure. The residue was separated and purified by silica gel column chromatography to give 418.08 mg of the intermediate 28-3 (0.84 mmol) with a yield of 82%. MS m/z: 495.0 $(M+1)^+$.

Step 4 Preparation of Intermediate 28-4

418.08 mg of the intermediate 28-3 (0.84 mmol) was added to a 50 mL single-necked flask, and dissolved in 4 mL of EtOH and 0.4 mL of $H_2O$, to which 168.00 mg of NaOH (4.20 mmol) was added under stirring at room temperature. After that, the reaction mixture was heated at 85° C. and stirred overnight for reaction. Then, the reaction mixture was diluted with 30 mL of $H_2O$, adjusted to pH 4 with 6N HCl, and subjected to extraction with ethyl acetate (30 mL*2). The organic phases were combined, washed with saturated NaCl solution (30 mL*2), dried with anhydrous sodium sulfate, filtered, and concentrated under reduced pressure to give 352.30 mg of the intermediate 28-4 (0.76 mmol) with a yield of 90%. MS m/z: 467.0 $(M+1)^+$.

Step 5 Preparation of Compound 28

30.00 mg of the intermediate 28-4 (0.055 mmol), 24.94 mg of HBTU (0.066 mmol), 21.29 mg of DIPEA (0.17 mmol) were added to a 25 mL single-necked flask, and dissolved in 2 mL of $CH_2Cl_2$. The reaction mixture was reacted under stirring at room temperature for 10 min, and added with 6.53 mg of (R)-1-cyclobutylethanamine (0.066 mmol) at room temperature. Then, the reaction mixture was reacted under stirring at room temperature for 1 h, and added with 5 mL of water, and subjected to extraction with $CH_2Cl_2$ (5 mL*2). The organic phases were combined, washed with saturated NaCl solution (5 mL*2), dried with anhydrous sodium sulfate, filtered, and concentrated under reduced pressure. The residue was purified by MPLC (ACN/H2O, 0.05% FA) to give 18.35 mg of the compound 28 (0.034 mmol) with a yield of 61%. MS m/z: 548.0 $(M+1)^+$.

Examples 29-31 Preparation of Compounds 29-31

Compounds 29-31 were synthesized through the general route B in combination with operation steps described in Example 28. Briefly, the intermediate 28-4 in step 4 underwent condensation with other amines demonstrated in the following table.

| Examples | Formula | Amine, reactant | $^1$HNMR and/or LCMS |
|---|---|---|---|
| 29 | 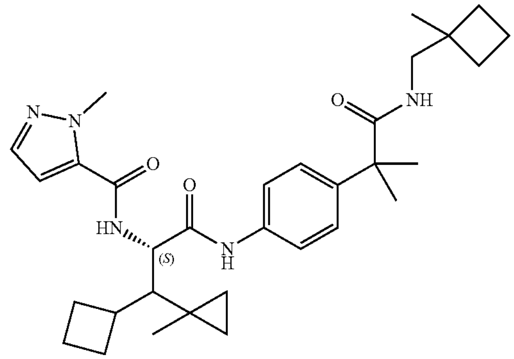 | 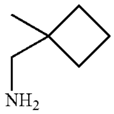 | MS m/z: 548 (M + 1)$^+$ |
| 30 | 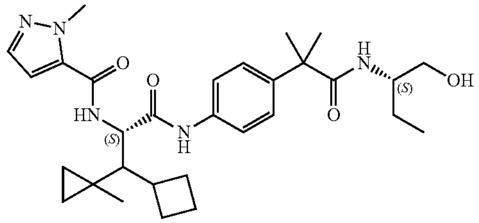 | 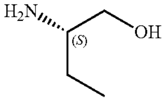 | MS m/z: 538 (M + 1)$^+$ |
| 31 | 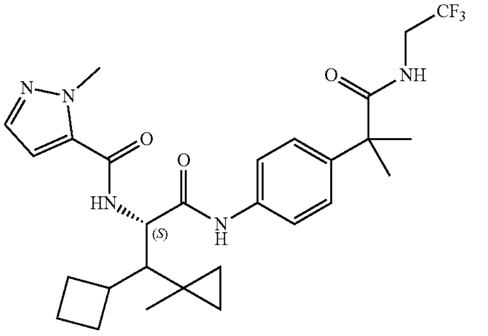 | 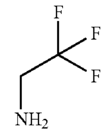 | MS m/z: 548 (M + 1)$^+$ |
Examples 32-35 Preparation of Compounds 32-35
The compound 32 was prepared through the following route:
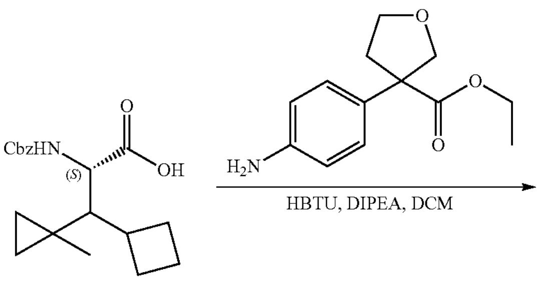
1
-continued
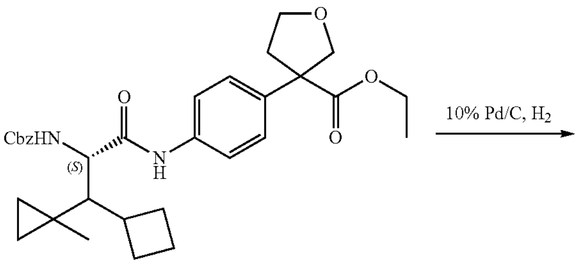
32-1
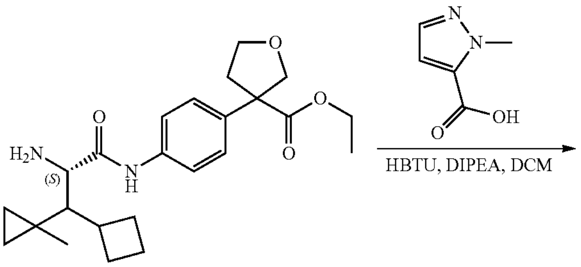
32-2

-continued

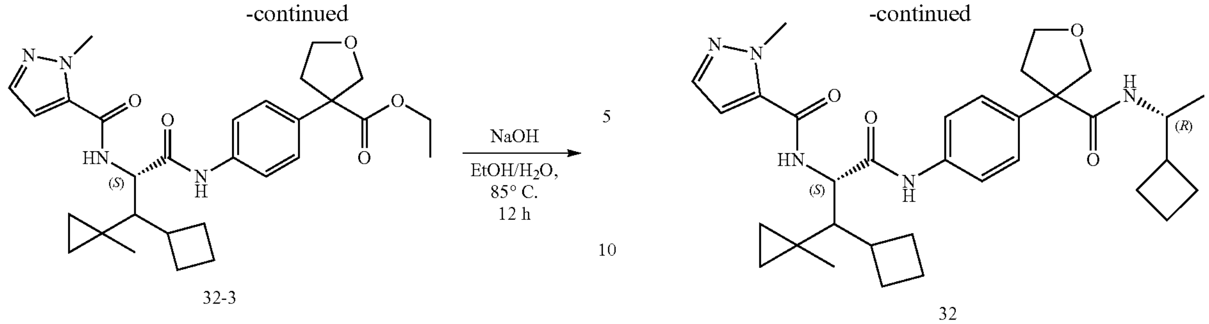

32-3

32

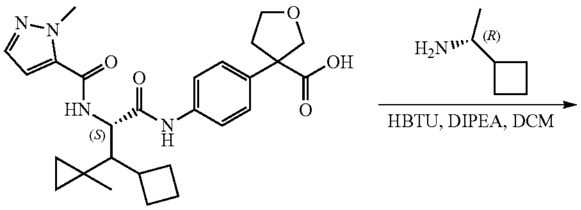

32-4

Compound 32 was synthesized from through operation steps described in Example 28. Briefly, the intermediate 1 and ethyl 3-(4-aminophenyl)tetrahydrofuran-3-carboxylate were synthesized to obtain compound 32, MS m/z: 576 $(M+1)^+$. Similarly, compound 33-35 were synthesized through operation steps described in Example 28. Briefly, compound 33-35 were synthesized from compound 33-35 were synthesized from intermediate 28-4 in step 4 underwent condensation with other amines demonstrated in the following table.

| Examples | Formula | Amine, reactant | $^1$HNMR and/or LCMS |
|---|---|---|---|
| 33 | 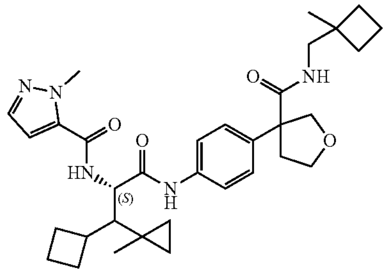 | 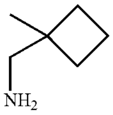 | MS m/z: 576 $(M + 1)^+$ |
| 34 | 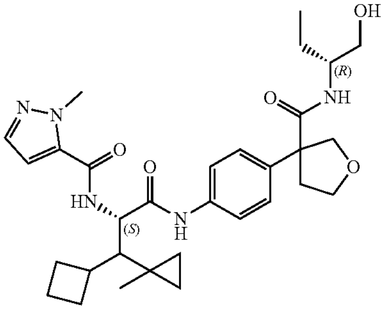 | 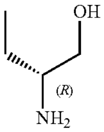 | MS m/z: 566 $(M + 1)^+$ |
| 35 | 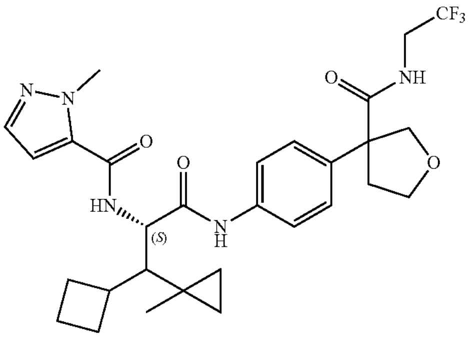 | 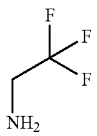 | MS m/z: 576 $(M + 1)^+$ |

Example 36 Preparation of Compound 36

The compound 36 was prepared through the following route:

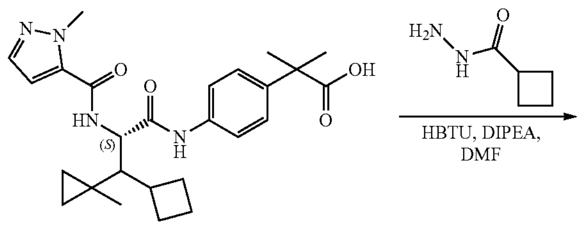

28-1

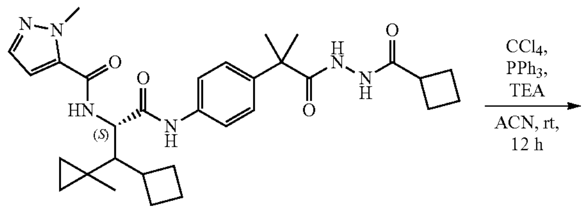

36-1

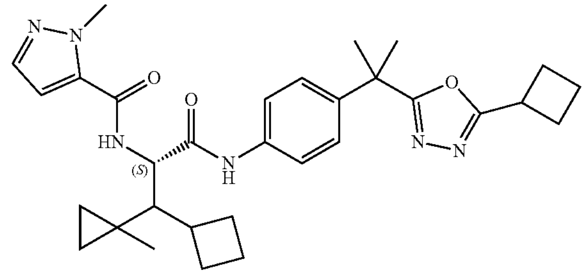

36

Compound 36 was synthesized through the general route B in combination with operation steps described in Example 28. Briefly, the intermediate 28-4 in step 4 underwent condensation with cyclobutanecarbohydrazide followed by ring closing reaction.

$^1$H NMR (400 MHz, Methanol-d4) δ 7.61-7.54 (m, 2H), 7.41 (d, J=2.2 Hz, 1H), 7.28-7.21 (m, 2H), 6.76 (d, J=2.2 Hz, 1H), 4.06 (s, 3H), 3.77-3.63 (m, 1H), 2.73-2.56 (m, 1H), 2.45-2.25 (m, 4H), 2.18-1.80 (m, 7H), 1.78 (s, 6H), 1.75-1.64 (m, 1H), 1.42-1.31 (m, 1H), 1.07 (s, 3H), 0.52-0.37 (m, 2H), 0.30-0.21 (m, 1H), 0.12-0.03 (m, 1H). MS m/z: 545 $(M+1)^+$.

Example 37 Preparation of Compound 37

The compound 37 is prepared through the following route:

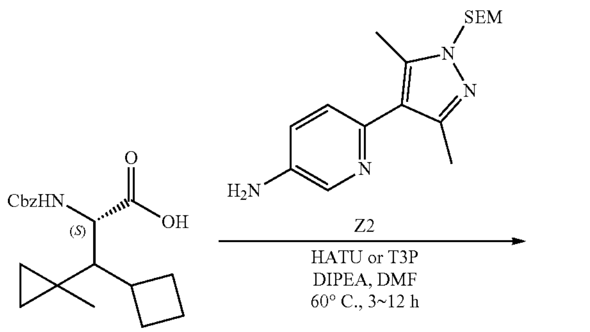

1

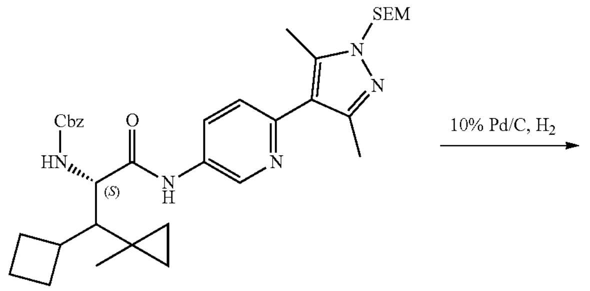

37-1

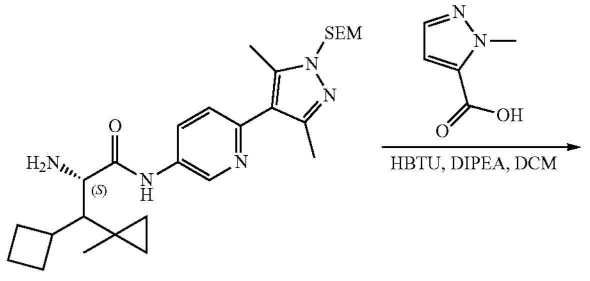

37-2

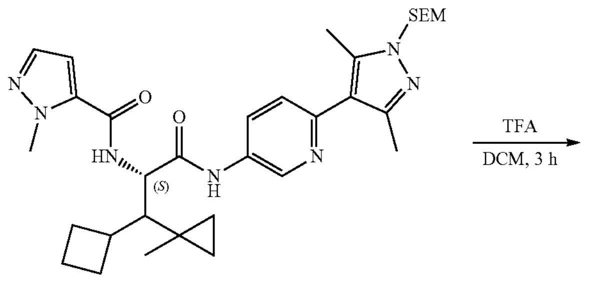

37-3

-continued

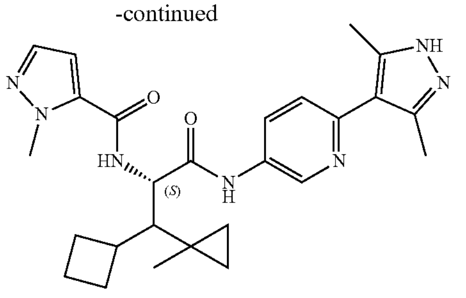

37

Compound 37 was synthesized through the general route A in combination with operation steps described in Example 1. Briefly, in step 1, the intermediate Z2 underwent condensation with intermediate 1 to obtain intermediate 37-1; in step 2, the benzyloxycarbonyl (Cbz) protecting group was removed by Pd/C-catalyzed hydrogenation to obtain intermediate 37-2; and in step 3, the intermediate 37-2 underwent condensation with 1-methyl-5-pyrazolecarboxylic acid to obtain intermediate 37-3, and a [2-(Trimethylsilyl) ethoxy] methyl acetal (SEM) protecting group is removed by trifluoroacetic acid.

$^1$H NMR (400 MHz, MeOD) δ 9.22 (d, J=2.3 Hz, 1H), 8.44 (dd, J=8.8, 2.5 Hz, 1H), 7.83 (dd, J=8.6, 3.7 Hz, 1H), 7.47 (d, J=2.1 Hz, 1H), 6.83 (d, J=2.1 Hz, 1H), 4.91 (s, 1H), 4.10 (s, 3H), 2.68 (dd, J=17.5, 8.3 Hz, 1H), 2.38 (s, 6H), 2.08 (dd, J=17.1, 9.5 Hz, 2H), 2.04-1.92 (m, 2H), 1.85 (dd, J=17.8, 8.5 Hz, 1H), 1.72 (d, J=7.0 Hz, 1H), 1.44 (t, J=10.0 Hz, 1H), 1.10 (s, 3H), 0.53 (dt, J=9.3, 4.9 Hz, 1H), 0.46-0.37 (m, 1H), 0.36-0.26 (m, 1H), 0.17-0.06 (m, 1H). MS m/z: 476 $(M+1)^+$.

Examples 38-52 Preparation of Compounds 38-52

Similarly, compounds 38-52 were synthesized through the route illustrated in Example 37. Briefly, (S)-2-((carbobenzoxy) amino)-3,3-dicyclopropylpropanoic acid (intermediate 2) underwent condensation with amine Z2 or amine Z3; in step 2, the benzyloxycarbonyl (Cbz) protecting group was removed by Pd/C-catalyzed hydrogenation; and in step 3, the hydrogenated product underwent condensation with other carboxylic acids shown in the following table, and the SEM protecting group was removed.

| Examples | Formula | Carboxylic acid | Amine, reactant | $^1$HNMR and/or LCMS |
|---|---|---|---|---|
| 38 | 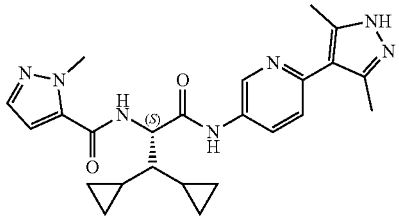 | 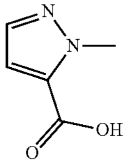 | 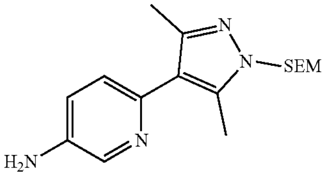 Z2 | $^1$H NMR (400 MHz, Methanol-$d_4$) δ 9.22 (d, J = 2.4 Hz, 1H), 8.42 (dd, J = 8.8, 2.5 Hz, 1H), 7.83 (d, J = 8.7 Hz, 1H), 7.50 (d, J = 2.2 Hz, 1H), 6.90 (d, J = 2.1 Hz, 1H), 4.10 (s, 3H), 2.38 (s, 6H), 1.37-1.25 (m, 3H), 0.98-0.88 (m, 1H), 0.92-0.79 (m, 4H), 0.63-0.55 (m, 1H), 0.57-0.41 (m, 2H), 0.44-0.26 (m, 4H), 0.26-0.18 (m, 1H). MS m/z: 448 $(M + 1)^+$. |
| 39 | 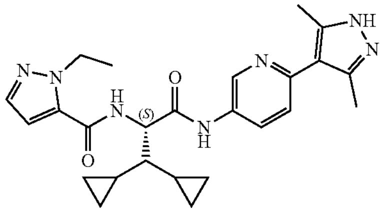 | 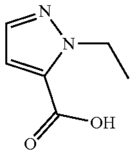 | 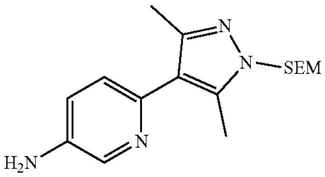 Z2 | $^1$H NMR (400 MHz, Methanol-$d_4$) δ 9.24-9.17 (m, 1H), 8.41 (dd, J = 8.8, 2.5 Hz, 1H), 7.82 (dd, J = 8.8, 0.7 Hz, 1H), 7.51 (d, J = 2.1 Hz, 1H), 6.88 (d, J = 2.1 Hz, 1H), 4.94-4.88 (m, 1H), 4.54 (q, J = 7.1 Hz, 2H), 2.38 (s, 6H), 1.38 (t, J = 7.2 Hz, 3H), 0.99-0.90 (m, 1H), 0.89-0.81 (m, 2H), 0.65-0.56 (m, 1H), 0.55-0.44 (m, 2H), 0.44-0.28 (m, 4H), 0.28-0.19 (m, 1H). MS m/z: 462$(M + 1)^+$. |

-continued

| Examples | Formula | Carboxylic acid | Amine, reactant | $^1$HNMR and/or LCMS |
|---|---|---|---|---|
| 40 | 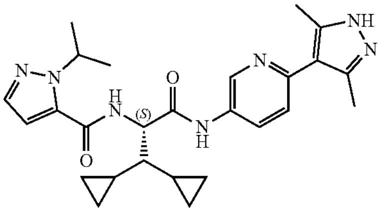 | 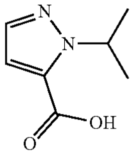 | 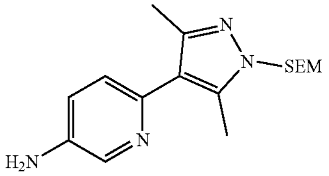<br>Z2 | $^1$H NMR (400 MHz, Methanol-$d_4$) δ 9.25 (d, J = 2.1 Hz, 1H), 8.43 (dd, J = 8.8, 2.5 Hz, 1H), 7.86 (d, J = 8.9 Hz, 1H), 7.53 (d, J =2.0 Hz, 1H), 6.80 (d, J = 2.1 Hz, 1H), 5.39 (p, J = 6.7 Hz, 1H), 4.89 (d, J = 7.4 Hz, 1H), 2.39 (s, 6H), 1.50-1.40 (m, 6H), 0.93 (dd, J = 10.3, 5.2 Hz, 1H), 0.89-0.79 (m, 2H), 0.58 (s, 1H), 0.50 (tt, J = 8.6, 4.2 Hz, 2H), 0.38 (dt, J = 8.9, 4.2 Hz, 2H), 0.32 (dt, J = 9.0, 5.2 Hz, 2H), 0.22 (dd, J = 9.4, 4.9 Hz, 1H). MS m/z: 476(M + 1)$^+$. |
| 41 | 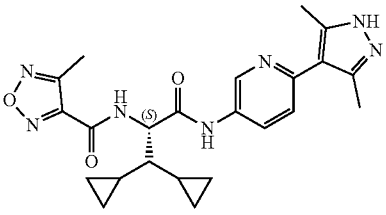 | 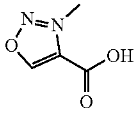 | 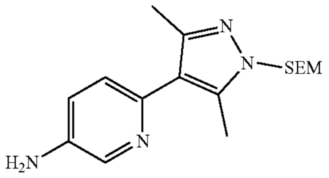<br>Z2 | $^1$H NMR (400 MHz, Methanol-$d_4$) δ 9.17 (d, J = 2.5 Hz, 1H), 8.39 (dd, J = 8.8, 2.5 Hz, 1H), 7.79 (d, J = 8.8 Hz, 1H), 4.97 (d, J = 6.2 Hz, 1H), 2.55 (s, 3H), 2.38 (s, 6H), 0.97-0.82 (m, 3H), 0.58 (td, J = 9.1, 4.1 Hz, 1H), 0.55-0.46 (m, 2H), 0.46-0.38 (m, 1H), 0.38-0.29 (m, 3H), 0.25 (dt, J = 9.5, 4.6 Hz, 1H). MS m/z: 450 (M + 1)$^+$. |
| 42 | 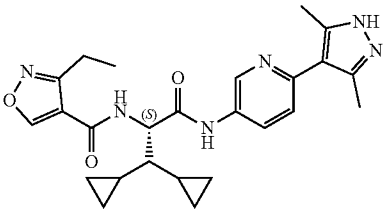 | 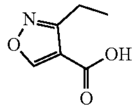 | 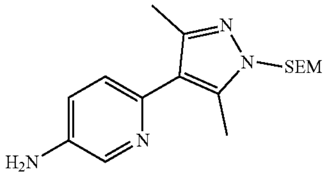<br>Z2 | $^1$H NMR (400 MHz, Methanol-$d_4$) δ 9.22 (d, J = 2.5 Hz, 1H), 9.14 (s, 1H), 8.42 (dd, J = 8.8, 2.6 Hz, 1H), 7.84 (d, J = 8.8 Hz, 1H), 4.89 (d, J = 7.1 Hz, 1H), 2.92 (q, J = 7.5 Hz, 2H), 2.38 (s, 6H), 1.27 (t, J = 7.5 Hz, 3H), 0.96 (ddt, J = 10.1, 8.2, 4.2 Hz, 1H), 0.91-0.76 (m, 2H), 0.59 (tq, J = 9.0, 4.6 Hz, 1H), 0.55-0.43 (m, 2H), 0.43-0.36 (m, 1H), 0.32 (q, J = 5.0 Hz, 3H), 0.22 (dq, J = 9.2, 4.8 Hz, 1H). MS m/z: 463 (M + 1)$^+$. |
| 43 | 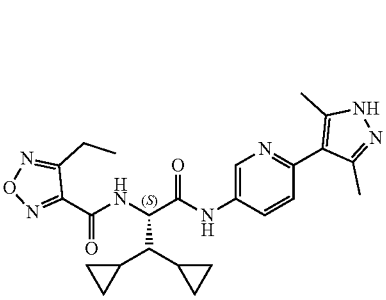 | 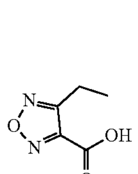 | 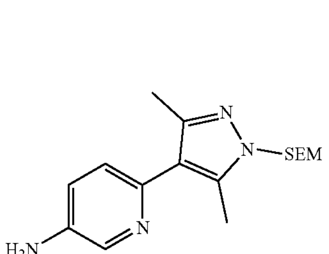<br>Z2 | $^1$H NMR (400 MHz, Methanol-$d_4$) δ 9.13 (d, J = 2.5 Hz, 1H), 8.37 (dd, J = 8.7, 2.6 Hz, 1H), 7.74 (d, J = 8.7 Hz, 1H), 4.97 (d, J = 6.3 Hz, 1H), 3.04-2.96 (m, 2H), 2.38 (s, 6H), 1.33 (t, J = 7.5 Hz, 3H), 0.98-0.80 (m, 3H), 0.63-0.55 (m, 1H), 0.55-0.46 (m, 2H), 0.46-0.38 (m, 1H), 0.34 (ddd, J = 10.1, 8.0, 4.8 Hz, 3H), 0.25 (dq, J = 9.2, 4.3 Hz, 1H). MS m/z: 464 (M + 1)$^+$. |

-continued

| Examples | Formula | Carboxylic acid | Amine, reactant | $^1$HNMR and/or LCMS |
|---|---|---|---|---|
| 44 | 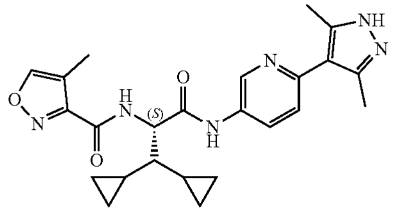 | 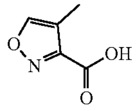 | 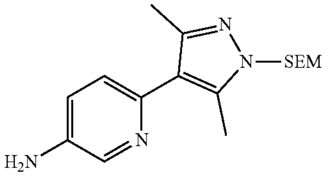 Z2 | $^1$H NMR (400 MHz, Methanol-$d_4$) δ 9.19 (d, J = 2.5 Hz, 1H), 8.56 (d, J = 1.2 Hz, 1H), 8.41 (dd, J = 8.8, 2.6 Hz, 1H), 7.81 (d, J = 8.8 Hz, 1H), 4.94 (d, J = 6.0 Hz, 1H), 2.38 (s, 6H), 2.21 (d, J = 1.0 Hz, 3H), 0.96-0.83 (m, 3H), 0.64-0.39 (m, 4H), 0.33 (p, J = 4.8 Hz, 3H), 0.25 (dq, J = 9.1, 4.5 Hz, 1H). MS m/z: 449 (M + 1)$^+$. |
| 45 | 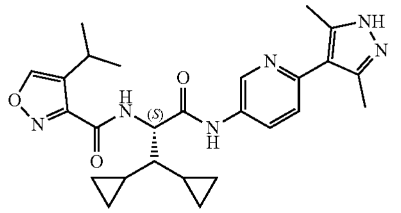 | 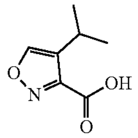 | 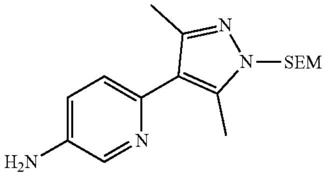 Z2 | $^1$H NMR (400 MHz, Methanol-$d_4$) δ 9.22 (d, J = 2.5 Hz, 1H), 8.60 (d, J = 0.8 Hz, 1H), 8.43 (dd, J = 8.8, 2.5 Hz, 1H), 7.84 (d, J = 8.8 Hz, 1H), 4.94 (d, J = 6.1 Hz, 1H), 3.22 (pd, J = 6.9, 0.9 Hz, 1H), 2.39 (s, 6H), 1.25 (t, J = 7.1 Hz, 6H), 0.98-0.78 (m, 3H), 0.59 (tdd, J = 8.8, 5.3, 2.9 Hz, 1H), 0.55-0.47 (m, 2H), 0.47-0.39 (m, 1H), 0.33 (hept, J = 4.2 Hz, 3H), 0.25 (dq, J = 9.1, 4.5 Hz, 1H). MS m/z: 477(M + 1)$^+$. |
| 46 | 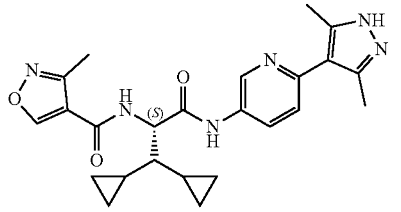 | 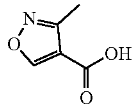 | 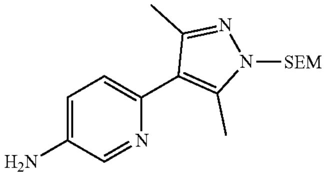 Z2 | 1H NMR (400 MHz, Methanol-$d_4$) δ 9.09 (d, J = 2.5 Hz, 1H), 8.36 (dd, J = 8.8, 2.6 Hz, 1H), 8.07 (s, 1H), 7.74 (d, J = 8.7 Hz, 1H), 4.54 (d, J = 5.7 Hz, 1H), 2.39 (s, 6H), 2.19 (s, 3H), 0.91 (td, J = 9.2, 5.7 Hz, 1H), 0.86-0.72 (m, 2H), 0.65 (dp, J = 8.7, 4.7 Hz, 1H), 0.58 (td, J = 9.1, 4.8 Hz, 1H), 0.51 (dq, J = 8.6, 4.9, 4.4 Hz, 2H), 0.34 (dtq, J = 19.8, 9.5, 4.9 Hz, 3H), 0.20 (dq, J = 9.7, 5.0 Hz, 1H). MS m/z: 449 (M + 1)$^+$. |
| 47 | 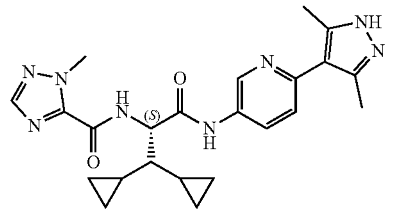 | 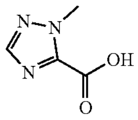 | 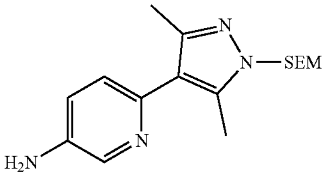 Z2 | $^1$H NMR (400 MHz, Methanol-$d_4$) δ 9.23 (d, J = 2.4 Hz, 1H), 8.44 (dd, J = 8.8, 2.5 Hz, 1H), 7.98 (s, 1H), 7.85 (d, J = 8.8 Hz, 1H), 4.91 (d, J = 5.6 Hz, 1H), 4.22 (s, 3H), 2.39 (s, 6H), 0.97-0.82 (m, 3H), 0.64-0.52 (m, 2H), 0.52-0.40 (m, 2H), 0.40-0.30 (m, 3H), 0.26 (dq, J = 9.2, 4.4 Hz, 1H). MS m/z: 449 (M + 1)$^+$. |

-continued

| Examples | Formula | Carboxylic acid | Amine, reactant | $^1$HNMR and/or LCMS |
|---|---|---|---|---|
| 48 | 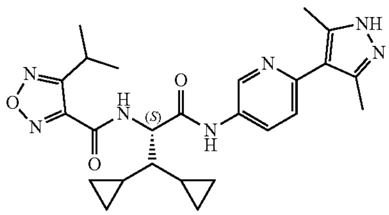 | 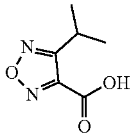 | 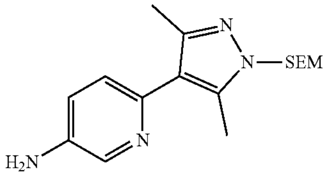 Z2 | $^1$H NMR (400 MHz, Methanol-$d_4$) δ 9.15 (d, 2.5 Hz, 1H), 8.38 (dd, J = 8.7, 2.6 Hz, 1H), 7.76 (d, J = 8.8 Hz, 1H), 4.97 (d, J = 6.1 Hz, 1H), 3.53-3.45 (m, 1H), 2.38 (s, 6H), 1.42-1.32 (m, 6H), 0.97-0.84 (m, 3H), 0.60-0.25 (m, 8H). MS m/z: 478 (M + 1)$^+$. |
| 49 | 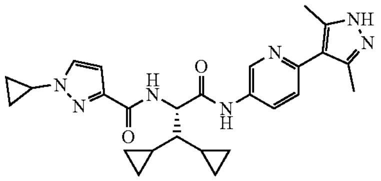 [SMILES: Cc1n[nH]c(C)c1-c1ccc(NC(=O)[C@@H](NC(=O)c2ccn(C3CC3)n2)C(C2CC2)C2CC2)cn1] | 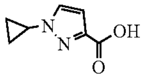 | 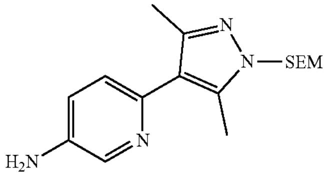 Z2 | $^1$H NMR (400 MHz, Methanol-$d_4$) δ 9.27 (d, J = 2.4 Hz, 1H), 8.46 (dd, J = 8.8, 2.5 Hz, 1H), 7.87 (d, J = 8.8 Hz, 1H), 7.43 (d, J = 2.0 Hz, 1H), 6.80 (d, J = 2.0 Hz, 1H), 4.93 (d, J = 7.0 Hz, 1H), 4.17 (tt, J = 7.5, 3.9 Hz, 1H), 2.39 (s, 6H), 1.13 (dq, J = 3.8, 2.4, 1.7 Hz, 2H), 0.98 (dddd, J = 17.3, 10.1, 5.9, 2.6 Hz, 3H), 0.87 (td, J = 8.2, 5.4 Hz, 2H), 0.60 (tt, J = 9.2, 4.3 Hz, 1H), 0.55-0.45 (m, 2H), 0.45-0.28 (m, 4H), 0.24 (dt, J = 9.3, 4.5 Hz, 1H). MS m/z: 474(M + 1)$^+$. |
| 50 | 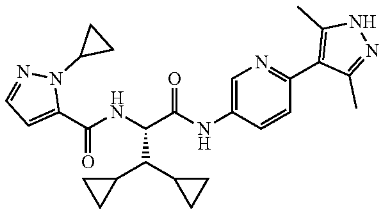 [SMILES: Cc1n[nH]c(C)c1-c1ccc(NC(=O)[C@@H](NC(=O)c2ccnn2C2CC2)C(C2CC2)C2CC2)cn1] | 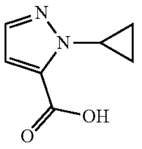 [SMILES: O=C(O)c1ccnn1C1CC1] | 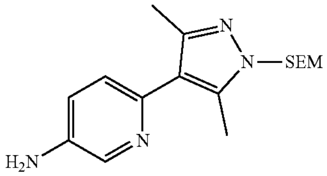 Z2 | $^1$H NMR (400 MHz, Methanol-$d_4$) δ 9.20 (d, J = 2.5 Hz, 1H), 8.42 (dd, J = 8.8, 2.6 Hz, 1H), 7.81 (d, J = 8.8 Hz, 1H), 7.76 (d, J = 2.4 Hz, 1H), 6.73 (d, J = 2.4 Hz, 1H), 4.90 (d, J = 6.0 Hz, 1H), 3.79 (tt, J = 7.4, 3.8 Hz, 1H), 2.38 (s, 6H), 1.23-1.16 (m, 2H), 1.09 (tdd, J = 7.3, 4.9, 2.7 Hz, 2H), 0.95-0.79 (m, 3H), 0.56 (dt, J = 16.1, 6.5 Hz, 2H), 0.52-0.39 (m, 2H), 0.33 (ddt, J = 9.1, 6.5, 3.8 Hz, 3H), 0.24 (dq, J = 9.2, 4.6 Hz, 1H). MS m/z: 474 (M + 1)$^+$. |

-continued

| Examples | Formula | Carboxylic acid | Amine, reactant | $^1$HNMR and/or LCMS |
|---|---|---|---|---|
| 51 | 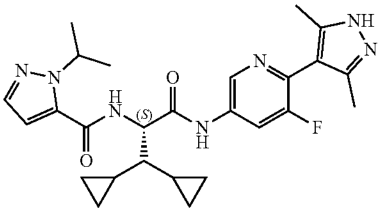 | 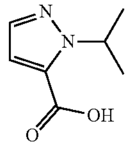 | 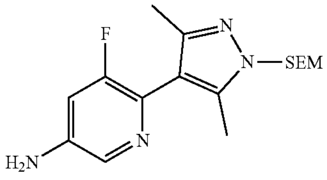 Z3 | $^1$H NMR (400 MHz, Methanol-$d_4$) δ 8.62 (d, J = 2.0 Hz, 1H), 8.22 (dd, J = 11.7, 2.1 Hz, 1H), 7.52 (d, J = 1.9 Hz, 1H), 6.80 (d, J = 2.0 Hz, 1H), 5.47-5.32 (m, 1H), 4.91 (dd, J = 7.5, 5.3 Hz, 1H), 2.26 (s, 6H), 1.45 (dd, J = 6.6, 5.4 Hz, 6H), 0.99-0.75 (m, 3H), 0.63-0.43 (m, 3H), 0.43-0.26 (m, 4H), 0.26-0.17 (m, 1H). MS m/z: 494 $(M + 1)^+$. |
| 52 | 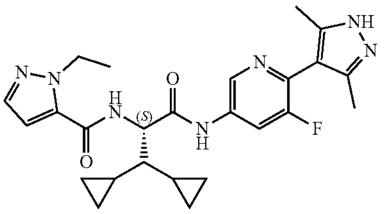 | 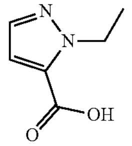 | 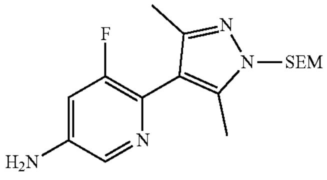 Z3 | $^1$H NMR (400 MHz, Methanol-$d_4$) δ 8.70-8.58 (m, 1H), 8.29-8.15 (m, 1H), 7.51 (d, J = 2.1 Hz, 1H), 6.88 (d, J = 2.1 Hz, 1H), 4.66-4.39 (m, 2H), 2.29 (d, J = 1.1 Hz, 6H), 1.46-1.32 (m, 3H), 0.94-0.77 (m, 3H), 0.65-0.43 (m, 3H), 0.43-0.28 (m, 4H), 0.28-0.18 (m, 1H). MS m/z: 480 $(M + 1)^+$. |

Example 51 Preparation of Compound 51

The compound 51 is prepared through the following route:

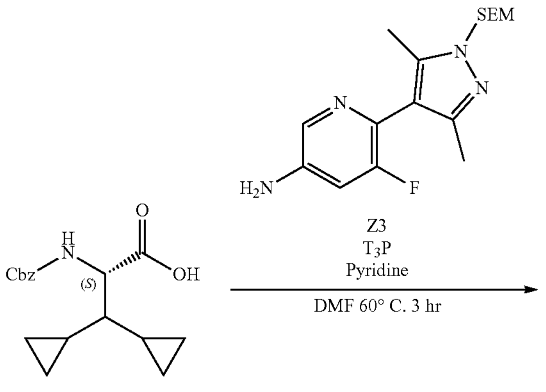

Intermediate-2

-continued

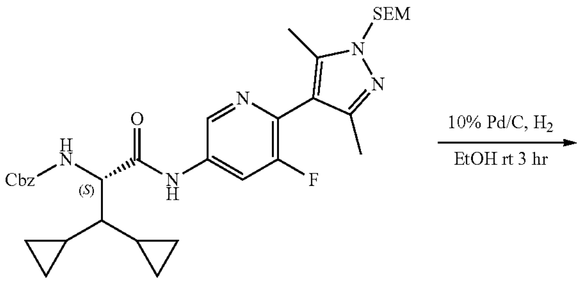

51-1

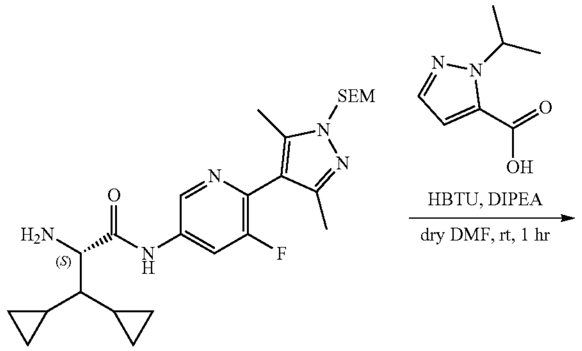

51-2

-continued

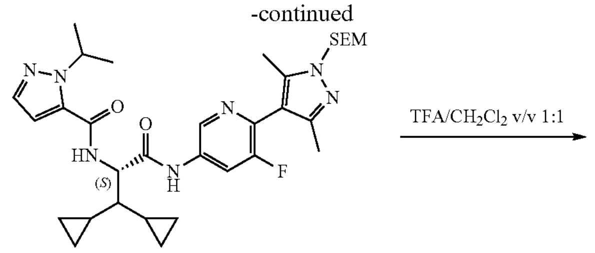

51-3

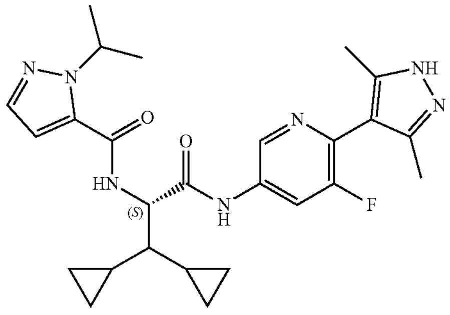

51

Step 1 Preparation of Intermediate 51-1

To a 100 mL single-necked flask was added 5.0 g of the intermediate 2 (16.50 mmol), 6.65 g of the intermediate Z3 (19.80 mmol), 45 mL of DMF in sequence, then added 13.0 g of pyridine (165 mmol) and 31.5 g of 1-propylphosphonic anhydride (T3P, 99 mmol) in sequence. The reaction mixture was heated to 60° C. and stirred for 1 h. When LC-MS detected that the reaction completed, the reaction mixture was concentrated under reduced pressure to remove most of DMF and pyridine to obtain a crude product, which was directly separated and purified by MPLC column chromatography to give 9.53 g of the intermediate 51-1 (15.70 mmol) with a yield of 93%. MS m/z: 622 $(M+1)^+$.

Step 2 Preparation of Intermediate 51-2

To a 250 mL single-necked flask was added 9.53 g of the intermediate 1 (15.70 mmol), 150 mL of EtOH in sequence, then add 2.86 g of 10% Pd/C (w/w 30%) under nitrogen protection. The reaction mixture was reacted under stirring in the presence of hydrogen, where hydrogen was replaced for three times. Then the reaction mixture was reacted under stirring under hydrogen atmosphere at room temperature for 3 h. When LC-MS detected that the reaction completed, the reaction mixture was filtered through a Buchner funnel with diatomite, and washed with ethanol. The filtrate was combined, and concentrated under reduced pressure to give 7.2 g of the intermediate 51-2 (14.78 mmol) with a yield of 94%. MS m/z: 488 $(M+1)^+$.

Step 3 Preparation of Intermediate 51-3

To a 250 mL single-necked flask was added 7.2 g of the intermediate 51-2 (14.78 mmol), 2.73 g of intermediate 2-isopropyl-3-pyrazolecarboxylic acid (17.74 mmol), 60 mL of DMF successively, and then successively added 7.28 g of HBTU (19.22 mmol) and 7.63 g of DIPEA (59.14 mmol, 10.5 mL) under ice bath and stirring. The reaction mixture was reacted under stirring for 10 min under ice bath, and then restored to room temperature for 1 h. When LC-MS detected that the reaction completed, the reaction mixture was added with 180 mL of ethyl acetate, washed with saturated NaCl solution (180 ml*2). The organic phase was dried with anhydrous sodium sulfate, filtered, concentrated under reduced pressure to obtain a crude product, which was further purified by MPLC column chromatography to give 9.2 g of the intermediate 51-3 (14.77 mmol) with a yield of 99% yield. MS m/z: 624 $(M+1)^+$.

Step 4 Preparation of Compound 51

To a 250 mL single-necked flask was successively added 9.2 g of the intermediate 51-3 (14.77 mmol) and 35 mL of $CH_2Cl_2$, and then added 35 mL of TFA under ice bath and stirring. Then the reaction mixture was restored to room temperature, stirred for 3h, and concentrated under reduce pressure to obtain a crude product, which was further purified by MPLC column chromatography to obtain 6.0 g of the compound 51 (12.17 mmol) with a yield of 82%). MS m/z: 494 $(M+1)^+$.

$^1H$ NMR (400 MHz, Methanol-$d_4$) δ 8.62 (d, J=2.0 Hz, 1H), 8.22 (dd, J=11.7, 2.1 Hz, 1H), 7.52 (d, J=1.9 Hz, 1H), 6.80 (d, J=2.0 Hz, 1H), 5.47-5.32 (m, 1H), 4.91 (dd, J=7.5, 5.3 Hz, 1H), 2.26 (s, 6H), 1.45 (dd, J=6.6, 5.4 Hz, 6H), 0.99-0.75 (m, 3H), 0.63-0.43 (m, 3H), 0.43-0.26 (m, 4H), 0.26-0.17 (m, 1H).

Examples 53-59 Preparation of Compounds 53-59

Similarly, compounds 53-59 were synthesized through the route illustrated in Example 37. Briefly, the intermediate 3, which was shown as

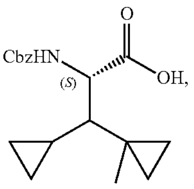

underwent condensation with amine Z2 or amine Z3; in step 2, the benzyloxycarbonyl (Cbz) protecting group was removed by Pd/C-catalyzed hydrogenation; and in step 3, the hydrogenated product underwent condensation with other carboxylic acids shown in the following table, and the SEM protecting group was removed.

| Ex-am-ples | Formula | Carboxylic acid | Amine, reactant | $^1$HNMR and/or LCMS |
|---|---|---|---|---|
| 53 | 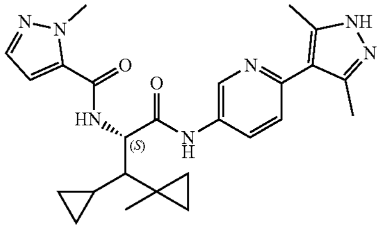 | 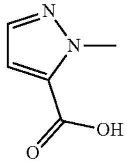 | 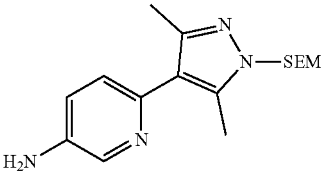 Z2 | $^1$H NMR (400 MHz, Methanol-$d_4$) δ 8.82 (dd, J = 2.7, 0.7 Hz, 1H), 8.16 (dd, J = 8.5, 2.6 Hz, 1H), 7.49 (d, J = 2.1 Hz, 1H), 7.43 (dd, J = 8.5, 0.8 Hz, 1H), 6.85 (d, J = 2.1 Hz, 1H), 5.07 (d, J = 9.2 Hz, 1H), 4.11 (s, 3H), 2.34 (s, 6H), 1.26 (s, 3H), 0.96-0.86 (m, 1H), 0.74 (dd, J = 10.3, 9.2 Hz, 1H), 0.54-0.45 (m, 3H), 0.45-0.36 (m, 1H), 0.36-0.28 (m, 3H), 0.22-0.15 (m, 1H). MS m/z: 462 (M + 1)$^+$. |
| 54 | 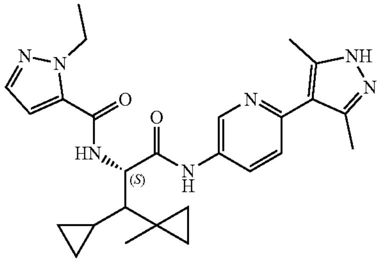 | 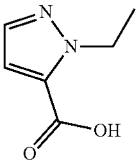 | 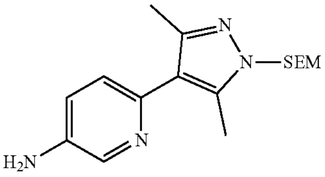 Z2 | $^1$H NMR (400 MHz, Methanol-$d_4$) δ 8.82 (dd, J = 2.6, 0.7 Hz, 1H), 8.16 (dd, J = 8.6, 2.6 Hz, 1H), 7.51 (d, J = 2.1 Hz, 1H), 7.44 (dd, J = 8.6, 0.8 Hz, 1H), 6.84 (d, J = 2.1 Hz, 1H), 5.07 (d, J = 9.1 Hz, 1H), 4.56 (dt, J = 7.9, 6.0 Hz, 2H), 2.34 (s, 6H), 1.40 (t, J = 7.2 Hz, 3H), 1.26 (s, 3H), 0.92 (dd, J = 9.2, 4.2 Hz, 1H), 0.78-0.70 (m, 1H), 0.54-0.45 (m, 3H), 0.45-0.37 (m, 1H), 0.33 (t, J = 4.8 Hz, 3H), 0.23-0.15 (m, 1H). MS m/z: 476(M + 1)$^+$. |
| 55 | 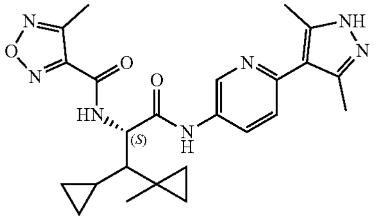 | 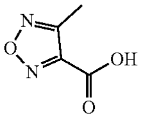 | 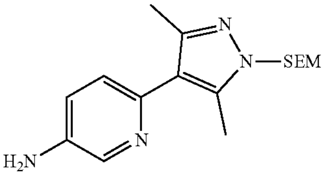 Z2 | $^1$H NMR (400 MHz, Methanol-$d_4$) δ 8.80 (dd, J = 2.6, 0.7 Hz, 1H), 8.16 (dd, J = 8.6, 2.7 Hz, 1H), 7.43 (dd, J = 8.5, 0.8 Hz, 1H), 5.08 (d, J = 8.9 Hz, 1H), 2.55 (s, 3H), 2.33 (s, 6H), 1.25 (s, 3H), 0.92-0.88 (m, 1H), 0.76 (dd, J = 10.4, 8.9 Hz, 1H), 0.55-0.49 (m, 2H), 0.49-0.38(m, 2H), 0.37-0.28(m, 3H), 0.23-0.15(m, 1H). MS m/z: 464(M + 1)$^+$. |
| 56 | 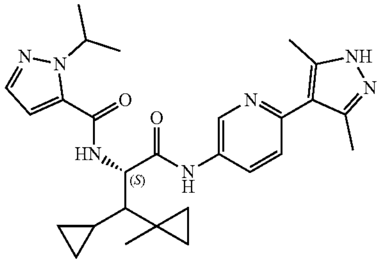 | 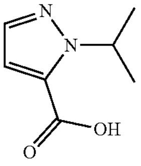 | 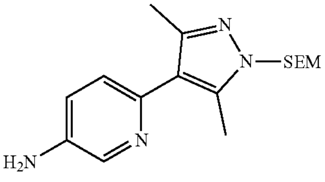 Z2 | $^1$H NMR (400 MHz, Methanol-$d_4$) δ 8.87-8.77 (m, 1H), 8.16 (dd, J = 8.6, 2.6 Hz, 1H), 7.52 (d, J = 2.1 Hz, 1H), 7.43 (dd, J = 8.5, 0.7 Hz, 1H), 6.77 (d, J = 2.1 Hz, 1H), 5.43 (p, J = 6.6 Hz, 1H), 5.08 (d, J = 9.2 Hz, 1H), 2.35 (s, 6H), 1.46 (dd, J = 9.1, 6.6 Hz, 6H), 1.27 (s, 3H), 0.97-0.87 (m, 1H), 0.74 (dd, J = 10.3, 9.2 Hz, 1H), 0.56-0.46 (m, 3H), 0.46-0.38 (m, 1H), 0.34 (dp, J = 5.2, |

-continued

| Ex-am-ples | Formula | Carboxylic acid | Amine, reactant | $^1$HNMR and/or LCMS |
|---|---|---|---|---|
| | | | | 1.6 Hz, 3H), 0.24-0.15 (m, 1H). MS m/z: 490 $(M + 1)^+$. |
| 57 | 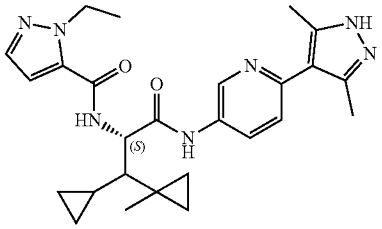 | 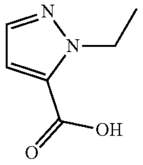 | 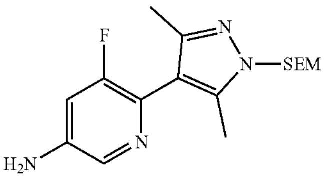 Z3 | $^1$H NMR (400 MHz, Methanol-$d_4$) δ 8.61 (dd, J = 2.2, 0.9 Hz, 1H), 8.20 (dd, J = 11.6, 2.1 Hz, 1H), 7.51 (d, J = 2.1 Hz, 1H), 6.84 (d, J = 2.1 Hz, 1H), 5.06 (d, J = 9.1 Hz, 1H), 4.55 (qd, J = 7.2, 1.4 Hz, 2H), 2.23 (d, J = 1.1 Hz, 6H), 1.45-1.34 (m, 4H), 1.37-1.26 (m, 14H), 1.25 (s, 4H), 0.98-0.83 (m, 4H), 0.80-0.71 (m, 1H), 0.56-0.46 (m, 3H), 0.50-0.37 (m, 2H), 0.38-0.28 (m, 3H), 0.23-0.13 (m, 1H). MS m/z: 494$(M + 1)^+$. |
| 58 | 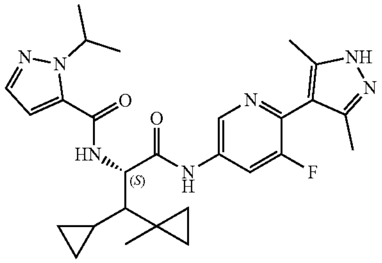 | 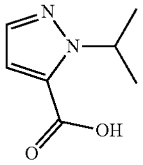 | 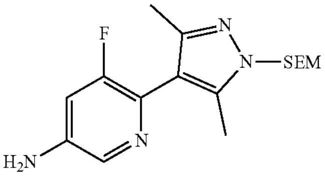 Z3 | $^1$H NMR (400 MHz, Methanol-$d_4$) δ 8.61 (dd, J = 2.1, 1.0 Hz, 1H), 8.20 (dd, J = 11.6, 2.1 Hz, 1H), 7.52 (d, J = 2.1 Hz, 1H), 6.77 (d, J = 2.0 Hz, 1H), 5.49-5.34 (m, 1H), 5.06 (d, J = 9.1 Hz, 1H), 4.58 (s, 1H), 3.03 (q, J = 7.3 Hz, 3H), 2.23 (d, J = 1.2 Hz, 6H), 1.50-1.39 (m, 8H), 1.37-1.22 (m, 14H), 1.23-1.17 (m, 1H), 1.17-1.08 (m, 1H), 0.96-0.87 (m, 2H), 0.79-0.69 (m, 2H), 0.55-0.49 (m, 2H), 0.50-0.37 (m, 2H), 0.37-0.28 (m, 3H), 0.22-0.13 (m, 1H). MS m/z: 508 $(M + 1)^+$. |
| 59 | 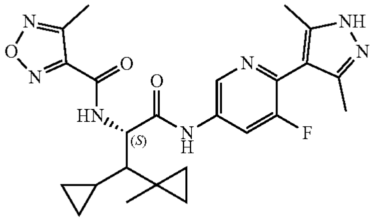 | 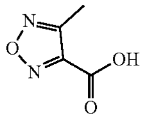 | 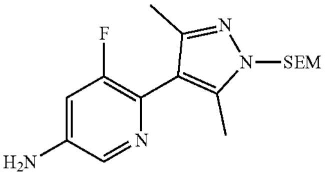 Z3 | $^1$H NMR (400 MHz, Methanol-$d_4$) δ 8.60 (dd, J = 2.1, 1.0 Hz, 1H), 8.20 (dd, J = 11.7, 2.1 Hz, 1H), 5.08 (d, J = 8.9 Hz, 1H), 2.56 (s, 6H), 1.95-1.82 (m, 2H), 1.83-1.71 (m, 1H), 1.48 (s, 2H), 1.37-1.26 (m, 4H), 1.25 (s, 4H), 1.05-0.97 (m, 3H), 0.97-0.83 (m, 3H), 0.82-0.72 (m, 2H), 0.56-0.50 (m, 4H), 0.49-0.39 (m, 5H), 0.37-0.29 (m, 6H), 0.29-0.08 (m, 2H). MS m/z: 482 $(M + 1)^+$. |

Examples 60-62 Preparation of Compounds 60-62

Similarly, compounds 60-62 were synthesized through the route A in combination with operation steps described in Example 1. Briefly, the amino acid, which was shown as

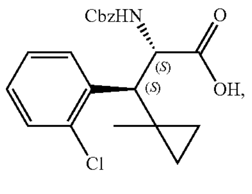

underwent condensation with amine correspondingly shown in the following table; in step 2, the benzyloxycarbonyl (Cbz) protecting group was removed by Pd/C-catalyzed hydrogenation; and in step 3, the hydrogenated product underwent condensation with 1-methylpyrazole-5-carboxylic acid.

| Examples | Formula | Amino acid, starting material | Amine, reactant | $^1$HNMR and/or LCMS |
|---|---|---|---|---|
| 60 | 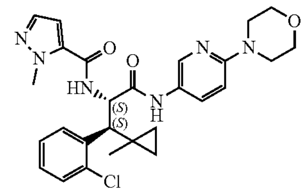 | 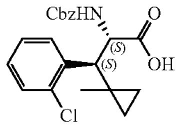 | 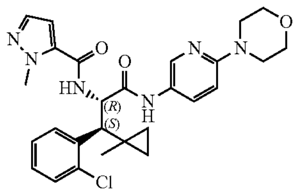 | $^1$H NMR (400 MHz, Methanol-$d_4$) δ 8.70-8.62 (m, 1H), 8.08 (dd, J = 9.6, 2.6 Hz, 1H), 7.50-7.40 (m, 2H), 7.35-7.29 (m, 2H), 7.29-7.18 (m, 2H), 6.31 (d, J = 2.1 Hz, 1H), 5.41 (d, J = 11.7 Hz, 1H), 3.90-3.83 (m, 7H), 3.64-3.58 (m, 4H), 3.55 (d, J = 11.7 Hz, 1H), 1.19 (s, 3H), 0.93 (dt, J = 9.9, 5.1 Hz, 1H), 0.59 (dt, J = 9.8, 5.1 Hz, 1H), 0.32 (ddd, J = 10.0, 5.8, 4.3 Hz, 1H), 0.13 (ddd, J = 9.2, 5.8, 4.5 Hz, 1H). MS m/z: 524 $(M + 1)^+$. |
| 61 | 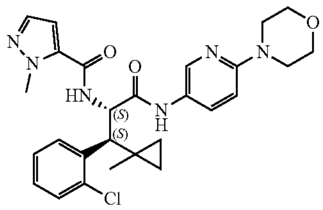 | 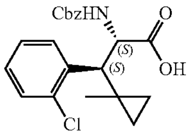 | 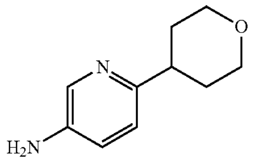 | $^1$H NMR (400 MHz, Methanol-$d_4$) δ 8.72 (dd, J = 2.6, 0.7 Hz, 1H), 8.09 (dd, J = 8.5, 2.6 Hz, 1H), 7.39 (td, J = 8.3, 1.6 Hz, 2H), 7.31 (d, J = 8.5 Hz, 1H), 7.24 (d, J = 2.1 Hz, 1H), 7.24-7.17 (m, 1H), 7.20-7.10 (m, 1H), 6.24 (d, J = 2.1 Hz, 1H), 5.37 (d, J = 11.6 Hz, 1H), 4.06-3.94 (m, 3H), 3.79 (s, 3H), 3.58-3.44 (m, 3H), 2.99-2.86 (m, 1H), 1.92-1.71 (m, 4H), 1.23 (s, 2H), 1.14 (s, 3H), 0.85 (m, 2H), 0.55 (m, 1H), 0.25 (m, 1H). MS m/z: 522 $(M + 1)^+$. |

-continued

| Ex-amples | Formula | Amino acid, starting material | Amine, reactant | $^1$HNMR and/or LCMS |
|---|---|---|---|---|
| 62 | 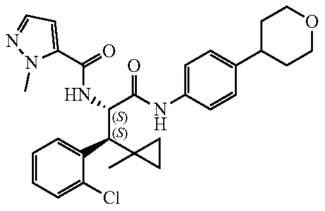 | 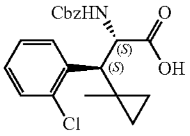 | 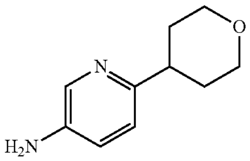 | $^1$H NMR (400 MHz, Methanol-d4) δ 7.63-7.55 (m, 2H), 7.44 (ddd, J = 17.6, 7.9, 1.6 Hz, 2H), 7.29-7.23 (m, 4H), 7.20 (td, J = 7.6, 1.7 Hz, 1H), 7.07 (q, J = 8.7 Hz, 1H), 6.28 (d, J = 2.1 Hz, 1H), 5.41 (d, J = 11.7 Hz, 1H), 4.06-4.01 (m, 2H), 3.81 (s, 3H), 3.59-3.51 (m, 3H), 2.84-2.75 (m, 1H), 1.82-1.73 (m, 4H), 1.20 (s, 3H), 0.89 (dt, J = 10.0, 5.1 Hz, 1H), 0.63 (dt, J = 9.9, 5.1 Hz, 1H), 0.31 (dt, J = 10.0, 5.1 Hz, 1H), 0.09 (dq, J = 9.5, 4.9 Hz, 1H). MS m/z: 522 $(M + 1)^+$. |

The beneficial effects of this application will be demonstrated below with reference to the Experimental Examples.

Experimental Example 1 IL-17A Enzyme-Linked Immunosorbent Assay (ELISA)

The inhibition of receptor-ligand binding by human IL-17A inhibitors was quantified by competitive ELISA. 0.2 μg/mL of IL-17A (Sino Biological Inc. Cat #12047-H07B) was added in a 96-well plate at 100 μl per well for incubation for 30 min under 37° C. The 96-well plate was washed with PBST (PBS, 0.05% Tween-20) at 200 μl per well for 4 times, and then added with 200 μl of 5% skim milk and placed on a shaker for incubation at 25° C. for 30 min. The compound to be tested was prepared at 100× concentration ranging from 0.003 μM to 30 μM. After washed with PBST (PBS, 0.05% Tween-20) 4 times, the plate was added with 89 μl of PBST and 1 μl of the compound to be tested at 100× concentration followed by uniformly mixing and pre-incubation at 25° C. for 10 min. Then the plate was added with 10 μl of 16 nM IL-17R, and incubated on a shaker at 25° C. for 30 min. After washed for 4 times, the plate was added with 100 μl of anti-Fc-tag horseradish peroxidase (HRP)-conjugated antibody, and incubated on a shaker at 25° C. for 30 min. After washed 4 times, the plate was added with 100 μl of 3,3', 5,5"-tetramethylbenzidine (TMB) substrate solution, and incubated at 25° C. in the dark. Then the plate was added with 20% HCl, followed by detection of the light absorption value at a wavelength of 450 nm by a microplate reader. The compounds prepared in the above examples were tested for human IL-17A inhibitory activity according to the above method.

Experimental Example 2 Inhibition of Chemokine GROα/CXCL1 Generation Induced by Human IL-17A Protein in HT-29 Cell (Human Colon Cancer Cell Line)

HT-29 (Zhongyuan Gongchuang Technology Co., Ltd. of Chengdu, Sichuan) was added to a 96-well plate at 5×104 cells/well, and cultured overnight in a incubator at 37° C. A mixture of 30 ng/mL of human IL-17A protein (R&D, #317-ILB) and IL-17A small molecule inhibitors with gradient concentrations or 0.3 μg/mL of positive control IL-17A antibody (R&D, #AF-317-NA) was incubated at 37° C. for 1 h, and then added to the above-mentioned 96-well plate, and incubated with HT-29 cells at 37° C. for 48 hours. Then the GROα level in the cell culture supernatant was detected by an ELISA kit (Cisbio, #62HCXC1PEG) of the GROα.

According to the methods described in Experimental Examples 1 and 2, the compounds prepared in the above-mentioned examples were subjected to the experiment on inhibition of chemokine GROα/CXCL1 generation induced by human IL-17A protein in HT-29 cell. The results demonstrated in Table 1 showing the ELISA $IC_{50}$ value and $IC_{50}$ inhibitory activity for inhibiting GROα/CXCL1 in HT-29 cell of each above-prepared compound, where "–" means not tested.

TABLE 1

Inhibitory activity of above-prepared compounds against human IL-17A

| Examples | ELISA $IC_{50(⊙o⊙)}$ . . . (μmol) | HT-29 $IC_{50}$ (μmol) | Examples | ELISA $IC_{50}$ (μmol) | HT-29 $IC_{50}$ (μmol) | Examples | ELISA $IC_{50}$ (μmol) | HT-29 $IC_{50}$ (μmol) | Examples | ELISA $IC_{50}$ (μmol) | HT-29 $IC_{50}$ (μmol) |
|---|---|---|---|---|---|---|---|---|---|---|---|
| 2 | 0.066 | 0.555 | 3 | 0.067 | 1.57 | 4 | 0.064 | 0.598 | 8 | 0.236 | — |
| 10 | 0.041 | 7.398 | 11 | 0.056 | 10.77 | 12 | 0.040 | 13.62 | 13 | 0.642 | — |
| 14 | 0.021 | 7.275 | 15 | 0.049 | 2.82 | 16 | 0.100 | 11.68 | 17 | 0.136 | — |
| 18 | 0.247 | — | 19 | 0.073 | 3.157 | 20 | 9.344 | — | 21 | 16.87 | — |
| 22 | 13.71 | — | 23 | 0.043 | 0.065 | 24 | >40 | — | 25 | 0.032 | 0.420 |
| 26 | 0.096 | 0.250 | 27 | 0.104 | 1.077 | 36 | 1.285 | — | | | |
| 37 | 0.018 | 0.257 | 38 | 0.385 | 4.462 | 39 | 0.128 | 0.514 | 40 | 0.117 | 0.781 |
| 41 | 1.141 | 1.473 | 42 | 0.170 | — | 43 | 0.457 | — | 44 | 2.778 | — |
| 45 | 0.511 | — | 46 | 0.111 | 0.856 | 47 | 15.50 | — | 48 | 0.157 | 3.025 |
| 49 | 0.537 | — | 50 | 27.92 | — | 51 | 0.042 | 0.224 | 52 | 0.098 | 0.321 |

TABLE 1-continued

| Inhibitory activity of above-prepared compounds against human IL-17A | | | | | | | | | | | |
|---|---|---|---|---|---|---|---|---|---|---|---|
| Examples | ELISA $IC_{50(\odot 0 \odot)}$ . . . (μmol) | HT-29 $IC_{50}$ (μmol) | Examples | ELISA $IC_{50}$ (μmol) | HT-29 $IC_{50}$ (μmol) | Examples | ELISA $IC_{50}$ (μmol) | HT-29 $IC_{50}$ (μmol) | Examples | ELISA $IC_{50}$ (μmol) | HT-29 $IC_{50}$ (μmol) |
| 53 | 0.055 | 0.472 | 54 | 0.047 | 0.238 | 55 | 0.053 | 0.866 | 56 | 0.035 | 0.087 |
| 57 | 0.026 | 0.203 | 58 | 0.042 | 0.221 | 59 | 0.087 | 4.676 | 60 | 0.327 | 8.017 |
| 61 | 0.007 | 1.996 | 62 | 0.056 | 0.373 | | | | | | |

Experimental Example 3 Pharmacokinetic Properties of Compounds Prepared in Above Examples in Rats, Mice and Dogs In order to investigate the pharmacokinetic properties of the compound in rats, 3 rats were administered with the compounds at corresponding doses by intravenous injection/oral gavage, respectively. The anticoagulated whole blood of the rats were collected and the plasma was separated at 5 min, 15 min, 30 min, 1 h, 2 h, 4 h, 8 h, 24 h after administrated. In order to investigate the pharmacokinetic properties of the compound in mice, 6 mice were administered with the compound at the corresponding dose by intravenous injection/oral gavage. The mice administered by each route were divided into A group and B group. The anticoagulated whole blood was collected from the mice in group A at 5 min, 30 min, 2 h, and 8 h after the administration, and the anticoagulated whole blood was collected from the mice in group B at 15 min, 1 h, 4 h, and 24 h after the administration, and plasma was separated. In order to investigate the pharmacokinetic properties of dogs, two groups of 4 beagle dogs (2 males+2 females) were administered with the compound at corresponding doses by intravenous injection/oral gavage. The anticoagulated whole blood of each dog was collected, and the plasma was separated at 2 h, 4 h, 8 h, 12 h, 24 h, 36 h after the administration.

Plasma concentrations of compounds were determined by standard curve calibration by LC-MS. The plasma concentration-time data, including elimination half-life (T1/2), area under the curve of the last sampling time (AUClast), peak concentration (Cmax), apparent volume of distribution (Vz), total body clearance (Cl), absolute bioavailability (F %), etc., were fitted to pharmacokinetic parameters by using Winnolin 5.2 software. The oral bioavailability F % of a representative Compound 51 is listed in Table 2.

TABLE 2

| Oral Bioavailability F % | | | |
|---|---|---|---|
| Examples | F % (Mice) | F % (Rats) | F %(Dogs) |
| 51 | 56 | 46 | 58 |

Experimental Example 4 Cytochrome P450 (CYP) Enzyme Induction Test

In order to evaluate the induction of CYP enzymes in human hepatocytes by the compounds prepared in the above examples at 10 μM, Omeprazole (positive control) and the compound prepared in Example 32 (control compound 2) disclosed in patent application. WO2020/127685A1 were used as controls. The results were demonstrated in Table 3 showing that the compound 51 prepared in this application has no inducing effect on cytochrome P450 1A2 (CYP1A2), and may become a safer drug for IL-17A inhibitor.

TABLE 3

| CYP enzyme induction results | | | | |
|---|---|---|---|---|
| | | mRNA Expression level | | |
| Testing item | Concentration (μM) | Fold of induction 1A2 | % of the positive control 1A2 | Note 1A2 |
| DMSO | — | — | — | — |
| Omeprazole (Positive control) | 25/750 | 12.8 | — | — |
| Control compound 2 | 10 | 2.21 | 10.3 | Induction |
| Compound 51 prepared in Examples51 | | 1.26 | 2.20 | Non-induction |

Figure 1B:
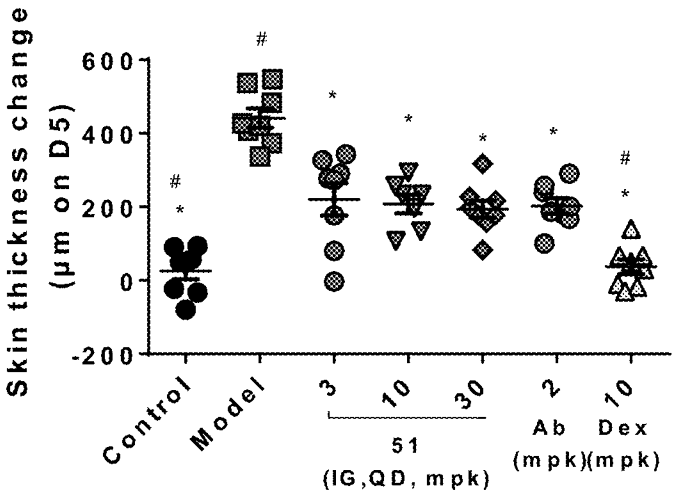

Experimental Example 5 Pharmacodynamic Test on an Imiquimod Cream-Induced Psoriasis Model in Mice Each 10-week-old female C57 black 6 (C57BL/6N) mouse was shaved to approximately 2.5×4 cm on the back, which the imiquimod (IMQ, Imiquimod) cream continuously applies from the day 1-4, so as to establish a psoriasis model. Each mouse was administrated with the compound 51 prepared in this application by gavage (3, 10, 30 mg/kg) once a day, and administrated with IL-17A antibody solution by intraperitoneal injection (Ab, 2 mg/kg) every other day, or administrated with dexamethasone solution by intraperitoneal injection (10 mg/kg) once a day. According to the area under the curve (AUC, shown in FIG. 1A) of the psoriasis area and severity index (PASI) scoring curve, different doses of the compound reduced the level of skin inflammation induced by IMQ, which has the effect similar to that of IL-17A antibody. On day 1 and day 5 of the experiment, the skin thickness of the mice was measured to investigate the skin thickening induced by IMQ. The results were shown in FIG. 1B, which demonstrated that administration of compound 51 and IL-17A antibody in each group reversed the skin thickening caused by IMQ at different levels.

Figure 1C:
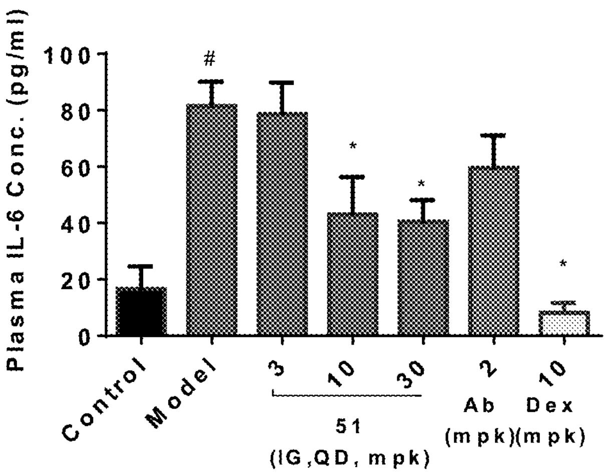
Figure 1D:
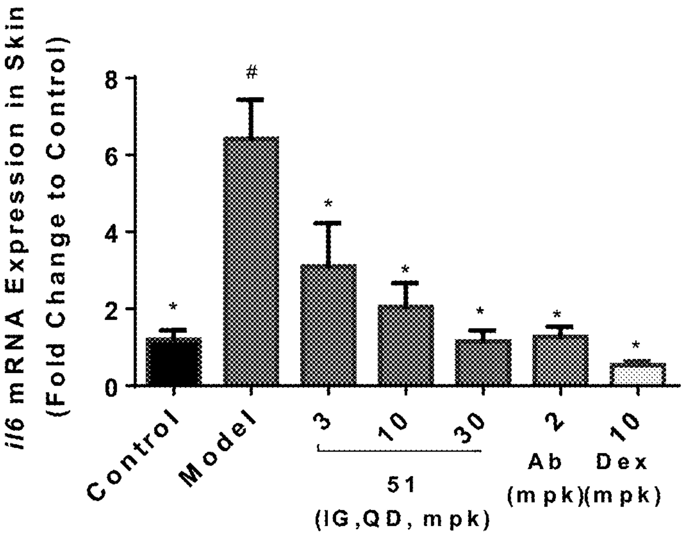
Figure 2A:
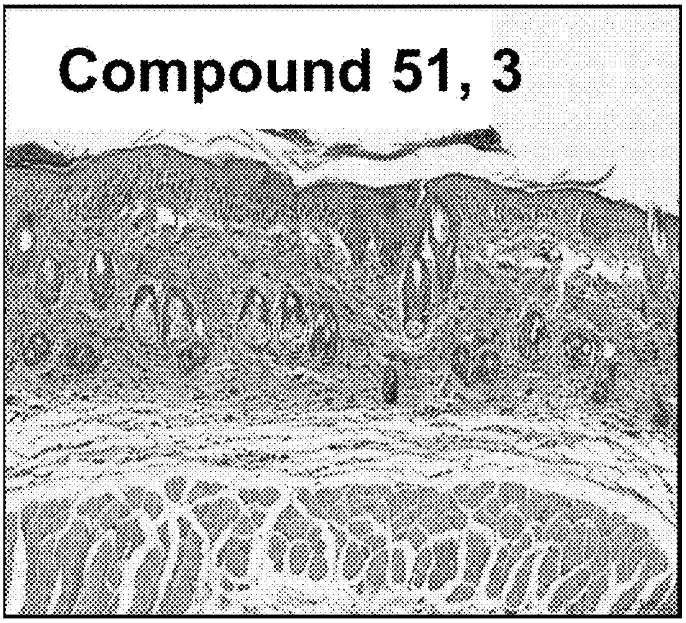
FIGS. 2A-G show skin tissue section results of the imiquimod-induced psoriasis mouse model.
Figure 2B:
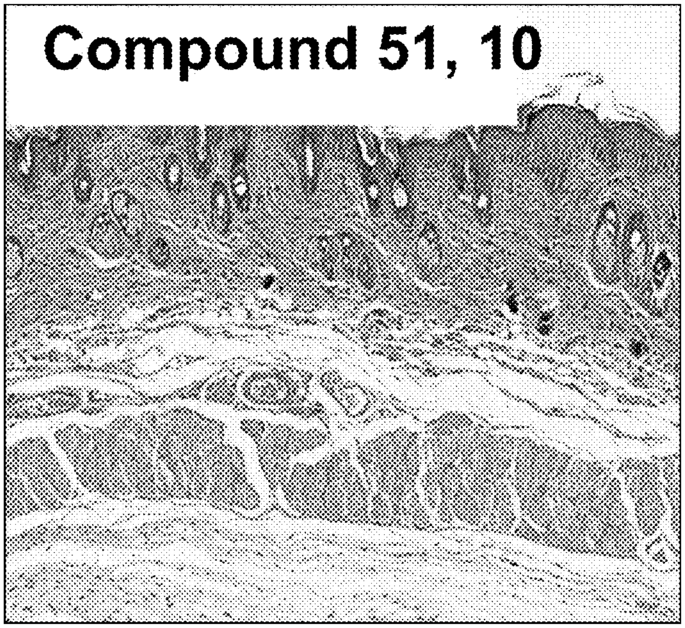
Figure 2C:
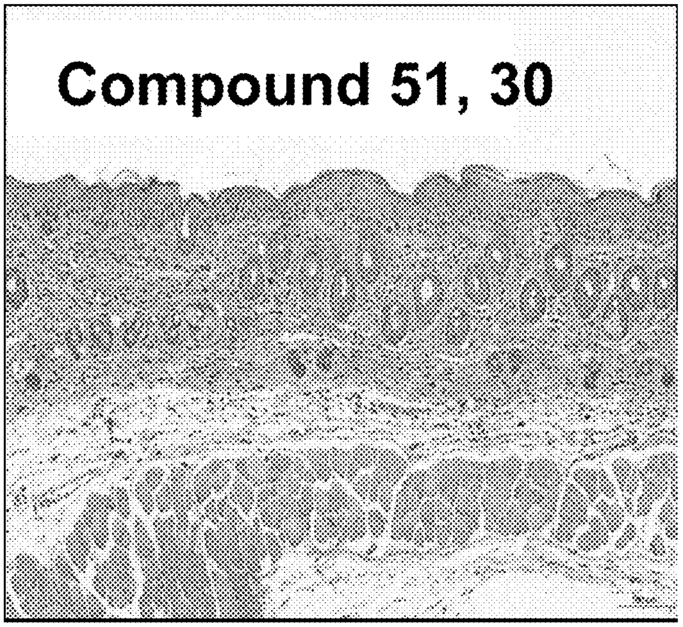
Figure 2D:
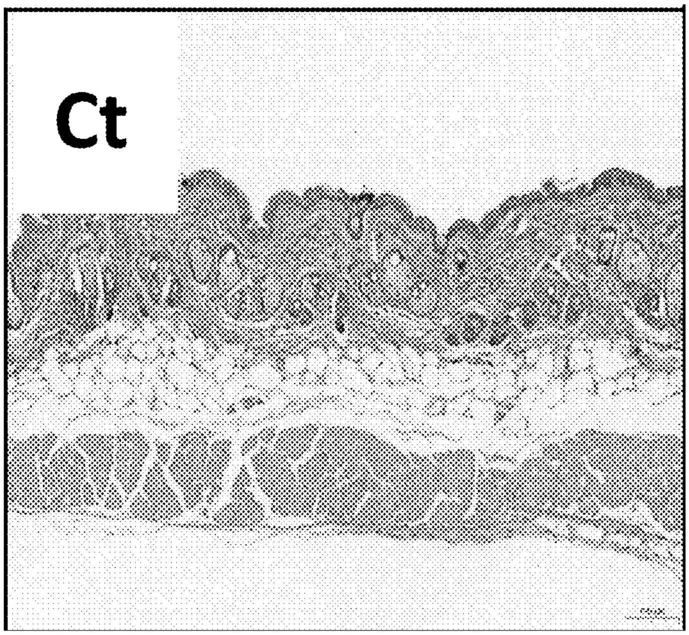
Figure 2E:
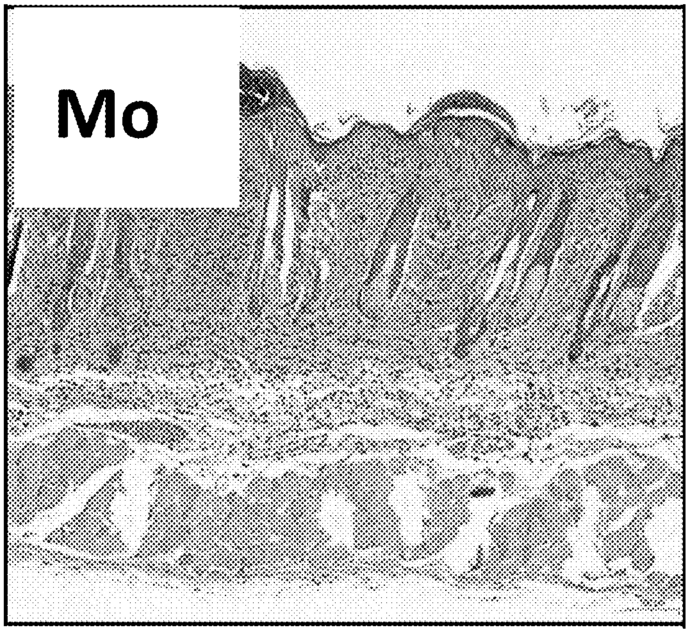
Figure 2F:
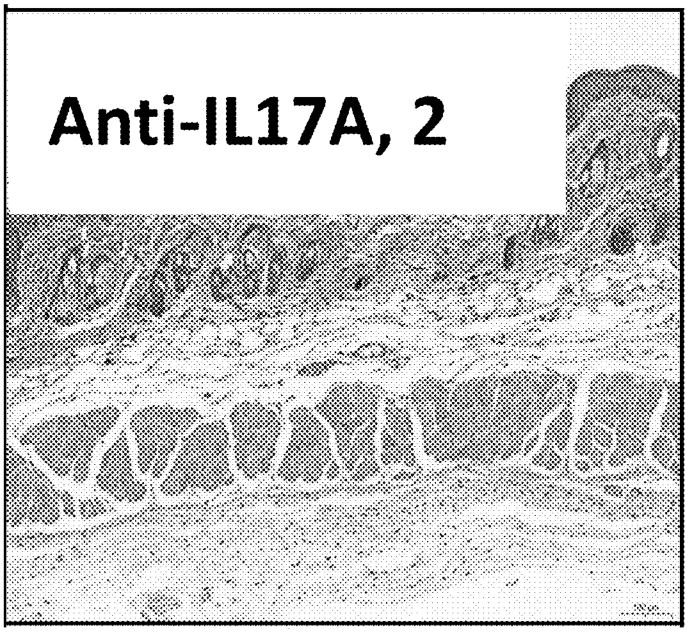
Figure 2G:
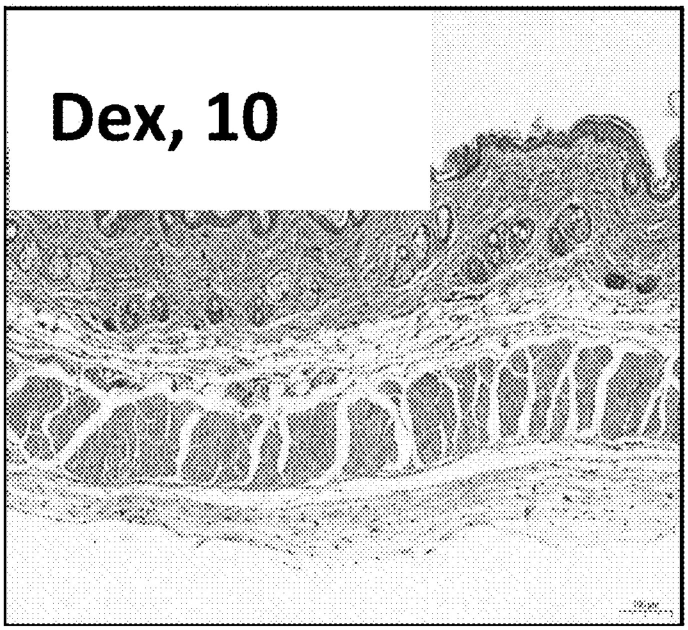

On day 5 of the experiment, the skins of mice in each group were collected, the mRNA expression level of IL6 was detected by quantitative reverse transcription polymerase chain reaction (RT-qPCR) test. The results were shown in FIG. 1C demonstrating that the administration dose of the compound 51 in each group dependently reversed the up-regulation of IL6 expression level. On day 5 of the experiment, the plasma of mice in each group was collected, and the IL6 protein level was measured. The results were shown in FIG. 1D demonstrating that the administration dose of the compound 51 in each group dependently inhibited the increase of IL6 protein level in the plasma.

On day 5 of the model, the skin samples were collected from the back of each mouse. The samples were fixed in 4% paraformaldehyde, and stained with hematoxylin-eosin (HE) to investigate the protective effect of compound 51 on skin pathological damage. The results were shown in FIGS. 2A-G and demonstrated that the administration doses of the compound 51 at 3, 10 and 30 mg/kg may inhibit the infiltration and damage of skin inflammatory cells induced by IMQ at different levels.

Experimental Example 5 Efficacy Test in Myelencephalitis Mouse Model

A myelin oligodendrocyte glycoprotein (MOG)-induced myelencephalitis model was established in 10-week-old female C57BL/6 mice. From one day before establishing the model, the mice were administrated with the compound prepared in this application by gavage (30 mg/kg) or intraperitoneal injection (3, 10, 30 mg/kg) once a day, or the IL-17A antibody by intraperitoneal injection every three days (10 mg/kg for the first time and the second time, then 5 mg/kg). The control group and model group were given blank solvent. Daily scoring curve was drawn according to the scoring system of the encephalomyelitis model in mice.

On the day 21 of the model, the mouse brain and spinal cord samples were collected and fixed in 4% paraformaldehyde for HE staining to investigate the protective effect of the compounds on the histopathological injury of the cerebral and spinal cord tissues.

In conclusion, the new compound represented by formula I disclosed in this application exhibited satisfactory inhibitory activity against IL-17A, and provides a new medicinal possibility for clinical treatment of diseases associated with IL-17A abnormal activity.

What is claimed is:

1. A compound of formula (IV), or a deuterated compound, a stereoisomer, or a pharmaceutically acceptable salt thereof:

(IV)

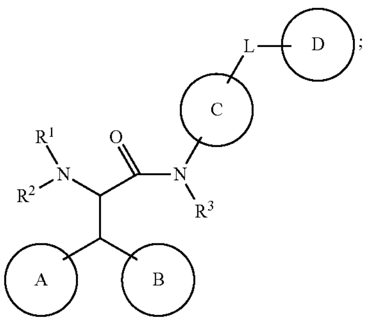

;

wherein $R^1$ is —C(O)$R^{11}$; $R^{11}$ is selected from the group consisting of

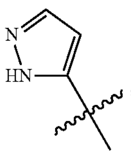, 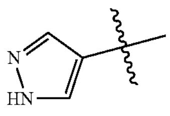, 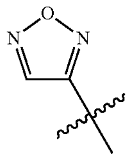,

-continued

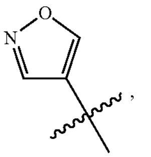, 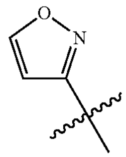 and 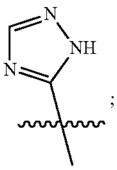;

wherein

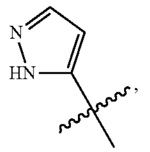, 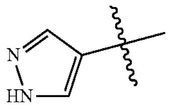, 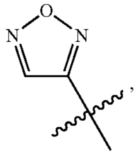, 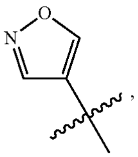, 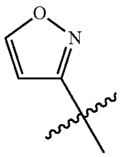 and 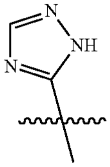

are independently unsubstituted or substituted with 1, 2 or 3 $R^{1a}$ groups; the $R^{1a}$ groups are each independently selected from the group consisting of hydrogen, halogen, cyano, —$C_{1-6}$ alkyl, halogen-substituted —$C_{1-6}$ alkyl, 3- to 6-membered cycloalkyl and —$C_{0-2}$ alkylene-O$R^{1b}$; wherein $R^{1b}$ is selected from the group consisting of hydrogen, $C_{1-6}$ alkyl and halogen-substituted $C_{1-6}$ alkyl;

$R^2$ and $R^3$ are independently selected from the group consisting of hydrogen and —$C_{1-6}$ alkyl;

the A ring is selected from the group consisting of

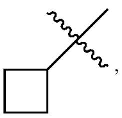, 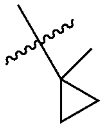, 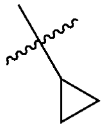, 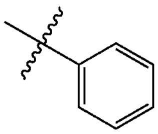 and 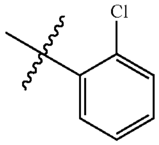;

the B ring is selected from the group consisting of

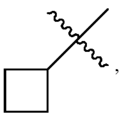, 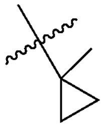, 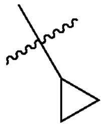, 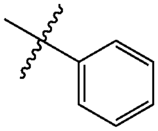 and 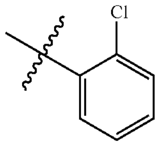;

the C ring is selected from the group consisting of

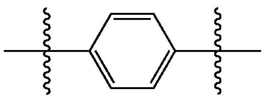,

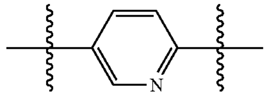, 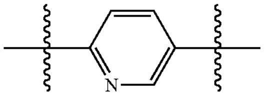,

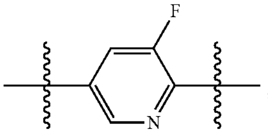, 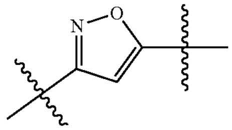 and

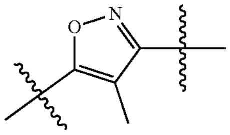;

and the D ring is

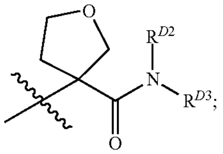

$R^{D2}$ and $R^{D3}$ are independently selected from the group consisting of hydrogen, $C_{1-6}$ alkyl, —$C_{0-2}$ alkylene-$OR^{D4}$, —$C_{0-2}$ alkylene-(3- to 10-membered cycloalkyl), —$C_{0-2}$ alkylene-(3- to 10-membered heterocycloalkyl), —$C_{0-2}$ alkylene-(5- to 10-membered aromatic ring) and —$C_{0-2}$ alkylene-(5- to 10-membered heteroaromatic ring); wherein alkyl, alkylene, cycloalkyl, heterocycloalkyl, aromatic ring and heteroaromatic ring are independently unsubstituted or substituted with 1, 2 or 3 $R^{D4}$ groups;

the $R^{D4}$ groups are each independently selected from the group consisting of hydrogen, $C_{1-6}$ alkyl, halogen-substituted $C_{1-6}$ alkyl, halogen, cyano, =O, nitro, —OH, —O($C_{1-6}$ alkyl), —$NH_2$, —NH($C_{1-6}$ alkyl), —N($C_{1-6}$ alkyl) ($C_{1-6}$ alkyl), —$C_{0-2}$ alkylene-(3- to 10-membered cycloalkyl), —$C_{0-2}$ alkylene-(3- to 10-membered heterocycloalkyl), —$C_{0-2}$ alkylene-(5- to 10-membered aromatic ring) and —$C_{0-2}$ alkylene-(5- to 10-membered heteroaromatic ring).

2. The compound of claim 1, wherein the D ring selected from the group consisting of

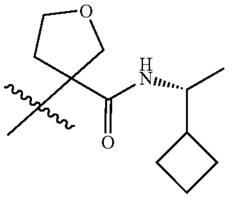, 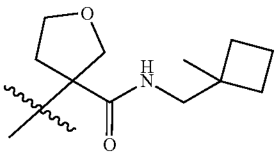,

-continued

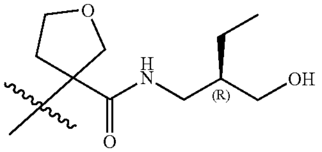 and

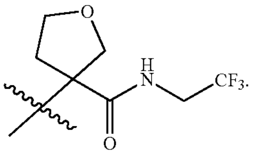

3. A compound of formula (V), or a deuterated compound, a stereoisomer, or a pharmaceutically acceptable salt thereof:

(V)

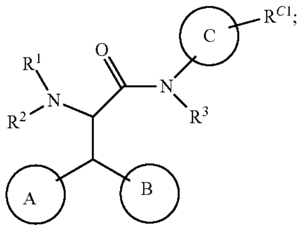

wherein $R^1$ is —C(O)$R^{11}$; $R^{11}$ is selected from the group consisting of

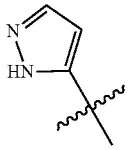, 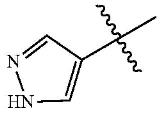, 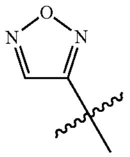,

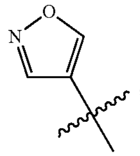, 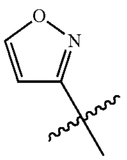 and 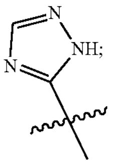

wherein

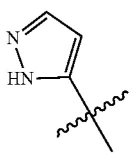, 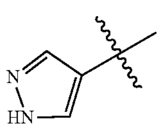, 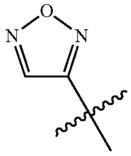,

-continued

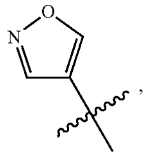,
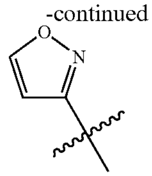
and
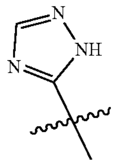

are independently unsubstituted or substituted with 1, 2 or 3 $R^{1a}$ groups; the $R^{1a}$ groups are each independently selected from the group consisting of hydrogen, halogen, cyano, $-C_{1-6}$ alkyl, halogen-substituted $-C_{1-6}$ alkyl, 3- to 6-membered cycloalkyl and $-C_{0-2}$ alkylene-$OR^{1b}$; wherein $R^{1b}$ is selected from the group consisting of hydrogen, $C_{1-6}$ alkyl and halogen-substituted $C_{1-6}$ alkyl;

$R^2$ and $R^3$ are independently selected from the group consisting of hydrogen and $-C_{1-6}$ alkyl;

the A ring is selected from the group consisting of

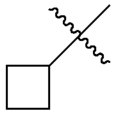,
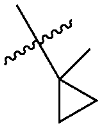,
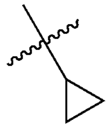,
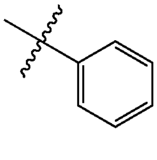
and
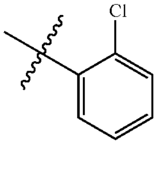;

the B ring is selected from the group consisting of

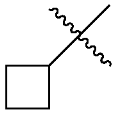,
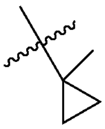,
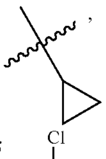,
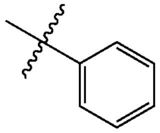
and
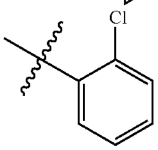;

and

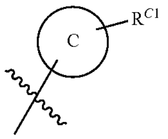

is selected from the group consisting of

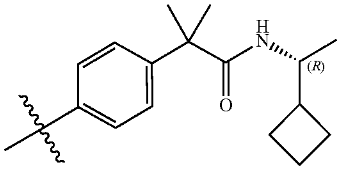,
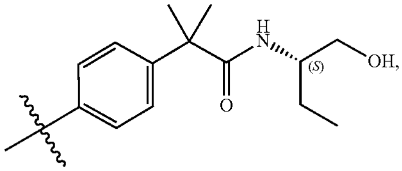
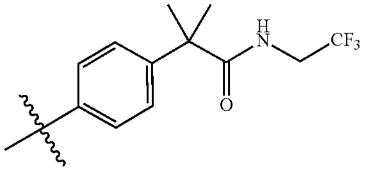
and
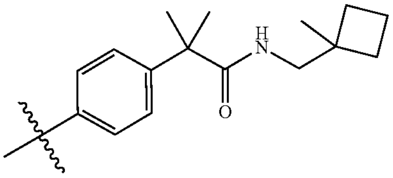.

4. A pharmaceutical composition, comprising:
the compound of claim 1, or a deuterated compound, a stereoisomer or a pharmaceutically acceptable salt thereof; and
a pharmaceutically-acceptable adjuvant.

5. A method for treating an interleukin-17A (IL-17A)-mediated disease in a subject in need thereof, comprising:
administrating to the subject a therapeutically effective amount of the compound of claim 1, or a deuterated compound, a stereoisomer, or a pharmaceutically acceptable salt thereof.

6. The method of claim 5, wherein the IL-17A-mediated disease is selected from the group consisting of inflammation, autoimmune diseases, infectious diseases, cancer, precancerous syndromes and a combination thereof.

7. A method for treating an interleukin-17A (IL-17A)-mediated disease in a subject in need thereof, comprising:
administrating to the subject a therapeutically effective amount of the compound of claim 3, or a deuterated compound, a stereoisomer, or a pharmaceutically acceptable salt thereof.

8. The method of claim 7, wherein the IL-17A-mediated disease is selected from the group consisting of inflammation, autoimmune diseases, infectious diseases, cancer, precancerous syndromes and a combination thereof.

9. A pharmaceutical composition, comprising:
the compound of claim 3, or a deuterated compound, a stereoisomer or a pharmaceutically acceptable salt thereof; and
a pharmaceutically-acceptable adjuvant.

* * * * *